US012746118B2

(12) United States Patent
Nawalakhe et al.

(10) Patent No.: US 12,746,118 B2
(45) Date of Patent: Sep. 29, 2026

(54) TEXTILES FOR IMPLANTATION

(71) Applicant: EDWARDS LIFESCIENCES CORPORATION, Irvine, CA (US)

(72) Inventors: Rupesh Gajanan Nawalakhe, Trabuco Canyon, CA (US); Sandip Vasant Pawar, Irvine, CA (US); Siddharth Vad, Irvine, CA (US); Matthew A. Peterson, Costa Mesa, CA (US); David Robert Landon, Huntington Beach, CA (US); Zachary Charles VanEvery, Irvine, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 442 days.

(21) Appl. No.: 18/371,303

(22) Filed: Sep. 21, 2023

(65) Prior Publication Data

US 2024/0008978 A1 Jan. 11, 2024

Related U.S. Application Data

(63) Continuation of application No. PCT/US2022/025593, filed on Apr. 20, 2022.
(Continued)

(51) Int. Cl.
*A61F 2/24* (2006.01)
*A61F 2/00* (2006.01)
*A61F 2/848* (2013.01)

(52) U.S. Cl.
CPC .... *A61F 2/2418* (2013.01); *A61F 2002/0081* (2013.01); *A61F 2002/8483* (2013.01);
(Continued)

(58) Field of Classification Search
CPC ............ A61F 2/2418; A61F 2002/0081; A61F 2002/8483; A61F 2002/8486;
(Continued)

(56) References Cited

U.S. PATENT DOCUMENTS 3,409,013 A 11/1968 Berry
3,472,230 A 10/1969 Fogarty
(Continued)

FOREIGN PATENT DOCUMENTS

CA 2304325 C 5/2008
DE 2246526 A1 3/1973
(Continued)

OTHER PUBLICATIONS

Andersen, et al., “Transluminal implantation of artificial heart valves. Description of a new expandable aortic valve and initial results with implantation by catheter technqiue in closed chest pigs.” European Heart Journal (1992), 13, 704-708.
(Continued)

*Primary Examiner* — Bruce E Snow
(74) *Attorney, Agent, or Firm* — Thomas C. Richardson

(57) ABSTRACT

A fabric having a honeycomb weave pattern is provided for use with medical implants. The fabric may be heat treated to increase a thickness and texture of the fabric. The fabric may be compliant and compressible for providing cushioning within a patient’s body. For example, the fabric may be applied to a prosthetic valve to cushion a portion of the prosthetic heart valve. The fabric may also be textured to provide enhanced friction between the prosthetic heart valve and the surrounding native tissue. Enhanced friction may be achieved by weave patterns or by the inclusion of protrusions or barbs in the fabric.

17 Claims, 27 Drawing Sheets

Related U.S. Application Data

(60) Provisional application No. 63/177,700, filed on Apr. 21, 2021.

(52) U.S. Cl.
CPC ................. *A61F 2002/8486* (2013.01); *A61F 2210/0076* (2013.01); *A61F 2250/001* (2013.01); *A61F 2250/0069* (2013.01)

(58) Field of Classification Search
CPC ........ A61F 2210/0076; A61F 2250/001; A61F 2250/0069; A61F 2250/0017; D10B 2509/00; D10B 2509/06; D03D 3/08; D03D 13/004
See application file for complete search history.

(56) References Cited

U.S. PATENT DOCUMENTS

| | | | |
|---|---|---|---|
| 3,548,417 | A | 12/1970 | Kischer et al. |
| 3,587,115 | A | 6/1971 | Shiley |
| 3,657,744 | A | 4/1972 | Ersek |
| 3,671,979 | A | 6/1972 | Moulopoulos |
| 3,714,671 | A | 2/1973 | Edwards et al. |
| 3,739,402 | A | 6/1973 | Cooley et al. |
| 3,755,823 | A | 9/1973 | Hancock |
| 4,011,947 | A | 3/1977 | Sawyer |
| 4,035,849 | A | 7/1977 | Angell et al. |
| 4,056,854 | A | 11/1977 | Boretos et al. |
| 4,079,468 | A | 3/1978 | Liotta et al. |
| 4,106,129 | A | 8/1978 | Carpentier et al. |
| 4,204,283 | A | 5/1980 | Bellhouse et al. |
| 4,222,126 | A | 9/1980 | Boretos et al. |
| 4,265,694 | A | 5/1981 | Boretos et al. |
| 4,297,749 | A | 11/1981 | Davis et al. |
| 4,339,831 | A | 7/1982 | Johnson |
| 4,340,977 | A | 7/1982 | Brownlee et al. |
| 4,343,048 | A | 8/1982 | Ross et al. |
| 4,345,340 | A | 8/1982 | Rosen |
| 4,373,216 | A | 2/1983 | Klawitter |
| 4,406,022 | A | 9/1983 | Roy |
| 4,470,157 | A | 9/1984 | Love |
| 4,477,930 | A | 10/1984 | Totten et al. |
| 4,490,859 | A | 1/1985 | Black et al. |
| 4,535,483 | A | 8/1985 | Klawitter et al. |
| 4,553,545 | A | 11/1985 | Maass et al. |
| 4,574,803 | A | 3/1986 | Storz |
| 4,592,340 | A | 6/1986 | Boyles |
| 4,605,407 | A | 8/1986 | Black et al. |
| 4,612,011 | A | 9/1986 | Kautzky |
| 4,643,732 | A | 2/1987 | Pietsch et al. |
| 4,655,771 | A | 4/1987 | Wallsten |
| 4,692,164 | A | 9/1987 | Dzemeshkevich et al. |
| 4,733,665 | A | 3/1988 | Palmaz |
| 4,759,758 | A | 7/1988 | Gabbay |
| 4,762,128 | A | 8/1988 | Rosenbluth |
| 4,777,951 | A | 10/1988 | Cribier et al. |
| 4,787,899 | A | 11/1988 | Lazarus |
| 4,787,901 | A | 11/1988 | Baykut |
| 4,796,629 | A | 1/1989 | Grayzel |
| 4,829,990 | A | 5/1989 | Thuroff et al. |
| 4,851,001 | A | 7/1989 | Taheri |
| 4,856,516 | A | 8/1989 | Hillstead |
| 4,865,600 | A | 9/1989 | Carpentier et al. |
| 4,878,495 | A | 11/1989 | Grayzel |
| 4,878,906 | A | 11/1989 | Lindemann et al. |
| 4,883,458 | A | 11/1989 | Shiber |
| 4,922,905 | A | 5/1990 | Strecker |
| 4,966,604 | A | 10/1990 | Reiss |
| 4,979,939 | A | 12/1990 | Shiber |
| 4,986,830 | A | 1/1991 | Owens et al. |
| 4,994,077 | A | 2/1991 | Dobben |
| 5,007,896 | A | 4/1991 | Shiber |
| 5,026,366 | A | 6/1991 | Leckrone |
| 5,032,128 | A | 7/1991 | Alonso |
| 5,037,434 | A | 8/1991 | Lane |
| 5,047,041 | A | 9/1991 | Samuels |
| 5,059,177 | A | 10/1991 | Towne et al. |
| 5,080,668 | A | 1/1992 | Bolz et al. |
| 5,085,635 | A | 2/1992 | Cragg |
| 5,089,015 | A | 2/1992 | Ross |
| 5,108,370 | A | 4/1992 | Walinsky |
| 5,152,771 | A | 10/1992 | Sabbaghian et al. |
| 5,163,953 | A | 11/1992 | Vince |
| 5,167,628 | A | 12/1992 | Boyles |
| 5,192,297 | A | 3/1993 | Hull |
| 5,232,446 | A | 8/1993 | Arney |
| 5,266,073 | A | 11/1993 | Wall |
| 5,282,847 | A | 2/1994 | Trescony et al. |
| 5,295,958 | A | 3/1994 | Shturman |
| 5,326,371 | A | 7/1994 | Love et al. |
| 5,332,402 | A | 7/1994 | Teitelbaum |
| 5,360,444 | A | 11/1994 | Kusuhara |
| 5,370,685 | A | 12/1994 | Stevens |
| 5,397,351 | A | 3/1995 | Pavcnik et al. |
| 5,411,055 | A | 5/1995 | Kane |
| 5,411,522 | A | 5/1995 | Trott |
| 5,411,552 | A | 5/1995 | Andersen et al. |
| 5,415,667 | A | 5/1995 | Frater |
| 5,443,446 | A | 8/1995 | Shturman |
| 5,480,424 | A | 1/1996 | Cox |
| 5,500,014 | A | 3/1996 | Quijano et al. |
| 5,545,209 | A | 8/1996 | Roberts et al. |
| 5,545,214 | A | 8/1996 | Stevens |
| 5,549,665 | A | 8/1996 | Vesely et al. |
| 5,554,185 | A | 9/1996 | Block et al. |
| 5,571,175 | A | 11/1996 | Vanney et al. |
| 5,591,185 | A | 1/1997 | Kilmer et al. |
| 5,599,305 | A | 2/1997 | Hermann et al. |
| 5,607,464 | A | 3/1997 | Trescony et al. |
| 5,609,626 | A | 3/1997 | Quijano et al. |
| 5,639,274 | A | 6/1997 | Fischell et al. |
| 5,665,115 | A | 9/1997 | Cragg |
| 5,697,382 | A | 12/1997 | Love et al. |
| 5,716,417 | A | 2/1998 | Girard et al. |
| 5,728,068 | A | 3/1998 | Leone et al. |
| 5,749,890 | A | 5/1998 | Shaknovich |
| 5,756,476 | A | 5/1998 | Epstein et al. |
| 5,769,812 | A | 6/1998 | Stevens et al. |
| 5,800,508 | A | 9/1998 | Goicoechea et al. |
| 5,840,081 | A | 11/1998 | Andersen et al. |
| 5,855,597 | A | 1/1999 | Jayaraman |
| 5,855,601 | A | 1/1999 | Bessler et al. |
| 5,855,602 | A | 1/1999 | Angell |
| 5,906,619 | A | 5/1999 | Olson et al. |
| 5,925,063 | A | 7/1999 | Khosravi |
| 5,957,949 | A | 9/1999 | Leonhardt et al. |
| 5,968,068 | A | 10/1999 | Dehdashtian et al. |
| 6,027,525 | A | 2/2000 | Suh et al. |
| 6,042,607 | A | 3/2000 | Williamson et al. |
| 6,086,612 | A | 7/2000 | Jansen |
| 6,113,631 | A | 9/2000 | Jansen |
| 6,132,473 | A | 10/2000 | Williams et al. |
| 6,168,614 | B1 | 1/2001 | Andersen et al. |
| 6,171,335 | B1 | 1/2001 | Wheatley et al. |
| 6,174,327 | B1 | 1/2001 | Mertens et al. |
| 6,210,408 | B1 | 4/2001 | Chandrasekaran et al. |
| 6,217,585 | B1 | 4/2001 | Houser et al. |
| 6,221,091 | B1 | 4/2001 | Khosravi |
| 6,231,602 | B1 | 5/2001 | Carpentier et al. |
| 6,245,040 | B1 | 6/2001 | Inderbitzen et al. |
| 6,245,102 | B1 | 6/2001 | Jayaraman |
| 6,251,093 | B1 | 6/2001 | Valley et al. |
| 6,287,339 | B1 | 9/2001 | Vazquez et al. |
| 6,299,637 | B1 | 10/2001 | Shaolian et al. |
| 6,302,906 | B1 | 10/2001 | Goicoechea et al. |
| 6,306,141 | B1 | 10/2001 | Jervis |
| 6,312,465 | B1 | 11/2001 | Griffin et al. |
| 6,338,740 | B1 | 1/2002 | Carpentier |
| 6,350,277 | B1 | 2/2002 | Kocur |
| 6,358,277 | B1 | 3/2002 | Duran |
| 6,379,372 | B1 | 4/2002 | Dehdashtian et al. |
| 6,425,916 | B1 | 7/2002 | Garrison et al. |
| 6,440,164 | B1 | 8/2002 | DiMatteo et al. |

(56) References Cited

U.S. PATENT DOCUMENTS

| | | | |
|---|---|---|---|
| 6,454,799 | B1 | 9/2002 | Schreck |
| 6,458,153 | B1 | 10/2002 | Bailey et al. |
| 6,461,382 | B1 | 10/2002 | Cao |
| 6,468,660 | B2 | 10/2002 | Ogle et al. |
| 6,482,228 | B1 | 11/2002 | Norred |
| 6,488,704 | B1 | 12/2002 | Connelly et al. |
| 6,527,800 | B1 | 3/2003 | McGuckin et al. |
| 6,527,979 | B2 | 3/2003 | Constantz et al. |
| 6,540,782 | B1 | 4/2003 | Snyders |
| 6,569,196 | B1 | 5/2003 | Vesely |
| 6,575,959 | B1 | 6/2003 | Sarge et al. |
| 6,582,462 | B1 | 6/2003 | Andersen et al. |
| 6,605,112 | B1 | 8/2003 | Moll et al. |
| 6,610,088 | B1 | 8/2003 | Gabbay |
| 6,629,534 | B1 | 10/2003 | Goar et al. |
| 6,676,698 | B2 | 1/2004 | McGuckin et al. |
| 6,695,878 | B2 | 2/2004 | McGuckin et al. |
| 6,712,836 | B1 | 3/2004 | Berg et al. |
| 6,716,207 | B2 | 4/2004 | Farnholtz |
| 6,729,356 | B1 | 5/2004 | Baker et al. |
| 6,730,118 | B2 | 5/2004 | Spenser et al. |
| 6,733,525 | B2 | 5/2004 | Yang et al. |
| 6,746,422 | B1 | 6/2004 | Noriega et al. |
| 6,749,560 | B1 | 6/2004 | Konstorum et al. |
| 6,767,362 | B2 | 7/2004 | Schreck |
| 6,780,200 | B2 | 8/2004 | Jansen |
| 6,790,229 | B1 | 9/2004 | Berreklouw |
| 6,790,230 | B2 | 9/2004 | Beyersdorf et al. |
| 6,830,584 | B1 | 12/2004 | Seguin |
| 6,875,231 | B2 | 4/2005 | Anduiza et al. |
| 6,893,460 | B2 | 5/2005 | Spenser et al. |
| 6,908,481 | B2 | 6/2005 | Cribier |
| 6,974,476 | B2 | 12/2005 | McGuckin et al. |
| 7,018,406 | B2 | 3/2006 | Seguin et al. |
| 7,186,265 | B2 | 3/2007 | Sharkawy et al. |
| 7,192,440 | B2 | 3/2007 | Andreas et al. |
| 7,198,646 | B2 | 4/2007 | Figulla et al. |
| 7,201,772 | B2 | 4/2007 | Schwammenthal et al. |
| 7,276,078 | B2 | 10/2007 | Spenser et al. |
| 7,276,084 | B2 | 10/2007 | Yang et al. |
| 7,318,278 | B2 | 1/2008 | Zhang et al. |
| 7,374,571 | B2 | 5/2008 | Pease et al. |
| 7,381,210 | B2 | 6/2008 | Zarbatany et al. |
| 7,381,219 | B2 | 6/2008 | Salahieh et al. |
| 7,393,360 | B2 | 7/2008 | Spenser et al. |
| 7,429,269 | B2 | 9/2008 | Schwammenthal et al. |
| 7,442,204 | B2 | 10/2008 | Schwammenthal et al. |
| 7,445,631 | B2 | 11/2008 | Salahieh et al. |
| 7,462,191 | B2 | 12/2008 | Spenser et al. |
| 7,510,575 | B2 | 3/2009 | Spenser et al. |
| 7,524,330 | B2 | 4/2009 | Berreklouw |
| 7,530,253 | B2 | 5/2009 | Spenser et al. |
| 7,553,324 | B2 | 6/2009 | Andreas et al. |
| 7,579,381 | B2 | 8/2009 | Dove |
| 7,585,321 | B2 | 9/2009 | Cribier |
| 7,618,446 | B2 | 11/2009 | Andersen et al. |
| 7,621,948 | B2 | 11/2009 | Herrmann et al. |
| 7,704,222 | B2 | 4/2010 | Wilk et al. |
| 7,736,327 | B2 | 6/2010 | Wilk et al. |
| 7,748,389 | B2 | 7/2010 | Salahieh et al. |
| 7,753,949 | B2 | 7/2010 | Lamphere et al. |
| 7,806,919 | B2 | 10/2010 | Bloom et al. |
| 7,824,443 | B2 | 11/2010 | Salahieh et al. |
| 7,837,727 | B2 | 11/2010 | Goetz et al. |
| 7,892,281 | B2 | 2/2011 | Seguin et al. |
| 7,914,569 | B2 | 3/2011 | Nguyen et al. |
| 7,914,575 | B2 | 3/2011 | Guyenot et al. |
| 7,959,672 | B2 | 6/2011 | Salahieh et al. |
| 7,972,378 | B2 | 7/2011 | Tabor et al. |
| 7,981,151 | B2 | 7/2011 | Rowe |
| 7,993,392 | B2 | 8/2011 | Righini et al. |
| 7,993,394 | B2 | 8/2011 | Hariton et al. |
| 8,007,992 | B2 | 8/2011 | Tian et al. |
| 8,016,877 | B2 | 9/2011 | Seguin et al. |
| 8,029,556 | B2 | 10/2011 | Rowe |
| 8,052,750 | B2 | 11/2011 | Tuval et al. |
| 8,070,800 | B2 | 12/2011 | Lock et al. |
| 8,070,802 | B2 | 12/2011 | Lamphere et al. |
| 8,075,615 | B2 | 12/2011 | Eberhardt et al. |
| 8,080,054 | B2 | 12/2011 | Rowe |
| 8,092,520 | B2 | 1/2012 | Quadri |
| 8,092,521 | B2 | 1/2012 | Figulla et al. |
| 8,109,996 | B2 | 2/2012 | Stacchino et al. |
| 8,118,866 | B2 | 2/2012 | Herrmann et al. |
| 8,136,218 | B2 | 3/2012 | Millwee et al. |
| 8,137,398 | B2 | 3/2012 | Tuval et al. |
| 8,157,852 | B2 | 4/2012 | Bloom et al. |
| 8,167,932 | B2 | 5/2012 | Bourang et al. |
| 8,167,934 | B2 | 5/2012 | Styrc et al. |
| 8,182,530 | B2 | 5/2012 | Huber |
| 8,206,437 | B2 | 6/2012 | Bonhoeffer et al. |
| 8,216,174 | B2 | 7/2012 | Wilk et al. |
| 8,216,301 | B2 | 7/2012 | Bonhoeffer et al. |
| 8,219,229 | B2 | 7/2012 | Cao et al. |
| 8,220,121 | B2 | 7/2012 | Hendriksen et al. |
| 8,236,045 | B2 | 8/2012 | Benichou et al. |
| 8,246,675 | B2 | 8/2012 | Zegdi |
| 8,246,678 | B2 | 8/2012 | Salahieh et al. |
| 8,252,051 | B2 | 8/2012 | Chau et al. |
| 8,252,052 | B2 | 8/2012 | Salahieh et al. |
| 8,287,584 | B2 | 10/2012 | Salahieh et al. |
| 8,313,525 | B2 | 11/2012 | Tuval et al. |
| 8,317,858 | B2 | 11/2012 | Straubinger et al. |
| 8,323,335 | B2 | 12/2012 | Rowe et al. |
| 8,337,541 | B2 | 12/2012 | Quadri et al. |
| 8,353,953 | B2 | 1/2013 | Giannetti et al. |
| 8,398,704 | B2 | 3/2013 | Straubinger et al. |
| 8,403,983 | B2 | 3/2013 | Quadri et al. |
| 8,414,644 | B2 | 4/2013 | Quadri et al. |
| 8,414,645 | B2 | 4/2013 | Dwork et al. |
| 8,416,643 | B2 | 4/2013 | Magee |
| 8,444,689 | B2 | 5/2013 | Zhang |
| 8,449,599 | B2 | 5/2013 | Chau et al. |
| 8,454,685 | B2 | 6/2013 | Hariton et al. |
| 8,460,368 | B2 | 6/2013 | Taylor et al. |
| 8,460,370 | B2 | 6/2013 | Zakay et al. |
| 8,470,023 | B2 | 6/2013 | Eidenschink et al. |
| 8,470,028 | B2 | 6/2013 | Thornton et al. |
| 8,475,521 | B2 | 7/2013 | Suri et al. |
| 8,475,523 | B2 | 7/2013 | Duffy |
| 8,479,380 | B2 | 7/2013 | Malewicz et al. |
| 8,491,650 | B2 | 7/2013 | Wiemeyer et al. |
| 8,500,733 | B2 | 8/2013 | Watson |
| 8,500,798 | B2 | 8/2013 | Rowe et al. |
| 8,511,244 | B2 | 8/2013 | Holecek et al. |
| 8,512,401 | B2 | 8/2013 | Murray et al. |
| 8,518,096 | B2 | 8/2013 | Nelson |
| 8,518,106 | B2 | 8/2013 | Duffy et al. |
| 8,562,663 | B2 | 10/2013 | Mearns et al. |
| 8,579,963 | B2 | 11/2013 | Tabor |
| 8,579,964 | B2 | 11/2013 | Lane et al. |
| 8,591,570 | B2 | 11/2013 | Revuelta et al. |
| 8,617,236 | B2 | 12/2013 | Paul et al. |
| 8,640,521 | B2 | 2/2014 | Righini et al. |
| 8,647,381 | B2 | 2/2014 | Essinger et al. |
| 8,652,145 | B2 | 2/2014 | Maimon et al. |
| 8,652,201 | B2 | 2/2014 | Oberti et al. |
| 8,652,202 | B2 | 2/2014 | Alon et al. |
| 8,652,203 | B2 | 2/2014 | Quadri et al. |
| 8,668,733 | B2 | 3/2014 | Haug et al. |
| 8,679,174 | B2 | 3/2014 | Ottma et al. |
| 8,679,404 | B2 | 3/2014 | Liburd et al. |
| 8,685,086 | B2 | 4/2014 | Navia et al. |
| 8,721,708 | B2 | 5/2014 | Sèguin et al. |
| 8,721,714 | B2 | 5/2014 | Kelley |
| 8,728,154 | B2 | 5/2014 | Alkhatib |
| 8,728,155 | B2 | 5/2014 | Montorfano et al. |
| 8,740,974 | B2 | 6/2014 | Lambrecht et al. |
| 8,740,976 | B2 | 6/2014 | Tran et al. |
| 8,747,458 | B2 | 6/2014 | Tuval et al. |
| 8,747,459 | B2 | 6/2014 | Nguyen et al. |
| 8,758,432 | B2 | 6/2014 | Solem |
| 8,764,818 | B2 | 7/2014 | Gregg |
| 8,771,344 | B2 | 7/2014 | Tran et al. |

(56) References Cited

U.S. PATENT DOCUMENTS

| | | | |
|---|---|---|---|
| 8,778,020 | B2 | 7/2014 | Gregg et al. |
| 8,784,337 | B2 | 7/2014 | Voeller et al. |
| 8,784,478 | B2 | 7/2014 | Tuval et al. |
| 8,784,481 | B2 | 7/2014 | Alkhatib et al. |
| 8,790,387 | B2 | 7/2014 | Nguyen et al. |
| 8,795,357 | B2 | 8/2014 | Yohanan et al. |
| 8,808,356 | B2 | 8/2014 | Braido et al. |
| 8,828,078 | B2 | 9/2014 | Salahieh et al. |
| 8,828,079 | B2 | 9/2014 | Thielen et al. |
| 8,834,564 | B2 | 9/2014 | Tuval et al. |
| 8,858,620 | B2 | 10/2014 | Salahieh et al. |
| 8,870,948 | B1 | 10/2014 | Erzberger et al. |
| 8,870,950 | B2 | 10/2014 | Hacohen |
| 8,876,893 | B2 | 11/2014 | Dwork et al. |
| 8,911,455 | B2 | 12/2014 | Quadri et al. |
| 8,926,693 | B2 | 1/2015 | Duffy et al. |
| 8,926,694 | B2 | 1/2015 | Costello |
| 8,939,960 | B2 | 1/2015 | Rosenman et al. |
| 8,945,209 | B2 | 2/2015 | Bonyuet et al. |
| 8,961,593 | B2 | 2/2015 | Bonhoeffer et al. |
| 8,961,595 | B2 | 2/2015 | Alkhatib |
| 8,974,524 | B2 | 3/2015 | Yeung et al. |
| 8,979,922 | B2 | 3/2015 | Jayasinghe et al. |
| 8,986,375 | B2 | 3/2015 | Garde et al. |
| 8,998,980 | B2 | 4/2015 | Shipley et al. |
| 9,005,273 | B2 | 4/2015 | Salahieh et al. |
| 9,011,521 | B2 | 4/2015 | Haug et al. |
| 9,011,523 | B2 | 4/2015 | Seguin |
| 9,011,524 | B2 | 4/2015 | Eberhardt |
| 9,028,545 | B2 | 5/2015 | Taylor |
| 9,034,032 | B2 | 5/2015 | McLean et al. |
| 9,055,937 | B2 | 6/2015 | Rowe et al. |
| 9,066,801 | B2 | 6/2015 | Kovalsky et al. |
| 9,078,749 | B2 | 7/2015 | Lutter et al. |
| 9,078,751 | B2 | 7/2015 | Naor |
| 9,125,738 | B2 | 9/2015 | Figulla et al. |
| 9,173,737 | B2 | 11/2015 | Hill et al. |
| 9,180,004 | B2 | 11/2015 | Alkhatib |
| 9,186,249 | B2 | 11/2015 | Rolando et al. |
| 9,277,990 | B2 | 3/2016 | Klima et al. |
| 9,277,993 | B2 | 3/2016 | Gamarra et al. |
| 9,289,291 | B2 | 3/2016 | Gorman et al. |
| 9,295,551 | B2 | 3/2016 | Straubinger et al. |
| 9,445,897 | B2 | 9/2016 | Bishop et al. |
| 9,456,877 | B2 | 10/2016 | Weitzner et al. |
| 9,681,968 | B2 | 6/2017 | Goetz et al. |
| 9,687,345 | B2 | 6/2017 | Rabito et al. |
| 9,700,329 | B2 | 7/2017 | Metzger et al. |
| 9,700,411 | B2 | 7/2017 | Klima et al. |
| 9,724,083 | B2 | 8/2017 | Quadri et al. |
| 9,730,790 | B2 | 8/2017 | Quadri et al. |
| 9,730,791 | B2 | 8/2017 | Ratz et al. |
| 9,795,479 | B2 | 10/2017 | Lim et al. |
| 9,833,313 | B2 | 12/2017 | Board et al. |
| 9,861,473 | B2 | 1/2018 | Lafontaine |
| 9,861,476 | B2 | 1/2018 | Salahieh et al. |
| 9,861,477 | B2 | 1/2018 | Backus et al. |
| 9,867,698 | B2 | 1/2018 | Kovalsky et al. |
| 9,877,830 | B2 | 1/2018 | Lim et al. |
| 9,889,029 | B2 | 2/2018 | Li et al. |
| 9,895,225 | B2 * | 2/2018 | Rolando ............... A61F 2/2409 |
| 9,925,045 | B2 | 3/2018 | Creaven et al. |
| 10,004,599 | B2 | 6/2018 | Rabito et al. |
| 10,117,744 | B2 | 11/2018 | Ratz et al. |
| 10,179,044 | B2 | 1/2019 | Ratz et al. |
| 10,219,897 | B2 | 3/2019 | Essinger et al. |
| 10,350,065 | B2 | 7/2019 | Quadri |
| 10,350,066 | B2 | 7/2019 | Cooper et al. |
| 10,376,363 | B2 | 8/2019 | Quadri et al. |
| 10,555,809 | B2 | 2/2020 | Hastings et al. |
| 10,575,951 | B2 | 3/2020 | Johnson et al. |
| 10,583,000 | B2 | 3/2020 | Ratz et al. |
| 10,639,146 | B2 | 5/2020 | Quadri et al. |
| 10,695,177 | B2 | 6/2020 | Hariton et al. |
| 10,758,344 | B2 | 9/2020 | Hariton et al. |
| 11,406,499 | B2 | 8/2022 | Zhang et al. |
| 11,452,598 | B2 | 9/2022 | Essinger et al. |
| 11,672,658 | B2 | 6/2023 | Hariton et al. |
| 11,701,225 | B2 | 7/2023 | Hammer et al. |
| 11,903,829 | B1 | 2/2024 | Ma et al. |
| 2001/0021872 | A1 | 9/2001 | Bailey et al. |
| 2002/0032481 | A1 | 3/2002 | Gabbay |
| 2002/0045929 | A1 | 4/2002 | Diaz |
| 2002/0052644 | A1 | 5/2002 | Shaolian et al. |
| 2002/0107565 | A1 | 8/2002 | Greenhalgh |
| 2002/0123802 | A1 | 9/2002 | Snyders |
| 2002/0173842 | A1 | 11/2002 | Buchanan |
| 2003/0050694 | A1 | 3/2003 | Yang et al. |
| 2003/0100939 | A1 | 5/2003 | Yodfat et al. |
| 2003/0105517 | A1 | 6/2003 | White et al. |
| 2003/0120333 | A1 | 6/2003 | Ouriel et al. |
| 2003/0130729 | A1 | 7/2003 | Paniagua et al. |
| 2003/0149477 | A1 | 8/2003 | Gabbay |
| 2003/0149478 | A1 | 8/2003 | Figulla et al. |
| 2003/0158597 | A1 | 8/2003 | Quiachon et al. |
| 2003/0176914 | A1 | 9/2003 | Rabkin et al. |
| 2003/0199971 | A1 | 10/2003 | Tower et al. |
| 2003/0212454 | A1 | 11/2003 | Scott et al. |
| 2003/0220683 | A1 | 11/2003 | Minasian et al. |
| 2004/0039436 | A1 | 2/2004 | Spenser et al. |
| 2004/0092858 | A1 | 5/2004 | Wilson et al. |
| 2004/0093075 | A1 | 5/2004 | Kuehne |
| 2004/0117009 | A1 | 6/2004 | Cali et al. |
| 2004/0133263 | A1 | 7/2004 | Dusbabek et al. |
| 2004/0133273 | A1 | 7/2004 | Cox |
| 2004/0186563 | A1 | 9/2004 | Lobbi |
| 2004/0186565 | A1 | 9/2004 | Schreck |
| 2004/0210307 | A1 | 10/2004 | Khairkhahan |
| 2004/0215325 | A1 | 10/2004 | Penn et al. |
| 2004/0225353 | A1 | 11/2004 | McGuckin et al. |
| 2004/0236411 | A1 | 11/2004 | Sarac et al. |
| 2004/0260389 | A1 | 12/2004 | Case et al. |
| 2005/0033398 | A1 | 2/2005 | Seguin |
| 2005/0075727 | A1 | 4/2005 | Wheatley |
| 2005/0090887 | A1 | 4/2005 | Pryor |
| 2005/0096738 | A1 | 5/2005 | Cali et al. |
| 2005/0107872 | A1 | 5/2005 | Mensah et al. |
| 2005/0137682 | A1 | 6/2005 | Justino |
| 2005/0137686 | A1 | 6/2005 | Salahieh et al. |
| 2005/0137687 | A1 | 6/2005 | Salahieh et al. |
| 2005/0137688 | A1 | 6/2005 | Salahieh et al. |
| 2005/0137691 | A1 | 6/2005 | Salahieh et al. |
| 2005/0137698 | A1 | 6/2005 | Salahieh et al. |
| 2005/0159811 | A1 | 7/2005 | Lane |
| 2005/0182486 | A1 | 8/2005 | Gabbay |
| 2005/0203614 | A1 | 9/2005 | Forster et al. |
| 2005/0203617 | A1 | 9/2005 | Forster et al. |
| 2005/0216079 | A1 | 9/2005 | MaCoviak |
| 2005/0234546 | A1 | 10/2005 | Nugent et al. |
| 2005/0288766 | A1 | 12/2005 | Plain et al. |
| 2006/0020327 | A1 | 1/2006 | Lashinski et al. |
| 2006/0025857 | A1 | 2/2006 | Bergheim et al. |
| 2006/0058872 | A1 | 3/2006 | Salahieh et al. |
| 2006/0095115 | A1 | 5/2006 | Bladillah et al. |
| 2006/0142837 | A1 | 6/2006 | Haverkost et al. |
| 2006/0149350 | A1 | 7/2006 | Patel et al. |
| 2006/0161249 | A1 | 7/2006 | Realyvasquez et al. |
| 2006/0173537 | A1 | 8/2006 | Yang et al. |
| 2006/0195134 | A1 | 8/2006 | Crittenden |
| 2006/0195183 | A1 | 8/2006 | Navia et al. |
| 2006/0212110 | A1 | 9/2006 | Osborne et al. |
| 2006/0229719 | A1 | 10/2006 | Marquez et al. |
| 2006/0241745 | A1 | 10/2006 | Solem |
| 2006/0259135 | A1 | 11/2006 | Navia et al. |
| 2006/0259137 | A1 | 11/2006 | Artof et al. |
| 2006/0276874 | A1 | 12/2006 | Wilson et al. |
| 2006/0293745 | A1 | 12/2006 | Carpentier et al. |
| 2007/0005131 | A1 | 1/2007 | Taylor |
| 2007/0010877 | A1 | 1/2007 | Salahieh et al. |
| 2007/0027534 | A1 | 2/2007 | Bergheim et al. |
| 2007/0043435 | A1 | 2/2007 | Seguin et al. |
| 2007/0050021 | A1 | 3/2007 | Johnson |
| 2007/0066863 | A1 | 3/2007 | Rafiee et al. |
| 2007/0088431 | A1 | 4/2007 | Bourang et al. |

(56) References Cited

U.S. PATENT DOCUMENTS

| | | | |
|---|---|---|---|
| 2007/0100432 | A1 | 5/2007 | Case et al. |
| 2007/0100439 | A1 | 5/2007 | Cangialosi et al. |
| 2007/0112422 | A1 | 5/2007 | Dehdashtian |
| 2007/0129794 | A1 | 6/2007 | Realyvasquez |
| 2007/0142906 | A1 | 6/2007 | Figulla et al. |
| 2007/0156224 | A1 | 7/2007 | Cioanta et al. |
| 2007/0203503 | A1 | 8/2007 | Salahieh et al. |
| 2007/0203575 | A1 | 8/2007 | Forster et al. |
| 2007/0213813 | A1 | 9/2007 | Von Segesser et al. |
| 2007/0244552 | A1 | 10/2007 | Salahieh et al. |
| 2007/0255394 | A1 | 11/2007 | Ryan |
| 2007/0270943 | A1 | 11/2007 | Solem et al. |
| 2008/0021546 | A1 | 1/2008 | Patz et al. |
| 2008/0065011 | A1 | 3/2008 | Marchand et al. |
| 2008/0071361 | A1 | 3/2008 | Tuval et al. |
| 2008/0071362 | A1 | 3/2008 | Tuval et al. |
| 2008/0071363 | A1 | 3/2008 | Tuval et al. |
| 2008/0071366 | A1 | 3/2008 | Tuval et al. |
| 2008/0071368 | A1 | 3/2008 | Tuval et al. |
| 2008/0071369 | A1 | 3/2008 | Tuval et al. |
| 2008/0082164 | A1 | 4/2008 | Friedman |
| 2008/0082165 | A1 | 4/2008 | Wilson et al. |
| 2008/0082166 | A1 | 4/2008 | Styrc et al. |
| 2008/0097581 | A1 | 4/2008 | Shanley |
| 2008/0114442 | A1 | 5/2008 | Mitchell et al. |
| 2008/0125853 | A1 | 5/2008 | Bailey et al. |
| 2008/0147179 | A1 | 6/2008 | Cai et al. |
| 2008/0147183 | A1 | 6/2008 | Styrc |
| 2008/0154355 | A1 | 6/2008 | Benichou et al. |
| 2008/0161910 | A1 | 7/2008 | Revuelta et al. |
| 2008/0177381 | A1 | 7/2008 | Navia et al. |
| 2008/0183273 | A1 | 7/2008 | Mesana et al. |
| 2008/0208328 | A1 | 8/2008 | Antocci et al. |
| 2008/0208332 | A1 | 8/2008 | Lamphere et al. |
| 2008/0221672 | A1 | 9/2008 | Lamphere et al. |
| 2008/0228254 | A1 | 9/2008 | Ryan |
| 2008/0255660 | A1 | 10/2008 | Guyenot et al. |
| 2008/0255661 | A1 | 10/2008 | Straubinger et al. |
| 2008/0281411 | A1 | 11/2008 | Berreklouw |
| 2009/0005863 | A1 | 1/2009 | Goetz et al. |
| 2009/0054968 | A1 | 2/2009 | Bonhoeffer et al. |
| 2009/0054974 | A1 | 2/2009 | McGuckin et al. |
| 2009/0076598 | A1 | 3/2009 | Salahieh et al. |
| 2009/0112309 | A1 | 4/2009 | Jaramillo et al. |
| 2009/0138079 | A1 | 5/2009 | Tuval et al. |
| 2009/0157175 | A1 | 6/2009 | Benichou |
| 2009/0164005 | A1 | 6/2009 | Dove et al. |
| 2009/0171432 | A1 | 7/2009 | Von Segesser et al. |
| 2009/0171447 | A1 | 7/2009 | Von Segesser et al. |
| 2009/0171456 | A1 | 7/2009 | Kveen et al. |
| 2009/0182413 | A1 | 7/2009 | Burkart et al. |
| 2009/0188964 | A1 | 7/2009 | Orlov |
| 2009/0216310 | A1 | 8/2009 | Straubinger et al. |
| 2009/0216313 | A1 | 8/2009 | Straubinger et al. |
| 2009/0216322 | A1 | 8/2009 | Le et al. |
| 2009/0222076 | A1 | 9/2009 | Figulla et al. |
| 2009/0234443 | A1 | 9/2009 | Ottma et al. |
| 2009/0240320 | A1 | 9/2009 | Tuval et al. |
| 2009/0270972 | A1 | 10/2009 | Lane |
| 2009/0276027 | A1 | 11/2009 | Glynn |
| 2009/0276040 | A1 | 11/2009 | Rowe et al. |
| 2009/0281618 | A1 | 11/2009 | Hill et al. |
| 2009/0281619 | A1 | 11/2009 | Le et al. |
| 2009/0287296 | A1 | 11/2009 | Manasse |
| 2009/0287299 | A1 | 11/2009 | Tabor et al. |
| 2009/0292350 | A1 | 11/2009 | Eberhardt et al. |
| 2009/0306768 | A1 | 12/2009 | Quadri |
| 2009/0319037 | A1 | 12/2009 | Rowe et al. |
| 2010/0016958 | A1 | 1/2010 | St. Goar et al. |
| 2010/0024818 | A1 | 2/2010 | Stenzler et al. |
| 2010/0049313 | A1 | 2/2010 | Alon et al. |
| 2010/0069852 | A1 | 3/2010 | Kelley |
| 2010/0114305 | A1 | 5/2010 | Kang et al. |
| 2010/0131054 | A1 | 5/2010 | Tuval et al. |
| 2010/0137979 | A1 | 6/2010 | Tuval et al. |
| 2010/0145438 | A1 | 6/2010 | Barone |
| 2010/0174362 | A1 | 7/2010 | Straubinger et al. |
| 2010/0191326 | A1 | 7/2010 | Alkhatib |
| 2010/0204781 | A1 | 8/2010 | Alkhatib |
| 2010/0217382 | A1 | 8/2010 | Chau et al. |
| 2010/0249894 | A1 | 9/2010 | Oba et al. |
| 2010/0249911 | A1 | 9/2010 | Alkhatib |
| 2010/0256723 | A1 | 10/2010 | Murray |
| 2010/0262231 | A1 | 10/2010 | Tuval et al. |
| 2010/0305685 | A1 | 12/2010 | Millwee et al. |
| 2010/0312333 | A1 | 12/2010 | Navia et al. |
| 2011/0015616 | A1 | 1/2011 | Straubinger et al. |
| 2011/0015729 | A1 | 1/2011 | Jimenez et al. |
| 2011/0029072 | A1 | 2/2011 | Gabbay |
| 2011/0137397 | A1 | 6/2011 | Chau et al. |
| 2011/0178597 | A9 | 7/2011 | Navia et al. |
| 2011/0208290 | A1 | 8/2011 | Straubinger et al. |
| 2011/0208297 | A1 | 8/2011 | Tuval et al. |
| 2011/0208298 | A1 | 8/2011 | Tuval et al. |
| 2011/0224785 | A1 | 9/2011 | Hacohen |
| 2011/0238159 | A1 | 9/2011 | Guyenot et al. |
| 2011/0264196 | A1 | 10/2011 | Savage et al. |
| 2011/0264198 | A1 | 10/2011 | Murray et al. |
| 2011/0288634 | A1 | 11/2011 | Tuval et al. |
| 2011/0313515 | A1 | 12/2011 | Quadri et al. |
| 2011/0319989 | A1 | 12/2011 | Lane et al. |
| 2012/0022639 | A1 | 1/2012 | Hacohen et al. |
| 2012/0035722 | A1 | 2/2012 | Tuval |
| 2012/0041550 | A1 | 2/2012 | Salahieh et al. |
| 2012/0046741 | A1 | 2/2012 | Tuval et al. |
| 2012/0046742 | A1 | 2/2012 | Tuval et al. |
| 2012/0078360 | A1 | 3/2012 | Rafiee |
| 2012/0101570 | A1 | 4/2012 | Tuval et al. |
| 2012/0101571 | A1 | 4/2012 | Thambar et al. |
| 2012/0101572 | A1 | 4/2012 | Kovalsky et al. |
| 2012/0123529 | A1 | 5/2012 | Levi et al. |
| 2012/0185039 | A1 | 7/2012 | Tuval et al. |
| 2012/0197386 | A1 | 8/2012 | Von Segesser et al. |
| 2012/0209374 | A1 | 8/2012 | Bonhoeffer et al. |
| 2012/0215303 | A1 | 8/2012 | Quadri et al. |
| 2012/0239142 | A1 | 9/2012 | Liu et al. |
| 2012/0271398 | A1 | 10/2012 | Essinger et al. |
| 2012/0283823 | A1 | 11/2012 | Bonhoeffer et al. |
| 2012/0290062 | A1 | 11/2012 | McNamara et al. |
| 2012/0296418 | A1 | 11/2012 | Bonyuet et al. |
| 2012/0310328 | A1 | 12/2012 | Olson et al. |
| 2012/0310336 | A1 | 12/2012 | Figulla et al. |
| 2013/0006294 | A1 | 1/2013 | Kashkarov et al. |
| 2013/0035759 | A1 | 2/2013 | Gross et al. |
| 2013/0073035 | A1 | 3/2013 | Tuval et al. |
| 2013/0079869 | A1 | 3/2013 | Straubinger et al. |
| 2013/0172992 | A1 | 7/2013 | Gross et al. |
| 2013/0190861 | A1 | 7/2013 | Chau et al. |
| 2013/0190862 | A1 | 7/2013 | Pintor et al. |
| 2013/0197622 | A1 | 8/2013 | Mitra et al. |
| 2013/0211508 | A1 | 8/2013 | Lane et al. |
| 2013/0253635 | A1 | 9/2013 | Straubinger et al. |
| 2013/0253642 | A1 | 9/2013 | Brecker |
| 2013/0310928 | A1 | 11/2013 | Morriss et al. |
| 2013/0331929 | A1 | 12/2013 | Mitra et al. |
| 2013/0338766 | A1 | 12/2013 | Hastings et al. |
| 2013/0345786 | A1 | 12/2013 | Behan |
| 2014/0018912 | A1 | 1/2014 | Delaloye et al. |
| 2014/0025163 | A1 | 1/2014 | Padala et al. |
| 2014/0039611 | A1 | 2/2014 | Lane et al. |
| 2014/0052237 | A1 | 2/2014 | Lane et al. |
| 2014/0100651 | A1 | 4/2014 | Kheradvar et al. |
| 2014/0163668 | A1 | 6/2014 | Rafiee |
| 2014/0172077 | A1 | 6/2014 | Bruchman et al. |
| 2014/0172083 | A1 | 6/2014 | Bruchman et al. |
| 2014/0194981 | A1 | 7/2014 | Menk et al. |
| 2014/0207231 | A1 | 7/2014 | Hacohen et al. |
| 2014/0214157 | A1 | 7/2014 | Börtlein et al. |
| 2014/0222136 | A1 | 8/2014 | Geist et al. |
| 2014/0222139 | A1 | 8/2014 | Nguyen et al. |
| 2014/0222142 | A1 | 8/2014 | Kovalsky et al. |
| 2014/0222144 | A1 | 8/2014 | Eberhardt et al. |
| 2014/0243966 | A1 | 8/2014 | Garde et al. |
| 2014/0257467 | A1 | 9/2014 | Lane et al. |

(56) References Cited

U.S. PATENT DOCUMENTS

| | | | |
|---|---|---|---|
| 2014/0277390 A1 | 9/2014 | Ratz et al. | |
| 2014/0277403 A1 | 9/2014 | Peter | |
| 2014/0277412 A1 | 9/2014 | Börtlein et al. | |
| 2014/0277422 A1 | 9/2014 | Ratz et al. | |
| 2014/0277426 A1 | 9/2014 | Dakin et al. | |
| 2014/0277427 A1 | 9/2014 | Ratz et al. | |
| 2014/0296973 A1 | 10/2014 | Bergheim et al. | |
| 2014/0296975 A1 | 10/2014 | Tegels et al. | |
| 2014/0303719 A1 | 10/2014 | Cox et al. | |
| 2014/0309728 A1 | 10/2014 | Dehdashtian et al. | |
| 2014/0324160 A1 | 10/2014 | Benichou et al. | |
| 2014/0324164 A1 | 10/2014 | Gross et al. | |
| 2014/0330368 A1 | 11/2014 | Gloss et al. | |
| 2014/0330371 A1 | 11/2014 | Gloss et al. | |
| 2014/0330372 A1 | 11/2014 | Weston et al. | |
| 2014/0336754 A1 | 11/2014 | Gurskis et al. | |
| 2014/0343669 A1 | 11/2014 | Lane et al. | |
| 2014/0343670 A1 | 11/2014 | Bakis et al. | |
| 2014/0350666 A1 | 11/2014 | Righini | |
| 2014/0350668 A1 | 11/2014 | Delaloye et al. | |
| 2014/0358223 A1 | 12/2014 | Rafiee et al. | |
| 2014/0364939 A1 | 12/2014 | Deshmukh et al. | |
| 2014/0364943 A1 | 12/2014 | Conklin | |
| 2014/0371842 A1 | 12/2014 | Marquez et al. | |
| 2014/0371844 A1 | 12/2014 | Dale et al. | |
| 2014/0371847 A1 | 12/2014 | Madrid et al. | |
| 2014/0371848 A1 | 12/2014 | Murray et al. | |
| 2015/0005863 A1 | 1/2015 | Para | |
| 2015/0018944 A1 | 1/2015 | O'Connell et al. | |
| 2015/0039083 A1 | 2/2015 | Rafiee | |
| 2015/0142100 A1 | 5/2015 | Morriss et al. | |
| 2015/0142103 A1 | 5/2015 | Vidlund | |
| 2015/0148731 A1 | 5/2015 | Mcnamara et al. | |
| 2015/0173897 A1 | 6/2015 | Raanani et al. | |
| 2015/0196390 A1 | 7/2015 | Ma et al. | |
| 2015/0209141 A1 | 7/2015 | Braido et al. | |
| 2015/0272737 A1 | 10/2015 | Dale et al. | |
| 2015/0297346 A1 | 10/2015 | Duffy et al. | |
| 2015/0335429 A1 | 11/2015 | Morriss et al. | |
| 2015/0351903 A1 | 12/2015 | Morriss et al. | |
| 2015/0359629 A1 | 12/2015 | Ganesan et al. | |
| 2016/0000591 A1 | 1/2016 | Lei et al. | |
| 2016/0030169 A1 | 2/2016 | Shahriari | |
| 2016/0030170 A1 | 2/2016 | Alkhatib et al. | |
| 2016/0030171 A1 | 2/2016 | Quijano et al. | |
| 2016/0038280 A1 | 2/2016 | Morriss et al. | |
| 2016/0038281 A1 | 2/2016 | Delaloye et al. | |
| 2016/0074160 A1 | 3/2016 | Christianson et al. | |
| 2016/0106537 A1 | 4/2016 | Christianson et al. | |
| 2016/0113765 A1 | 4/2016 | Ganesan et al. | |
| 2016/0113768 A1 | 4/2016 | Ganesan et al. | |
| 2016/0143732 A1 | 5/2016 | Glimsdale | |
| 2016/0158010 A1 | 6/2016 | Lim et al. | |
| 2016/0166383 A1 | 6/2016 | Lim et al. | |
| 2016/0184097 A1 | 6/2016 | Lim et al. | |
| 2016/0199206 A1 | 7/2016 | Lim et al. | |
| 2016/0213473 A1 | 7/2016 | Hacohen et al. | |
| 2016/0235529 A1 | 8/2016 | Ma et al. | |
| 2016/0278923 A1 | 9/2016 | Krans et al. | |
| 2016/0279386 A1 | 9/2016 | Dale et al. | |
| 2016/0310267 A1 | 10/2016 | Zeng et al. | |
| 2017/0042678 A1 | 2/2017 | Ganesan et al. | |
| 2017/0079785 A1 | 3/2017 | Li | |
| 2017/0128209 A1 | 5/2017 | Morriss et al. | |
| 2017/0216023 A1 | 8/2017 | Lane et al. | |
| 2017/0216575 A1 | 8/2017 | Asleson et al. | |
| 2017/0257902 A1 | 9/2017 | Xing et al. | |
| 2017/0258614 A1 | 9/2017 | Griffin | |
| 2017/0325945 A1 | 11/2017 | Dale et al. | |
| 2017/0325954 A1 | 11/2017 | Perszyk | |
| 2017/0333186 A1 | 11/2017 | Spargias | |
| 2017/0348096 A1 | 12/2017 | Anderson | |
| 2017/0367821 A1 | 12/2017 | Landon et al. | |
| 2017/0367823 A1 | 12/2017 | Hariton et al. | |
| 2018/0014931 A1 | 1/2018 | Morriss et al. | |
| 2018/0021129 A1 | 1/2018 | Peterson et al. | |
| 2018/0055629 A1 | 3/2018 | Oba et al. | |
| 2018/0055636 A1 | 3/2018 | Valencia et al. | |
| 2018/0085218 A1 | 3/2018 | Eidenschink | |
| 2018/0110534 A1 | 4/2018 | Gavala et al. | |
| 2018/0110622 A1 | 4/2018 | Gregg et al. | |
| 2018/0116790 A1 | 5/2018 | Ratz et al. | |
| 2018/0126119 A1 | 5/2018 | McNiven et al. | |
| 2018/0296341 A1 | 10/2018 | Noe et al. | |
| 2018/0344457 A1 | 12/2018 | Gross et al. | |
| 2018/0344490 A1 | 12/2018 | Fox et al. | |
| 2019/0008639 A1 | 1/2019 | Landon et al. | |
| 2019/0008640 A1 | 1/2019 | Cooper et al. | |
| 2019/0060072 A1 | 2/2019 | Zeng | |
| 2019/0262129 A1* | 8/2019 | Cooper | A61F 2/2418 |
| 2020/0000579 A1 | 1/2020 | Manash et al. | |
| 2020/0108225 A1 | 4/2020 | Jamal et al. | |
| 2020/0138572 A1 | 5/2020 | Zhao et al. | |
| 2020/0163761 A1 | 5/2020 | Hariton et al. | |
| 2020/0188098 A1 | 6/2020 | Alkhatib et al. | |
| 2020/0323668 A1 | 10/2020 | Diedering et al. | |
| 2020/0345494 A1 | 11/2020 | Srinimukesh et al. | |
| 2020/0352718 A1 | 11/2020 | Rowe et al. | |
| 2021/0015615 A1 | 1/2021 | Groothuis et al. | |
| 2021/0145576 A1 | 5/2021 | Becerra et al. | |
| 2021/0228354 A1 | 7/2021 | Rafiee et al. | |
| 2021/0259835 A1 | 8/2021 | Tyler, II et al. | |
| 2021/0307900 A1* | 10/2021 | Hacohen | A61F 2/2466 |
| 2021/0378817 A1 | 12/2021 | Nia et al. | |
| 2021/0386544 A1 | 12/2021 | Cooper et al. | |
| 2022/0142777 A1 | 5/2022 | Scheinblum et al. | |
| 2022/0287836 A1 | 9/2022 | Landon et al. | |
| 2022/0346993 A1 | 11/2022 | Srinimukesh et al. | |
| 2023/0000624 A1 | 1/2023 | Okabe et al. | |
| 2023/0200980 A1 | 6/2023 | Peterson et al. | |
| 2023/0218391 A1 | 7/2023 | Dass et al. | |
| 2023/0380963 A1 | 11/2023 | Kaufman et al. | |
| 2023/0390052 A1 | 12/2023 | Okafor et al. | |
| 2023/0404753 A1 | 12/2023 | Luong et al. | |
| 2024/0008978 A1 | 1/2024 | Nawalakhe et al. | |
| 2024/0091000 A1 | 3/2024 | King et al. | |

FOREIGN PATENT DOCUMENTS

| | | | |
|---|---|---|---|
| DE | 2246526 | C3 | 7/1981 |
| DE | 19532846 | A1 | 3/1997 |
| DE | 19546692 | A1 | 6/1997 |
| DE | 19857887 | A1 | 7/2000 |
| DE | 19907646 | A1 | 8/2000 |
| DE | 10049812 | A1 | 4/2002 |
| DE | 10049813 | C1 | 4/2002 |
| DE | 10049814 | A1 | 4/2002 |
| DE | 10049815 | A1 | 4/2002 |
| DE | 19546692 | C2 | 11/2002 |
| DE | 10010074 | B4 | 4/2005 |
| DE | 19857887 | B4 | 5/2005 |
| DE | 102006052564 | B3 | 12/2007 |
| EP | 0144167 | A2 | 6/1985 |
| EP | 0103546 | B1 | 5/1988 |
| EP | 0592410 | B1 | 10/1995 |
| EP | 0850607 | A1 | 7/1998 |
| EP | 0597967 | B1 | 12/1999 |
| EP | 1057460 | A1 | 12/2000 |
| EP | 1088529 | A2 | 4/2001 |
| EP | 1469797 | A1 | 10/2004 |
| EP | 1259194 | B1 | 2/2005 |
| EP | 1171059 | B1 | 11/2005 |
| EP | 1469797 | B1 | 11/2005 |
| EP | 1255510 | B1 | 4/2007 |
| EP | 1239901 | B1 | 10/2007 |
| EP | 1849440 | A1 | 10/2007 |
| EP | 1570809 | B1 | 1/2009 |
| EP | 1472996 | B1 | 9/2009 |
| EP | 1653888 | B1 | 9/2009 |
| EP | 1935377 | B1 | 3/2010 |
| EP | 1369098 | B1 | 4/2014 |
| EP | 2124826 | B1 | 7/2014 |
| EP | 2745805 | B1 | 6/2015 |
| EP | 2749254 | B1 | 6/2015 |

(56) References Cited

FOREIGN PATENT DOCUMENTS

| | | | |
|---|---|---|---|
| EP | 2918249 | A2 | 9/2015 |
| EP | 2168536 | B1 | 4/2016 |
| EP | 2413842 | B1 | 8/2017 |
| EP | 2446915 | B1 | 1/2018 |
| EP | 3057541 | B1 | 1/2018 |
| EP | 3037064 | B1 | 3/2018 |
| EP | 3046511 | B1 | 3/2018 |
| EP | 3142603 | B1 | 3/2018 |
| EP | 3075354 | B1 | 11/2018 |
| EP | 3184083 | B1 | 2/2019 |
| EP | 2918249 | B1 | 4/2020 |
| EP | 3417813 | B1 | 5/2020 |
| EP | 2777616 | B1 | 8/2020 |
| EP | 3139864 | B1 | 11/2020 |
| EP | 2750630 | B1 | 6/2021 |
| EP | 2777617 | B1 | 9/2022 |
| EP | 2948103 | B1 | 12/2022 |
| EP | 2967858 | B1 | 1/2023 |
| EP | 3570779 | B1 | 2/2023 |
| EP | 3294220 | B1 | 12/2023 |
| FR | 2788217 | A1 | 7/2000 |
| GB | 1264471 | A | 2/1972 |
| GB | 1315844 | A | 5/1973 |
| GB | 2056023 | A | 3/1981 |
| GB | 2398245 | A | 8/2004 |
| GB | 2398245 | B | 3/2007 |
| SU | 1271508 | A1 | 11/1986 |
| WO | 1991016041 | A1 | 10/1991 |
| WO | 1991017720 | A1 | 11/1991 |
| WO | 1992017118 | A1 | 10/1992 |
| WO | 1993001768 | A1 | 2/1993 |
| WO | 1997024080 | A1 | 7/1997 |
| WO | 1998029057 | A1 | 7/1998 |
| WO | 1999033414 | A1 | 7/1999 |
| WO | 1999040964 | A1 | 8/1999 |
| WO | 1999047075 | A1 | 9/1999 |
| WO | 2000018333 | A1 | 4/2000 |
| WO | 2000041652 | A1 | 7/2000 |
| WO | 2000047139 | A1 | 8/2000 |
| WO | 2000061034 | A1 | 10/2000 |
| WO | 2001028459 | A1 | 4/2001 |
| WO | 2001035878 | A2 | 5/2001 |
| WO | 2001049213 | A2 | 7/2001 |
| WO | 2001054624 | A1 | 8/2001 |
| WO | 2001054625 | A1 | 8/2001 |
| WO | 2001062189 | A1 | 8/2001 |
| WO | 2001064137 | A1 | 9/2001 |
| WO | 2001076510 | A2 | 10/2001 |
| WO | 2002036048 | A1 | 5/2002 |
| WO | WO-2002041789 | A2 | 5/2002 |
| WO | 2003047468 | A1 | 6/2003 |
| WO | 2003092554 | A1 | 11/2003 |
| WO | 2004030569 | A2 | 4/2004 |
| WO | 2005011534 | A1 | 2/2005 |
| WO | 2005034812 | A1 | 4/2005 |
| WO | WO-2005062980 | A2 | 7/2005 |
| WO | 2005087140 | A1 | 9/2005 |
| WO | 2005102015 | A2 | 11/2005 |
| WO | 2006014233 | A2 | 2/2006 |
| WO | 2006034008 | A2 | 3/2006 |
| WO | 2006085225 | A1 | 8/2006 |
| WO | 2006108090 | A2 | 10/2006 |
| WO | 2006111391 | A1 | 10/2006 |
| WO | 2006138173 | A2 | 12/2006 |
| WO | 2007025028 | A1 | 3/2007 |
| WO | 2008005405 | A2 | 1/2008 |
| WO | 2008035337 | A2 | 3/2008 |
| WO | 2008125153 | A1 | 10/2008 |
| WO | 2008147964 | A1 | 12/2008 |
| WO | 2008150529 | A1 | 12/2008 |
| WO | 2009024859 | A2 | 2/2009 |
| WO | 2009026563 | A2 | 2/2009 |
| WO | 2009042196 | A2 | 4/2009 |
| WO | 2009091509 | A1 | 7/2009 |
| WO | 2009094500 | A1 | 7/2009 |
| WO | 2010005524 | A2 | 1/2010 |
| WO | 2010008549 | A1 | 1/2010 |
| WO | 2010121076 | A2 | 10/2010 |
| WO | 2011002996 | A2 | 1/2011 |
| WO | 2011081997 | A1 | 7/2011 |
| WO | 2012032187 | A1 | 3/2012 |
| WO | 2012095455 | A2 | 7/2012 |
| WO | 2013028387 | A2 | 2/2013 |
| WO | 2013106585 | A1 | 7/2013 |
| WO | 2014018432 | A2 | 1/2014 |
| WO | 2014079291 | A1 | 5/2014 |
| WO | 2014145338 | A1 | 9/2014 |
| WO | 2014149865 | A1 | 9/2014 |
| WO | 2014163706 | A1 | 10/2014 |
| WO | 2014194178 | A1 | 12/2014 |
| WO | 2015057407 | A1 | 4/2015 |
| WO | 2015077274 | A1 | 5/2015 |
| WO | 2016016899 | A1 | 2/2016 |
| WO | 2017035487 | A1 | 3/2017 |
| WO | 2018213209 | A1 | 11/2018 |
| WO | 2022002054 | A1 | 1/2022 |
| WO | 2023006048 | A1 | 2/2023 |
| WO | 2023076103 | A1 | 5/2023 |
| WO | 2023081236 | A1 | 5/2023 |
| WO | 2023091769 | A1 | 5/2023 |
| WO | 2023096804 | A1 | 6/2023 |
| WO | 2023154250 | A1 | 8/2023 |
| WO | 2023196150 | A1 | 10/2023 |
| WO | 2023244454 | A1 | 12/2023 |
| WO | 2023244767 | A1 | 12/2023 |
| WO | 2023250114 | A1 | 12/2023 |
| WO | 2024001789 | A1 | 1/2024 |
| WO | 2024003620 | A1 | 1/2024 |
| WO | 2024007575 | A1 | 1/2024 |
| WO | 2024009540 | A1 | 1/2024 |
| WO | 2024010739 | A1 | 1/2024 |
| WO | 2024030520 | A1 | 2/2024 |

OTHER PUBLICATIONS

Andersen, Henning Rud, "History of Percutaneous Aortic Valve Prosthesis," Herz 34 2009 Nr. 5, Urban&Vogel, pp. 343-346, Skejby University Hospital Department of Cardiology, Aarhus, Denmark.

Dotter, M.D., Charles T., "Transluminal Treatment of Arteriosclerotic Obstruction," University of Oregon's Minthorn Memorial Laboratory for Cardiovascular Research through Radiology, Circulation, vol. XXX, Nov. 1964, pp. 654-670.

Inoue, M.D., Kanji, et al., "Clinical Application of Transvenous Mitral Commissurotomy by a New Balloon Catheter," The Journal of Thoracic and Cardiovascular Surgery 87:394-402, 1984.

Pavcnik, M.D., Ph.D., Dusan, et al. "Development and Initial Experimental Evaluation of a Prosthetic Aortic Valve for Transcatheter Placement," Cardiovascular Radiology 1992; 183:151-154.

Rashkind, M.D., William J., "Historical Aspects of Interventional Cardiology: Past, Present, Future," Texas Heart Institute Journal, Interventional Cardiology, pp. 363-367.

Rösch, M.D., Josef, "The Birth, Early Years and Future of Interventional Radiology," J Vasc Interv Radiol 2003; 14:841-853.

Ross, F.R.C.S., D.N., "Aortic Valve Surgery," Guy's Hospital, London, pp. 192-197, approximately 1968.

Sabbah, Ph.D., Hani N., et al., "Mechanical Factors in the Degeneration of Porcine Bioprosthetic Valves: An Overview," Journal of Cardiac Surgery, vol. 4, No. 4, pp. 302-309, Dec. 1989; ISSN 0886-0440.

Wheatley, M.D., David J., "Valve Prostheses," Rob&Smith's Operative Surgery, Fourth Edition, pp. 415-424, Butterworths 1986.

Bavaria, Joseph E. M.D. et al.: "Transcatheter Mitral Valve Implantation: The Future Gold Standard for MR?".

Backer, Ole De, MD, et al., "Percutaneous Transcatheter Mitral Valve Replacement—An Overview of Devices in Preclinical and Early Clinical Evaluation," Contemporary Reviews in Interventional Cardiology, Circ Cardiovasc Interv. 2014;7:400-409.

Bavaria, Joseph E. M.D.: "CardiAQ Valve Technologies: Transcatheter Mitral Valve Implantation," Sep. 21, 2009.

(56) References Cited

OTHER PUBLICATIONS

Berreklouw, Eric, PhD, et al., "Sutureless Mitral Valve Replacement With Bioprostheses and Nitinol Attachment Rings: Feasibility In Acute Pig Experiments," The Journal of Thoracic and Cardiovascular Surgery, vol. 142, No. 2, Aug. 2011 in 7 pages.

Boudjemline, Younes, et al., "Steps Toward the Percutaneous Replacement of Atrioventricular Valves," JACC, vol. 46, No. 2, Jul. 19, 2005:360-5.

CardiAQ Valve Technologies, "Innovations in Heart Valve Therapy," In3 San Francisco, Jun. 18, 2008, PowerPoint presentation in 19 slides.

Chiam, Paul T.L., et al., "Percutaneous Transcatheter Aortic Valve Implantation: Assessing Results, Judging Outcomes, and Planning Trials," JACC: Cardiovascular Interventions, The American College of Cardiology Foundation, vol. 1, No. 4, Aug. 2008:341-50.

Condado, Jose Antonio, et al., "Percutaneous Treatment of Heart Valves," Rev Esp Cardio. 2006;59(12):1225-31.

Feldman, Ted, MD. "Prospects for Percutaneous Valve Therapies," Circulation 2007;116:2866-2877.

Fitzgerald, Peter J. M.D., "Tomorrow's Technology: Percutaneous Mitral Valve Replacement, Chordal Shortening, and Beyond," Transcatheter Valve Therapies (TVT) Conference. Seattle, WA.

Fornell, Dave, "Transcatheter Mitral Valve replacement Devices in Development," Diagnostic and Interventional Cardiology, Dec. 30, 2014, p. 3, <http://www.dicardiology.com/article/transcatheter-mitral-valve-replacement-devices-development>.

Grube, E. et al., "Percutaneous aortic valve replacement for severe aortic stenosis in high-risk patients using the second- and current third-generation self-expanding CoreValve prosthesis: device success and 30-day clinical outcome." J Am Coll Cardiol. Jul. 3, 2007;50(1):69-76. Epub Jun. 6, 2007.

Karimi, Houshang, et al., "Percutaneous Valve Therapies," SIS 2007 Yearbook, Chapter 11, pp. 1-11.

Kronemyer, Bob, "CardiAQ Valve Technologies: Percutaneous Mitral Valve Replacement," Start Up—Windhover Review of Emerging Medical Ventures, vol. 14, Issue No. 6, Jun. 2009, pp. 48-49.

Leon, Martin B., et al., "Transcatheter Aortic Valve Replacement in Patients with Critical Aortic Stenosis: Rationale, Device Descriptions, Early Clinical Experiences, and Perspectives," Semin. Thorac. Cardiovasc. Surg. 18:165-174, 2006 in 10 pages.

Lutter, Georg, et al., "Off-Pump Transapical Mitral Valve Replacement," European Journal of Cardio-thoracic Surgery 36 (2009) 124-128.

Ma, Liang, et al., "'Double-Crowned Valved Stents For Off-Pump Mitral Valve Replacement," European Journal of Cardio-thoracic Surgery 28 (2005) 194-199.

Mack, Michael, M.D., "Antegrade Transcatheter Mitral valve Implantation: A Short-term Experience in Swine Model,".

Mack, Michael, M.D., "Antegrade Transcatheter Mitral valve Implantation: On-Going Experience in Swine Model,".

Ostrovsky, Gene, "Transcatheter Mitral Valve Implantation Technology from CardiAQ," medGadget, Jan. 15, 2010, available at: http://www.medgadget.com/2010/01/transcatheter_mitral_valve_implantation_technology_from_cardiaq.html.

Preston-Maher, Georgia L., et al., "A Technical Review of Minimally Invasive Mitral Valve Replacements," Cardiovascular Engineering and Technology, vol. 6, No. 2, Jun. 2015, pp. 174-184.

Quadri, Arshad M.D., "Transcatheter Mitral Valve Implantation (TMVI) (An Acute In Vivo Study),".

Ratz, J. Brent, "LSI EMT Spotlight," May 15, 2009.

Ratz, J. Brent et al., "Any experiences making an expandable stent frame?" Arch-Pub.com, Architecture Forums: Modeling, Multiple forum postings from Feb. 3, 2009 to Feb. 4, 2009, http://www.arch-pub.com.

Ratz, J. Brent, "In3 Company Overview," Jun. 24, 2009.

Ruiz, Carlos E., "Overview of Novel Transcatheter Valve Technologies,".

Spillner, J et al., "New Sutureless 'Atrial- Mitral-Valve Prosthesis' For Minimally Invasive Mitral Valve Therapy," Textile Research Journal, 2010, in 7 pages.

Sondergaard, Lars, et al., "Transcatheter Mitral Valve Implantation: CardiAQ™," TCT 2013.

Sondergaard, Lars, et al., "Transcatheter Mitral Valve Implantation: CardiAQ™," EuroPCR 2013.

Sondergaard, Lars, "CardiAQ TMVR FIH—Generation 2," TVT symposium.

Treede et al.: "Transapical transcatheter aortic valve implantation using the JenaValve™ system: acute and 30-day results of the multicentre CE-mark study." http://ejcts.oxfordjournals.org/content/41/6/e131.long. Apr. 16, 2012.

Taramasso et al.: "New devices for TAVI: technologies and initial clinical experiences" http://www.nature.com/nrcardio/journal/v11/n3/full/nrcardio.2013.221.html?message-global=remove#access. Jan. 21, 2014.

Webb, John G., et al., "Transcatheter Aortic Valve Implantation: The Evolution Of Prostheses, Delivery Systems And Approaches," Archives of Cardiovascular Disease (2012) 105, 153-159.

Wayback Machine, Cleveland Clinic Lerner Research Institute, Transcatheter Mitral Stent/Valve Prosthetic, https://web.archive.org/web/20130831094624/http://mds.clevelandclinic.org/Portfolio.aspx?n=331, indicated as archived on Aug. 31, 2013.

"CardiAQ Valve Technologies, Percutaneous Mitral Valve Replacement, Company Overview," at TVT on Jun. 25, 2009.

BioSpace, "CardiAQ Valve Technologies (CVT) Reports First-In-Human Percutaneous Transfemoral, Transseptal Implantation With Its Second Generation Transcatheter Bioprosthetic Mitral Heart Valve," Jun. 23, 2015, p. 1, http://www.biospace.com/News/cardiaq-valve-technologies-cvt-reports-first- in/382370.

BioSpace, "CardiAQ Valve Technologies (CVT) Reports Cardiovascular Medicine Milestone: First-In-Humannonsurgical Percutaneous Implantation of a Bioprosthetic Mitral Heart Valve," Jun. 14, 2012, p. 1, http://www.biospace.com/News/cardiaq-valve-technologies-cvt-reports/263900.

Neovasc corporate presentation, Oct. 2009, available at http://www.neovasc.com/investors/documents/Neovasc-Corporate-Presentation-Oct. 2009.pdf.

Herrmann, Howard C., M.D., "Advances in Transseptal Transcatheter Mitral Valve Replacement," Cardiovascular Research Foundation, tct, Sep. 21-25, 2018, 10 Pages, San Diego, California.

Neale, Todd, "Flushing TAVI Valves With Carbon Dioxide May Protect Against Brain Injury", News Conference News, EuroPCR 2023, TCTMD, May 16, 2023, Paris France.

Transcatheter Aortic Valve Delivery Catheter System Compression Loading System, Medtronic CoreValveSystem, Medtronic Inc, 2014, 61 pages, Santa Ana, California.

* cited by examiner

TEXTILES FOR IMPLANTATION

CROSS-REFERENCE TO RELATED APPLICATIONS

This application is a continuation of International Application No. PCT/US2022/025593, filed Apr. 20, 2022, which designates the United States and was published in English by the International Bureau on Oct. 27, 2022 as WO2022/226090, which claims the benefit of U.S. Provisional Application No. 63/177,700, filed Apr. 21, 2021; the entirety of each of which is hereby incorporated by reference.

BACKGROUND

Field

Certain examples disclosed herein relate generally to textiles for implantation within a portion of a patient's body.

Background

Human heart valves, which include the aortic, pulmonary, mitral and tricuspid valves, function essentially as one-way valves operating in synchronization with the pumping heart. The valves allow blood to flow downstream, but block blood from flowing upstream. Diseased heart valves exhibit impairments such as narrowing of the valve or regurgitation, which inhibit the valves' ability to control blood flow. Such impairments reduce the heart's blood-pumping efficiency and can be a debilitating and life threatening condition. For example, valve insufficiency can lead to conditions such as heart hypertrophy and dilation of the ventricle. Thus, extensive efforts have been made to develop methods and apparatuses to repair or replace impaired heart valves.

Prostheses exist to correct problems associated with impaired heart valves. For example, mechanical and tissue-based heart valve prostheses can be used to replace impaired native heart valves. More recently, substantial effort has been dedicated to developing replacement heart valves, particularly tissue-based replacement heart valves that can be delivered with less trauma to the patient than through open heart surgery. Replacement valves are being designed to be delivered through minimally invasive procedures and even percutaneous procedures.

These replacement valves may include compliant materials positioned on the valve. For example, foams or other compressible material may be utilized that cushion the valve from portions of the patient's body during deployment. Such foams however, may be difficult to manufacture and affix to a replacement valve. Improvements in textiles may be desired to provide compliant materials on valves, and also for other implantation purposes within a patient's body.

SUMMARY

Examples of textiles disclosed herein may include a fabric having a honeycomb weave pattern formed by biocompatible fibers. The fabric in examples may be heat treated to increase a thickness of the fabric. The fabric may be compliant, and compressible, to allow for cushioning within a patient's body. For example, the fabric may be applied to a prosthetic valve to cushion a portion of the prosthetic valve. The fabric may comprise a pad that is applied to one or more anchors of the prosthetic valve to cushion the anchor relative to structure of the native valve, or other structure within a patient's heart. In examples, the fabric may be applied to other portions of a prosthetic valve including a skirt of the prosthetic valve. In examples, the fabric may reduce the deployment force required to deploy a prosthetic valve or other form of implant, due to the compressibility of the fabric.

Examples herein may include a textile for implantation within a portion of a patient's body. The textile may comprise a fabric having a honeycomb weave pattern formed by biocompatible fibers, and heat treated to increase a thickness of the fabric.

Examples herein may include a prosthetic valve configured to be deployed to a native valve of a heart. The prosthetic valve may include a plurality of prosthetic valve leaflets, and one or more anchors coupled to the plurality of prosthetic valve leaflets and each configured to anchor to a portion of the heart. The prosthetic valve may include one or more pads coupled to the one or more anchors, each of the one or more pads including a fabric having a honeycomb weave pattern.

Examples herein may include a method of fabricating a textile for implantation within a portion of a patient's body. The method may include providing a fabric having a honeycomb weave pattern formed by biocompatible fibers. The method may include heat treating the fabric to increase a thickness of the fabric.

Examples herein may include a method comprising deploying a prosthetic valve to a native valve of a patient's heart. The prosthetic valve may include a plurality of prosthetic valve leaflets, one or more anchors coupled to the plurality of prosthetic valve leaflets and each configured to anchor to a portion of the patient's heart, and one or more pads coupled to the one or more anchors, each of the one or more pads including a fabric having a honeycomb weave pattern.

Examples herein may include a prosthetic valve configured to be deployed to a native valve of a heart. The prosthetic valve may include a plurality of prosthetic valve leaflets. The prosthetic valve may include a valve body supporting the plurality of prosthetic valve leaflets and including a skirt, at least a portion of the skirt having a honeycomb weave pattern.

Examples herein may include a prosthetic valve configured to be deployed to a native valve of a heart. The prosthetic valve may include a plurality of prosthetic valve leaflets. The prosthetic valve may include a valve body supporting the plurality of prosthetic valve leaflets and including a skirt, at least a portion of the skirt including one or more friction bodies for providing friction with a portion of the heart.

Examples herein may include a method comprising deploying a prosthetic valve to a native valve of a patient's heart. The prosthetic valve may include a plurality of prosthetic valve leaflets. The prosthetic valve may include a valve body supporting the plurality of prosthetic valve leaflets and including a skirt, at least a portion of the skirt having a honeycomb weave pattern.

Examples herein may include a method comprising deploying a prosthetic valve to a native valve of a patient's heart. The prosthetic valve may include a plurality of prosthetic valve leaflets. The prosthetic valve may include a valve body supporting the plurality of prosthetic valve leaflets and including a skirt, at least a portion of the skirt including one or more friction bodies for providing friction with a portion of the heart.

BRIEF DESCRIPTION OF THE DRAWINGS

Features and advantages of the systems, apparatuses, and methods as disclosed herein will become appreciated as the same become better understood with reference to the specification, claims, and appended drawings wherein:

DETAILED DESCRIPTION

Figure 1:
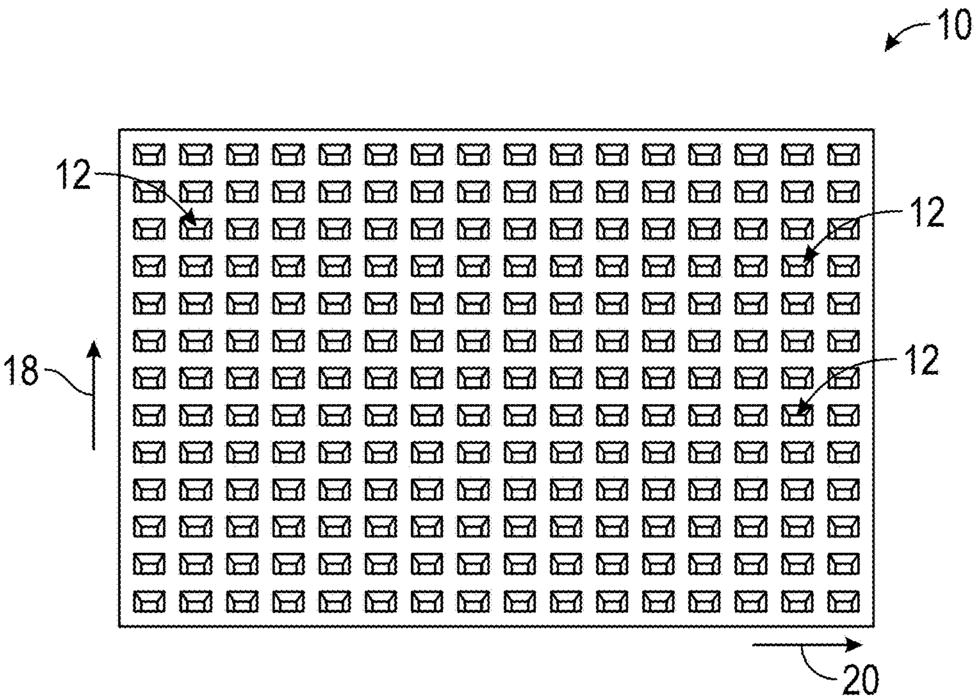
FIG. 1 illustrates a view of a surface of a fabric according to an example of the present disclosure.

FIG. 1 illustrates an example of a textile for implantation within a portion of a patient's body. The textile comprises a fabric 10. In examples, the fabric 10 may have a honeycomb weave pattern. The honeycomb weave pattern may be formed by biocompatible fibers.

The honeycomb weave pattern may comprise a repeating pattern of cells 12 that repeats along a surface of the fabric 10. The cells 12 may have portions with varied heights, with a central portion 14 (represented in FIG. 3) having a lower height than an outer portion 16 (represented in FIG. 3). The central portion 14 may form a pit that is surrounded by the outer portion 16. The outer portion 16 may comprise raised walls that surround the pit of the central portion 14. Each cell 12 may include a pit surrounded by walls. In examples, the pits may have a variety of shapes, including an inverted pyramidal shape or a domed shape or another shape as desired. The cells 12 may have a square or rectangular shape as shown in FIGS. 1-3 or may have another shape as desired.

The cells 12 may repeat along a length 18 and a width 20 of the fabric 10. The cells 12 may be adjacent to each other, with the outer portion 16 of each cell 12 being adjacent to an outer portion 16 of an adjacent cell as shown in FIG. 3 for example. As shown in FIGS. 1 and 3, the cells may be aligned with each other along the length 18 (in columns) and the width 20 (in rows) in examples, or other patterns may be utilized as desired. For example, the cells 12 may be aligned in a diagonal direction, or another pattern in examples as desired. The cells 12 may repeat with irregular configurations, for example, one cell 12 may have a square configuration as shown in FIG. 3 for example, and an adjacent cell may have another configuration in examples.

The honeycomb weave pattern may be formed by warp and weft threads interlaced and floating in a way that creates the outer portions 16 (e.g., the walls) and the central portion 14 (e.g., the pits) in the fabric 10 in a regular pattern. In examples, the warp and weft floats may be arranged around a plain weave center, and may be woven partly on tabby areas surrounded by ridges of long floats. Other configurations may be utilized as desired.

Figure 2:
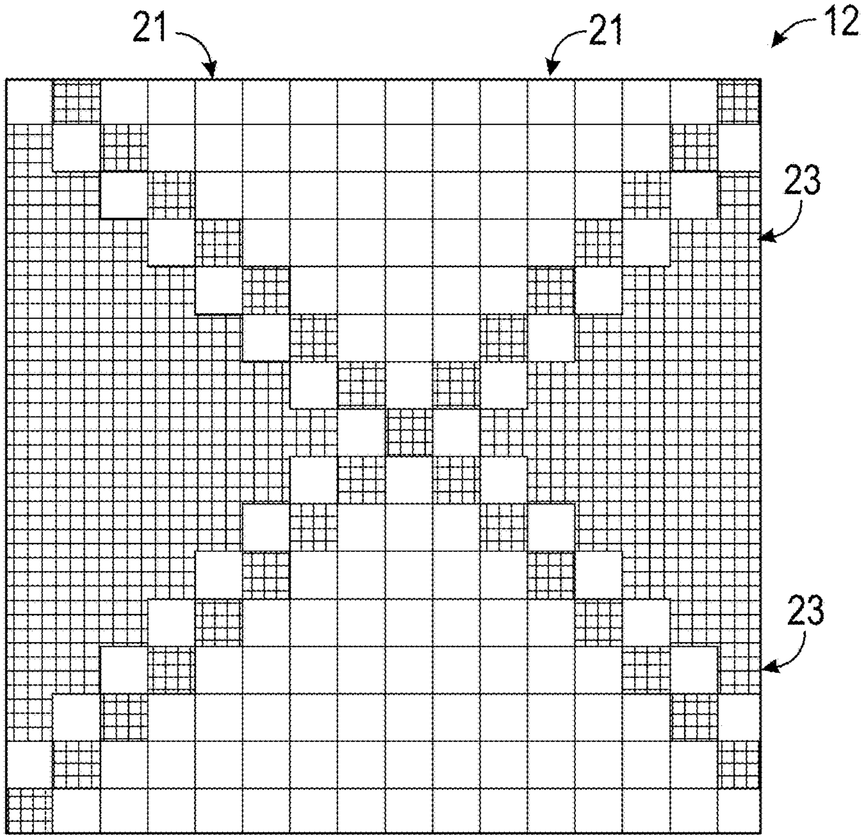
FIG. 2 illustrates a schematic of a weave pattern of a fabric according to an example of the present disclosure.
Figure 3:
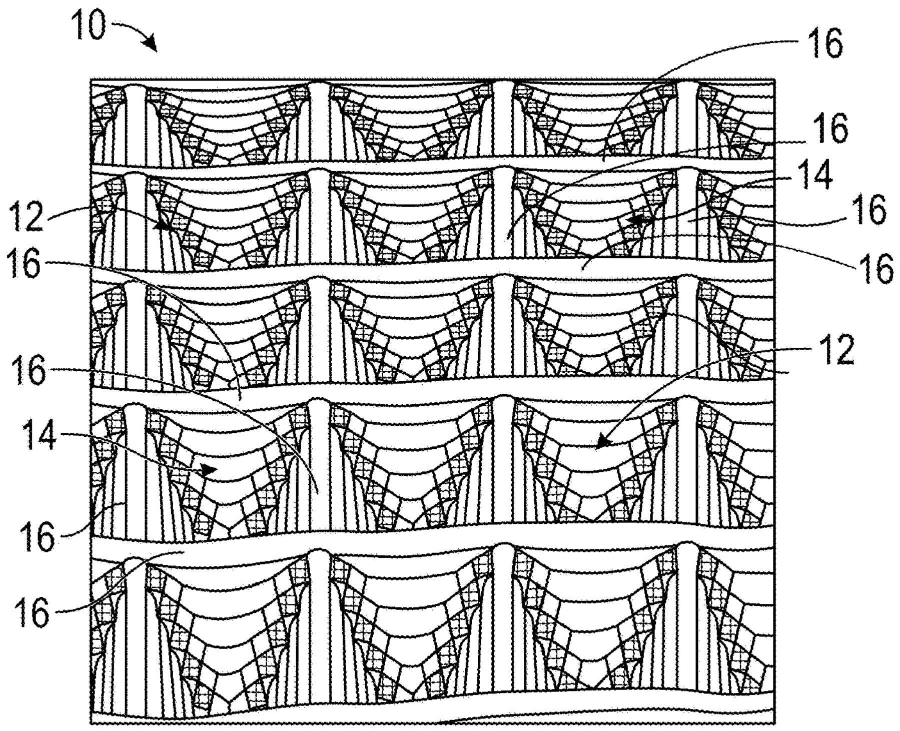
FIG. 3 illustrates a perspective view of a representation of a surface of a weave pattern of a fabric.

FIG. 2, for example, illustrates a pattern of a honeycomb weave pattern according to an example herein. The pattern of a single cell 12 is shown. The pattern may comprise a sixteen end honeycomb repeat as shown in FIG. 2. Sixteen warp fibers 21 and sixteen weft fibers 23 are represented in FIG. 2. The darkened squares shown in FIG. 2 comprise a warp float and the white squares shown in FIG. 2 comprise a weft float. The part of a warp fiber underneath a weft float is a warp float. The two layers of floats form a closed internal space (i.e., the central portions 14 marked in FIG. 3).

In examples, other configurations of weaves may be utilized. For example, between a four end honeycomb repeat to a thirty-two end honeycomb may be utilized in examples. A greater configuration than a thirty-two end honeycomb repeat may be utilized in examples. A range between a four end honeycomb repeat and a sixteen end honeycomb repeat may be utilized in examples. A range between a sixteen end honeycomb repeat and a thirty-two end honeycomb repeat may be utilized in examples. Other configurations may be utilized as desired.

The honeycomb weave pattern may include honeycomb weave derivatives such as a modified honeycomb weave pattern in examples, or other derivatives as desired.

FIG. 3 illustrates a perspective view of a representation of a honeycomb weave pattern according to examples herein. Certain details of the weave pattern may be excluded from view, including the details of a particular overlay of fibers as shown in FIG. 2 for example.

The repeating pattern of cells 12 is visible, including the pits of the central portion 14 surrounded by the walls of the outer portion 16 for each cell 12. A variation in height between the pits of the central portion 14 and the walls of the outer portion 16 is visible.

The fabric 10 may comprise a single layer of fabric, having a length, a width, and a thickness.

The fibers utilized to form the honeycomb weave pattern, in examples, may each extend continuously from a first end of the fabric to a second opposite end of the fabric. Thus, the warp fibers 21 shown in FIG. 2, for example, may extend continuously from an upper end of the fabric to a lower end of the fabric. The weft fibers 23 shown in FIG. 2, for example, may extend continuously from a right end of the fabric to a left end of the fabric. The continuous extent of the fibers may reduce the possibility of a fiber becoming loose within the patient's body. Thus, the continuous extent may improve the biocompatibility of the fabric 10 for the patient's body as a whole.

The fibers utilized to form the honeycomb weave pattern may be biocompatible. The fibers, for example, may comprise biocompatible polymers, which may be bio-resorbable or non-resorbable. The bioresorbable polymers may comprise one or more of polyglycolic acid (PGA), polylactic acid (PLA), polycaprolactone (PCL), polylactide glycolide copolymers (PLGA), or other bioresorbable polymers. The bioresorbable polymers for example, may comprise fibers that are absorbed by the body within 2 to 3 months or a different duration as desired. Non-resorbable biocompatible polymers may comprise one or more of polyester (PET), polypropylene (PP), nylon, ultra high molecular weight polyethylene (UHMWPE), polytetrafluoroethylene (PTFE), expanded polytetrafluoroethylene (ePTFE), polyetheretherketone (PEEK), or other materials as desired.

The biocompatible fibers may comprise one or more of a biocompatible textured multifilament yarn, a biocompatible textured high shrinkage multifilament yarn, a biocompatible flat multifilament yarn, a twisted multifilament yarn, or other materials as desired. The biocompatible fibers are preferably configured to be unitary, and lack loose threads that may come loose within a patient's body which may be undesirable.

In examples, each biocompatible fiber may have a weight of between 10 Denier to 400 Denier. Denier (D) is a unit of measure for linear mass of each fiber comprising the mass in grams per 9000 meters of the fiber. In examples, each biocompatible fiber may have a weight between 20 D to 100 D. In examples, each biocompatible fiber may have a weight of about 70 D. Other weights of fibers and ranges of weights of fibers may be utilized in examples as desired.

Figure 4:
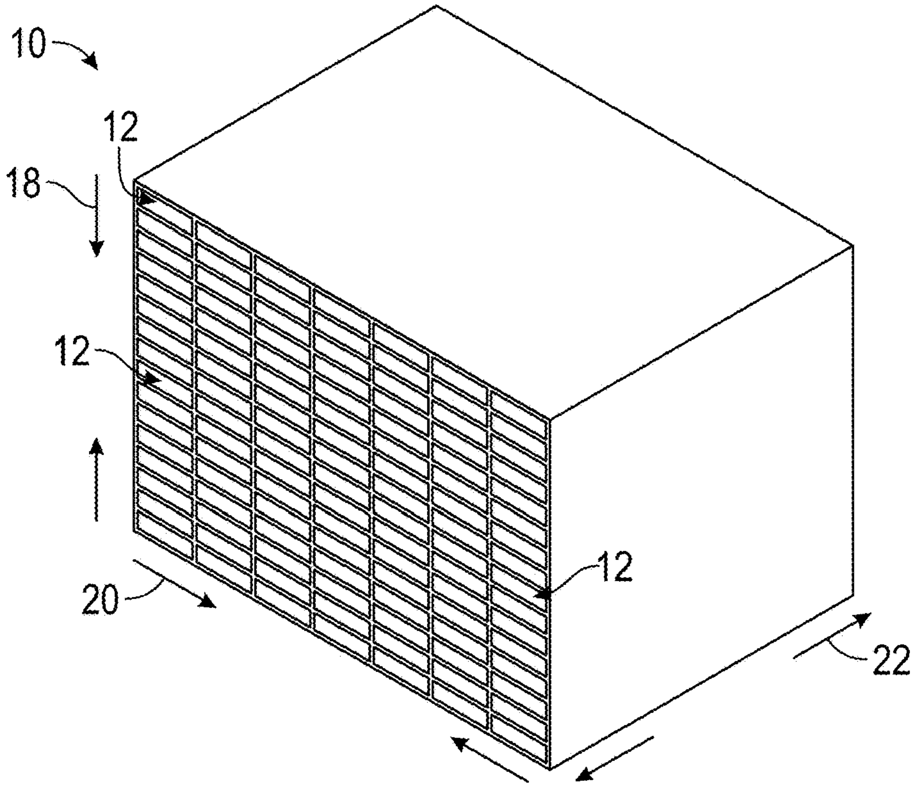
FIG. 4 illustrates a schematic view of a thickness of a fabric increasing.

The biocompatible fibers may be configured to shrink upon the fabric 10 being heat treated. The shrinkage of the biocompatible fibers may result in an increased thickness 22 of the fabric 10. FIG. 4, for example, illustrates an increased thickness 22 resulting from the heat treatment applied to the fabric 10. The heat treatment, for example, may comprise placing the fabric 10 at a high temperature, in an oven for example, for a desired duration. The duration may be 10 minutes for example, or a greater or lesser duration based on the desired result. The heat treatment may cause the biocompatible fibers to shrink.

Figure 5:
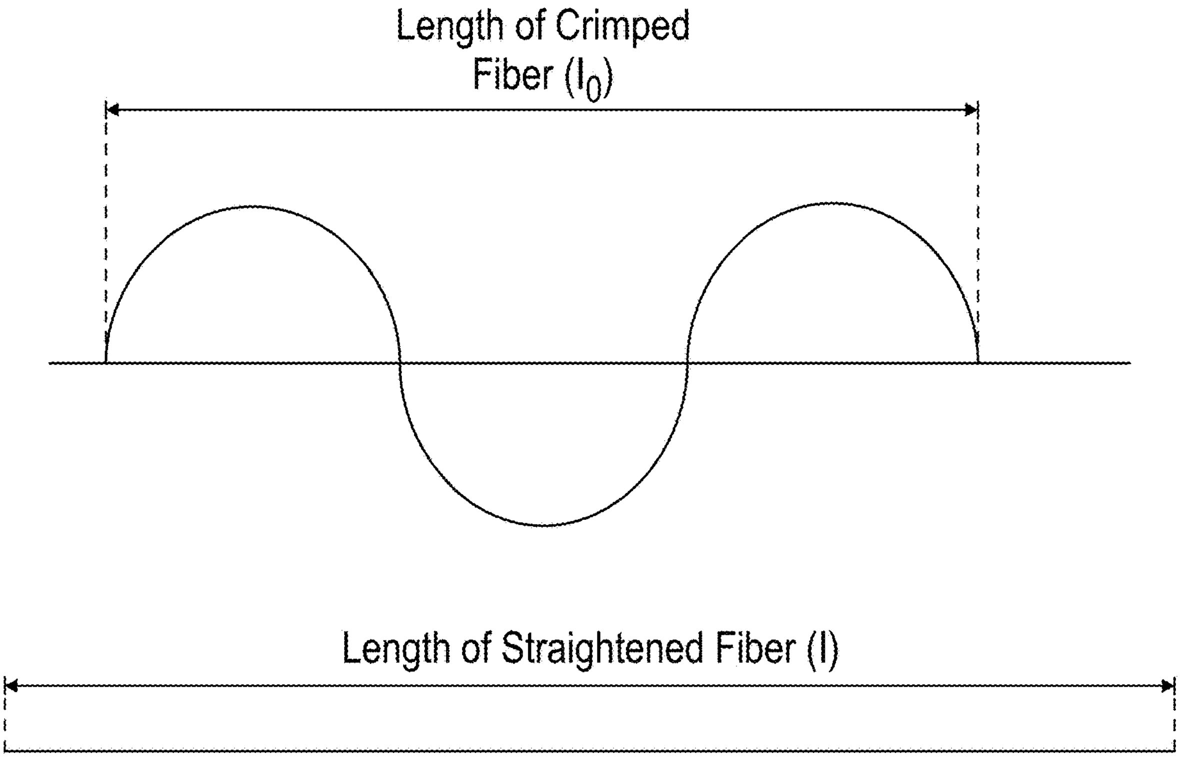
FIG. 5 illustrates a schematic of a representation of fiber crimp.

The biocompatible fibers may be configured to shrink due to a crimp of the biocompatible fibers increasing. The biocompatible fibers may be wavy, particularly following the heat treatment, and the crimp being the proportion of the difference between the length of a straightened fiber (l) and the length of the crimped fiber ($l_0$) relative to the length of the crimped fiber ($l_0$). FIG. 5, for example, illustrates the relative measures of the length of the straightened fiber (l) and the length of the crimped fiber ($l_0$). The crimp is given by:

$$\text{Crimp }(\%)=((l-l_0)/l_0)\times 100$$

Crimp in a textile fiber is the undulations or succession of waves or curls in the fiber strand. Crimp in a fiber is thus considered as the degree of deviation from linearity of a non straight fiber. The biocompatible fibers may be straight or wavy prior to heat treatment, with the heat treatment increasing a crimp of the biocompatible fibers.

The shrinkage of the biocompatible fibers may cause the thickness 22 of the fabric to increase and the length 18 and the width 20 to decrease as represented in FIG. 4. As such, the thickness or height of each cell 12 may increase upon the fabric 10 being heat treated.

Figure 6A:
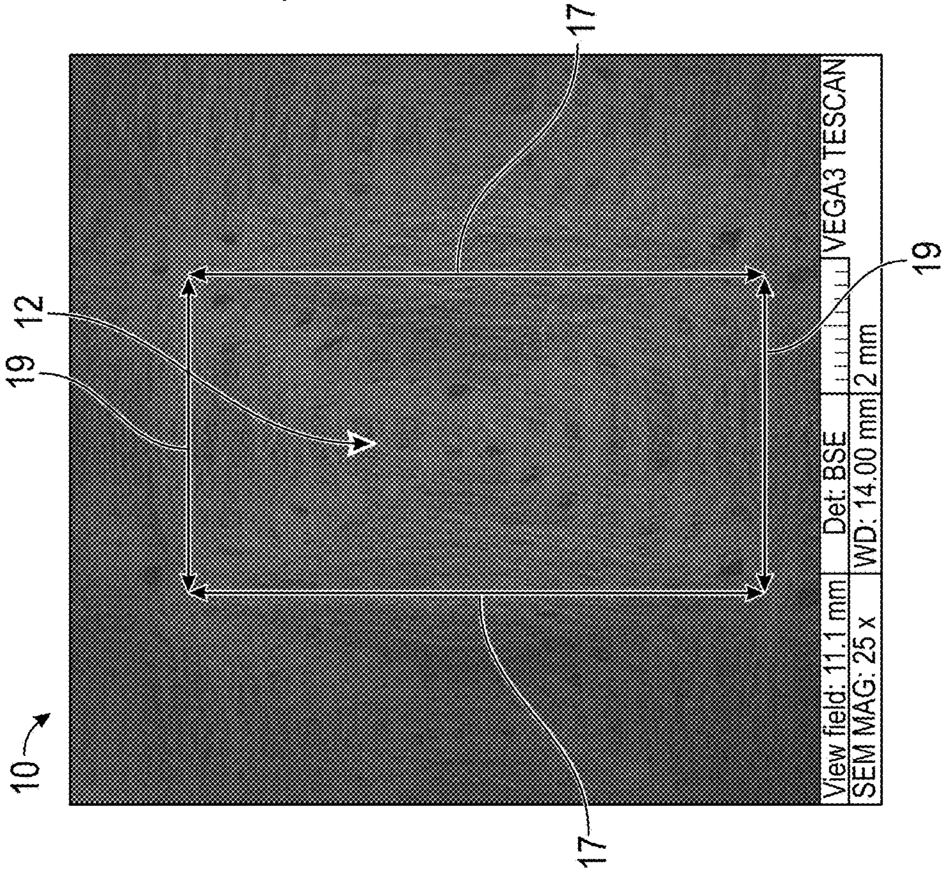
FIG. 6A is a photograph of a fabric prior to a heat treatment according to an example of the present disclosure.
Figure 6B:
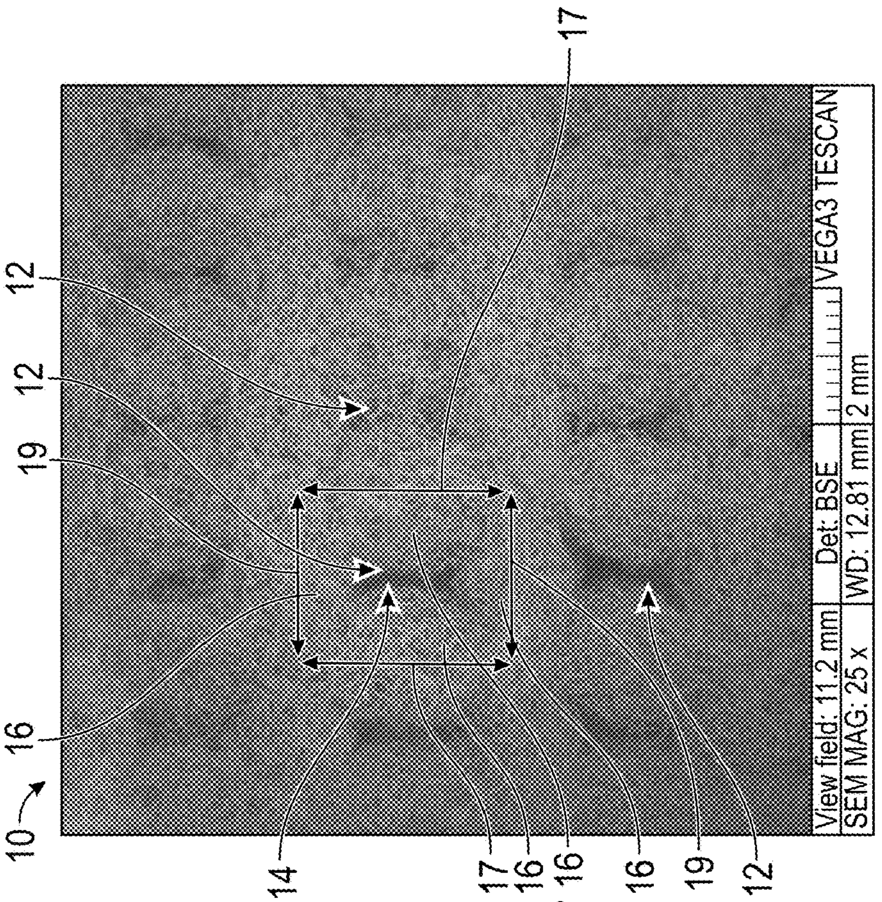
FIG. 6B is a photograph of the fabric shown in FIG. 6A following a heat treatment according to an example of the present disclosure.

FIG. 6A, for example, illustrates a surface of the fabric 10 prior to heat treatment. A length 17 and width 19 of a cell 12 is marked. FIG. 6B illustrates the fabric 10 shown in FIG. 6A following heat treatment, with the length 17 and width 19 of the cell 12 and the fabric having decreased. The crimp of the biocompatible fibers increases. The thickness of the fabric has increased.

Various increases in thickness may result. Referring to FIG. 4, in examples, an increase in thickness 22 of the fabric 10 may be more than 100 percent due to the heat treatment. In examples, an increase in thickness 22 of the fabric 10 may be more than 500 percent due to the heat treatment. In examples, an increase in thickness 22 of the fabric 10 may be more than 1,000 percent due to the heat treatment. In examples, an increase in thickness 22 of the fabric 10 may be more than 1,500 percent due to the heat treatment. In examples, an increase in thickness 22 of the fabric 10 may be more than 1,800 percent due to the heat treatment. In examples, an increase in thickness 22 of the fabric 10 may be more than 2,000 percent due to the heat treatment. In examples, an increase in thickness 22 of the fabric 10 may be more than 2,200 percent due to the heat treatment. In examples, an increase in thickness 22 of the fabric may be in a range between 100 percent and 2,500 percent. In examples, an increase in thickness 22 of the fabric 10 may be in a range between 100 percent and 1,500 percent, or between 1,500 percent and 2,500 percent. Greater or lesser increases in thickness may result as desired.

For example, in examples, a thickness prior to heat treatment may be about 1.3 millimeters and may increase to about 3.15 millimeters following heat treatment. The increase in thickness 22 accordingly may be greater than 100% due to the heat treatment and may be about 140%. Various other ranges in increase in thickness 22 may be utilized as desired. In examples, a thickness 22 prior to heat treatment may be about 0.20 millimeters and may increase to about 5 millimeters following heat treatment. The increase in thickness 22 accordingly may be greater than 2,200% due to the heat treatment and may be about 2,280%. The increase in thickness may be greater or lesser as desired.

The thickness 22 of the fabric 10 following heat treatment is greater than the thickness 22 before heat treatment. The thickness 22 may increase by the percentages disclosed herein, and may result in a thickness 22 of the fabric 10 before heat treatment of at least about 0.05 millimeters increasing as desired. A resulting thickness 22 may have a variety of sizes and the thickness of the fabric 10 may be at least 0.5 millimeters in examples. A resulting thickness 22 of the fabric 10 may be at least 2 millimeters in examples. A resulting thickness 22 of the fabric 10 may be at least 3 millimeters in examples. A resulting thickness 22 of the fabric 10 may be at least 5 millimeters in examples. A resulting thickness 22 of the fabric 10 may be at least 8 millimeters in examples. In examples, the resulting thickness 22 of the fabric 10 may be in a range between 0.5 millimeters and 10 millimeters. In examples, the resulting thickness 22 of the fabric 10 may be in a range between 0.5 millimeters and 5 millimeters. In examples, the resulting thickness 22 of the fabric 10 may be in a range between 5 millimeters and 10 millimeters. The resulting thickness 22 may be greater or lesser as desired.

The thickness 22 of the fabric 10 may increase by at least 0.2 millimeters in examples. The thickness 22 of the fabric 10 may increase by at least 1 millimeter in examples. The thickness 22 of the fabric 10 may increase by at least 4 millimeters in examples. The thickness 22 of the fabric 10 may increase by at least 8 millimeters in examples. In examples, the increase in thickness 22 of the fabric 10 may be in a range between 0.2 millimeters and 4 millimeters. In examples, the increase in thickness 22 of the fabric 10 may be in a range between 4 millimeters and 10 millimeters. The thickness 22 of the fabric 10 may increase by a lesser or greater amount in examples.

The length 18 and width 20 of the fabric 10 may decrease due to the heat treatment. In examples, the length 18 may decrease by at least 20 percent due to the heat treatment. In examples, the width 20 may decrease by at least 40 percent due to the heat treatment. In examples, a range in decrease in the length 18 of the fabric may be between 20 percent and 70 percent. In examples, a range in decrease in the width 20 of the fabric may be between 40 percent and 60 percent. Various other amounts of decrease may be utilized in examples. A length 17 and width 19 (marked in FIG. 6A) of the corresponding cells 12 may decrease by the percentages that the width 20 and length 18 of fabric 10 decrease.

A resulting increase in the volume of the fabric 10 may be at least 100 percent in examples. A resulting increase in the volume of the fabric 10 may be at least 200 percent in examples. A resulting increase in the volume of the fabric 10 may be at least 300 percent in examples. A resulting increase in the volume of the fabric 10 may be greater than 2,000 percent. In examples, a resulting increase in the volume of the fabric 10 may be greater than 10,000 percent.

In an example in which the volume of the fabric 10 increases, the density of the fabric 10 may correspondingly decrease. The density may decrease by greater than 50 percent in examples, or greater than 70 percent in examples. In examples, the density may decrease by up to 200% or a greater or lesser amount as desired. In examples, a density of the fabric in grams (g) per millimeter cubed ($mm^3$) may be about $1\times10^{-5}$ g/$mm^3$ following heat treatment. In examples, a density of the fabric may be in a range between $0.5\times10^{-5}$ g/$mm^3$ and $3\times10^{-5}$ g/$mm^3$ following heat treatment, although a greater or lesser amount may be utilized as desired.

Further, in certain examples the volume of the fabric 10 may decrease in examples. The volume may decrease based on the configuration of the ends per inch (EPI) and picks per inch (PPI) of the fabric 10 that are selected. The volume may decrease by about 10 percent, or at least about 10 percent based on the number of ends per inch (EPI) and picks per inch (PPI) of the fabric 10. A decrease in volume, however, may yet result in an increase in thickness of the fabric 10 due to the decrease in the length and width of the fabric 10.

In an example in which the volume of the fabric 10 decreases, the density of the fabric 10 may correspondingly increase. The density may increase by greater than 5 percent in examples, or greater than 10 percent in examples. In examples, the density may increase by up to 200% or a greater or lesser amount as desired. In examples, a density of the fabric in grams (g) per millimeter cubed ($mm^3$) may be about $1\times10^{-5}$ g/$mm^3$ following heat treatment. In examples, a density of the fabric may be in a range between $0.5\times10^{-5}$ g/$mm^3$ and $3\times10^{-5}$ g/$mm^3$ following heat treatment, although a greater or lesser amount may be utilized as desired.

The increased thickness 22 of the honeycomb weave pattern may enhance the cushioning properties of the fabric. The compressibility of the fabric 10 may increase, particularly along the dimension of the thickness 22. The fabric 10 after heat treatment may have a compressibility between 10 percent to 100 percent. In examples, the compressibility may be greater than 20 percent. In examples, the compressibility may be greater than 40 percent. In examples, the compressibility may be greater than 60 percent. In examples, the compressibility may be greater than 80 percent. In examples, the compressibility may be greater than 90 percent. In examples, the compressibility may be greater than 95 percent. Various amounts of compressibility may be utilized in examples.

The density of the fibers, in examples, may be between 100 to 400 ends per inch (EPI) following heat treatment. Ends per inch (EPI) is the number of warp fibers per inch of the fabric. The density may be between 100 to 300 picks per inch (PPI) following heat treatment, which is the number of weft fibers per inch of the fabric. A change in EPI may be greater than 50 percent in examples due to heat treatment. A change in EPI may be greater than 100 percent in examples due to heat treatment. For example, a fabric may have an EPI of 80 prior to heat treatment and may change to an EPI of about 175 following heat treatment, resulting in about a 120 percent change in EPI. A fabric may have an EPI of 160 prior to heat treatment and may change to an EPI of about 255 following heat treatment, resulting in about a 60 percent change in EPI. Various other amounts may be utilized as desired.

A change in PPI may be greater than 25 percent in examples due to heat treatment. A change in PPI may be greater than 80 percent in examples due to heat treatment. A change in PPI may be greater than 100 percent in examples due to heat treatment. A change in PPI may be greater than 150 percent in examples due to heat treatment. For example, a fabric may have a PPI of 40 prior to heat treatment and may change to a PPI of about 105 following heat treatment, resulting in about a 170 percent change in PPI. A fabric may have a PPI of 80 prior to heat treatment and may change to a PPI of about 160 following heat treatment, resulting in about a 100 percent change in EPI. Various other amounts may be utilized as desired.

A method as disclosed herein may include providing a fabric having a honeycomb weave pattern formed by biocompatible fibers and heat treating the fabric to increase a thickness of the fabric. The honeycomb weave pattern may be formed with the biocompatible fibers. The fabric may include the properties disclosed herein prior to heat treatment and the properties disclosed herein following heat treatment. Other methods may be utilized in examples herein. In examples, other forms of treatment may be applied to the fabric as desired.

The heat treated fabric 10 may be utilized for implant within a patient's body in a variety of manners. For example, the heat treated fabric 10 may comprise a cushion that is used to reduce the force of contact between surfaces within a patient's body. Such a cushion may be utilized with implants, to reduce the force of contact between the implant and a surface within a patient's body, although other uses may be provided as well.

FIGS. 7-12 illustrate an example in which the fabric 10 is utilized as a pad 25 (shown assembled in FIG. 8) for a portion of a prosthetic valve. The pad 25 may cushion the portion of the prosthetic valve against the native structure of the patient's body. For example, the pad 25 may be coupled to one or more anchors of the prosthetic valve to cushion the anchor against the native structure of the patient's body. In examples, the pad may reduce the deployment force required to deploy the prosthetic valve due to the compressibility of the fabric.

Figure 7:
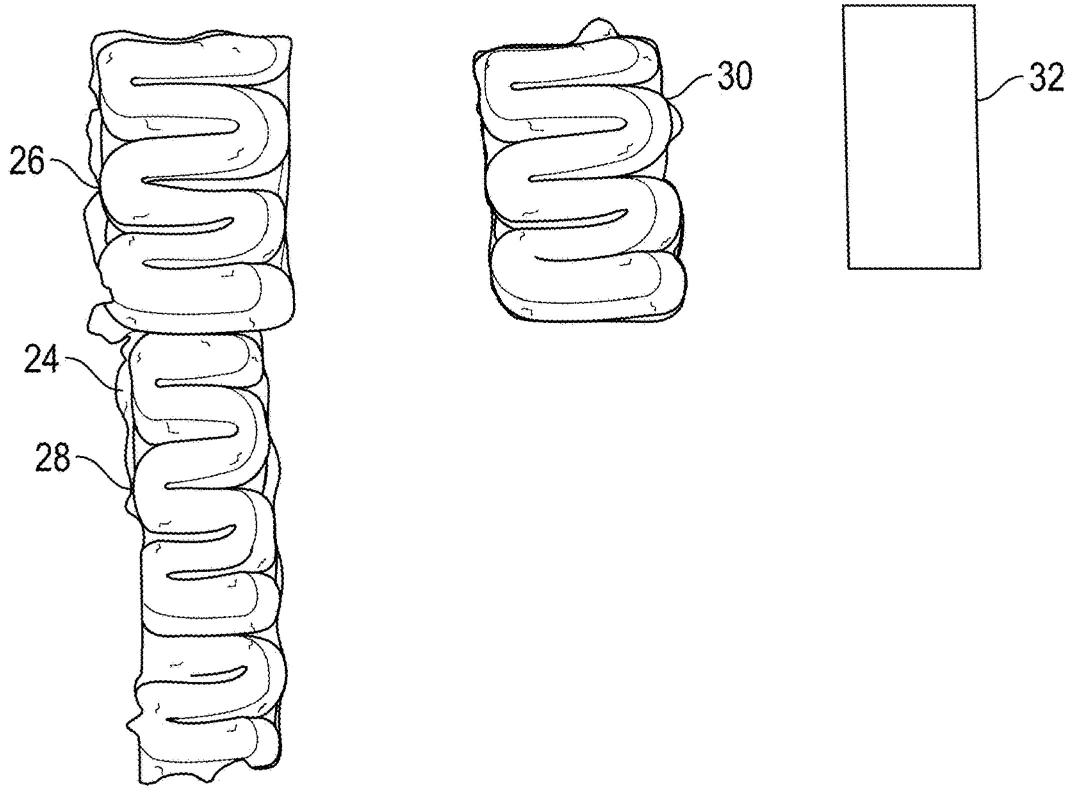
FIG. 7 illustrates a top view of layers of a pad according to an example of the present disclosure.

FIG. 7 illustrates that the pad may include a plurality of layers of the fabric 10. A section may be cut out of a sheet of the fabric 10, as shown in FIG. 1 for example, and formed into a desired shape of a pad. The section may comprise a layer 24 that has an elongate shape, and may include a head portion 26 positioned at an end of a neck portion 28. The head portion 26 may be sized to have a larger width than the neck portion 28 to account for a tip of an anchor that the head portion 26 may cover. The neck portion 28 may have an elongate shape to account for a length of an anchor that the neck portion 28 may extend along.

The pad may further include a second layer 30, which may be cut from the same sheet of fabric 10. The second layer 30 may be sized in a similar manner as the head portion 26 of the first layer 24.

In examples, the pad may further comprise a third layer 32 that may be made from the fabric 10, or may comprise another form of material in examples. For example, the third layer 32 may comprise a thin backing layer in examples.

Figure 8:
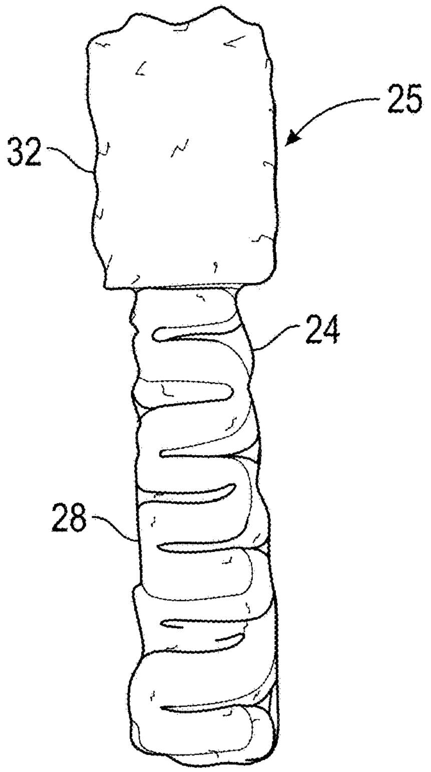
FIG. 8 illustrates a top view of an assembled pad according to an example of the present disclosure.

The layers may be stitched together or otherwise coupled together to form the pad 25 shown in FIG. 8 for example. The layers may be coupled together with the second layer 30 being positioned between the first layer 24 and the third layer 32. The second layer 30 in the assembly may comprise additional cushioning at the tip of the anchor and thus may be sized to match the size of the head portion 26.

Figure 9:
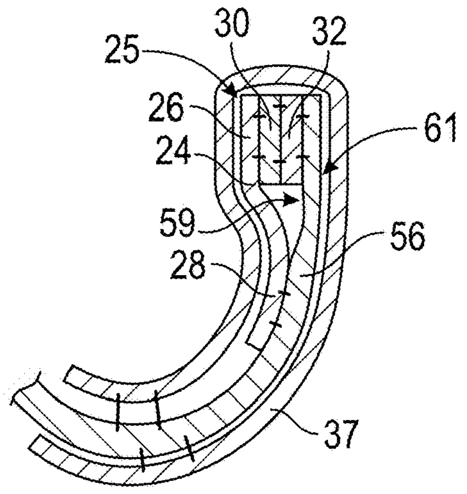
FIG. 9 illustrates a cross sectional schematic view of an assembled pad coupled to an anchor according to an example of the present disclosure.

FIG. 9, for example, illustrates the pad 25 upon an anchor arm 56 of a prosthetic valve, with the relative positions of the layers of the pad 25 shown. A sleeve 37 may extend over the pad 25 and the anchor arm 56.

Figure 10A:
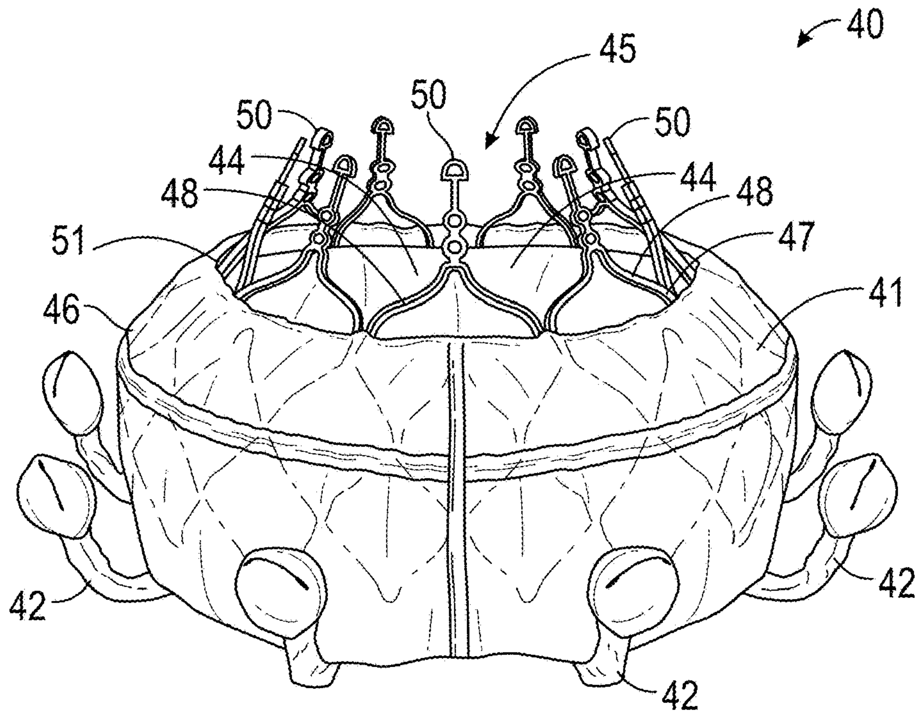
FIG. 10A illustrates a perspective view of a prosthetic valve according to an example of the present disclosure.
Figure 10B:
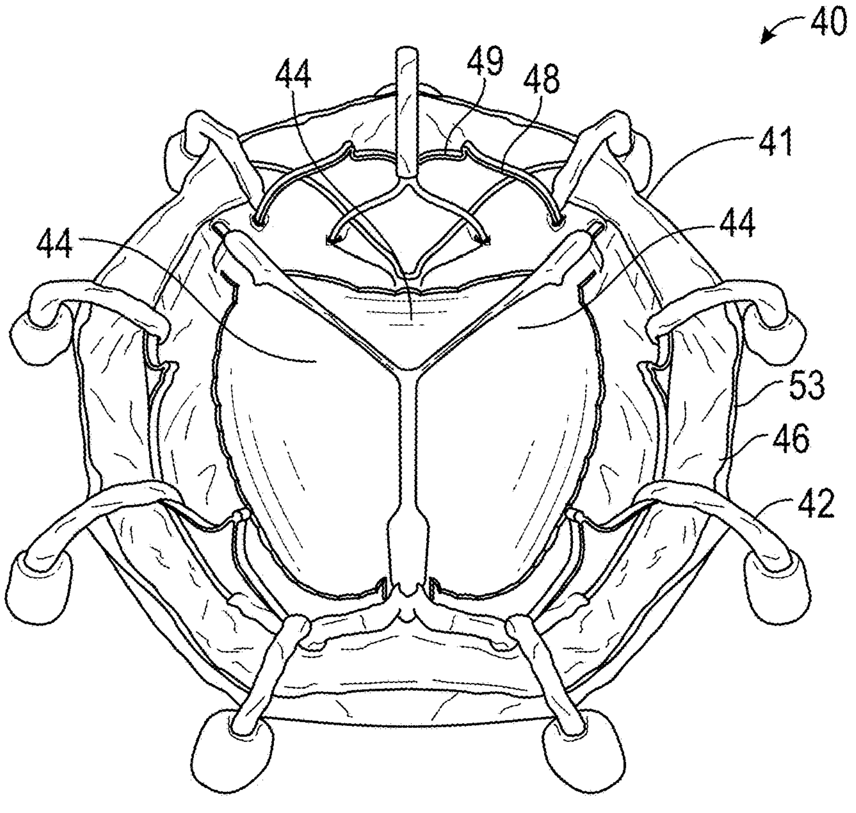
FIG. 10B illustrates a bottom view of the prosthetic valve shown in FIG. 10A according to an example of the present disclosure.

FIGS. 10A and 10B illustrate an example of a prosthetic valve 40 that may be utilized with the systems, apparatuses, and methods disclosed herein. The prosthetic valve 40 comprises a prosthetic heart valve, and may be configured to be deployed to a native valve of a heart. The prosthetic valve 40 may include distal anchors 42 and a plurality of prosthetic valve leaflets 44 (more clearly shown in the bottom view of FIG. 10B). The prosthetic valve 40 may include a valve body 41 that may support the plurality of prosthetic valve leaflets 44. The valve body 41, in examples, may include a skirt 46 and may include one or more frames.

The skirt 46, in examples, may extend around the prosthetic valve leaflets 44. The skirt 46 may comprise a sealing skirt for sealing with a portion of a heart. The skirt 46, for example, may comprise an outer surface of the valve body 41 and may contact a portion of a native heart valve, such as native heart valve leaflets, to seal with such portions. In examples, the skirt 46 may comprise another portion of the prosthetic valve 40 and may be positioned in other locations (e.g., interior of a frame or in another location as desired).

A frame 49 (marked in FIG. 10B) of the valve body 41 may support the plurality of prosthetic valve leaflets 44. The frame 49 may comprise an inner frame in examples that may be positioned radially inward of an outer frame 47 (marked in FIG. 10A). The outer frame 47 may surround the inner frame 49.

The outer frame 47 may comprise a portion of a sealing body that may include the skirt 46 for sealing with a portion of the native heart valve. The skirt 46, for example, may be positioned radially outward of the outer frame 47 (as shown in FIG. 10A) and the outer frame 47 may support the skirt 46 against the portion of the heart to be sealed. The skirt 46 may reduce the possibility of leakage outside of the flow channel of the prosthetic valve (e.g., paravalvular leakage). Other configurations of frames or valve bodies may be utilized in examples.

The implant may include struts 48 that form the frame 49 of the prosthetic valve 40 and the outer frame 47 may include struts as well. Certain of the struts 48 may end in end tab portions 50 that are configured to couple to a portion of a delivery apparatus. For example, the end tab portions 50 may be configured to engage a coupler 52 (as marked in FIGS. 14A and 14B) of a delivery apparatus to couple the prosthetic valve 40 to the delivery apparatus. The end tab portions 50 may include flared half-dome shapes, or another shape as desired to couple to the coupler 52. FIG. 10B illustrates a bottom view of the prosthetic valve 40.

The valve body 41 may surround a flow channel 45 (marked in FIG. 10A) that a central axis of the prosthetic valve 40 may extend along. The prosthetic valve leaflets 44 may extend radially inward from the valve body 41 towards the flow channel 45.

The plurality of prosthetic valve leaflets 44 may be configured to open and close to replicate the operation of a native valve. In the example shown in FIGS. 10A and 10B, the upper end 51 of the prosthetic valve 40 may comprise an inflow end of the prosthetic valve 40 and a lower end 53 of the prosthetic valve 40 may comprise an outflow end of the prosthetic valve 40. The prosthetic valve leaflets 44 may open and close to allow flow from the inflow end to the outflow end, and impede flow from the outflow end to the inflow end.

The prosthetic valve 40 shown in FIGS. 10A and 10B is configured as a prosthetic mitral valve, however, other forms of implants may be utilized as desired. For example, prosthetic aortic, tricuspid, or pulmonary valves may be utilized with the systems, apparatuses, and methods disclosed herein. Further, other forms of implants such as stents or other implants may be utilized with the systems, apparatuses, and methods disclosed herein as well.

The prosthetic valve 40 shown in FIGS. 10A and 10B may utilize the distal anchors 42 to engage a ventricular side of a valve, such as a mitral or tricuspid valve. The distal anchors 42 may comprise ventricular anchors that are positioned at the outflow end of the prosthetic valve 40. The distal anchors 42 may have a hook shape that allows each distal anchor 42 to hook around a native valve leaflet to secure the prosthetic valve 40 to the native valve. Each anchor 42 may comprise an elongate arm having a length. In examples, the prosthetic valve 40 may include proximal anchors 55 that may engage an atrial side of a mitral valve, as marked in FIGS. 16C and 17, although such proximal anchors 55 may be excluded in examples. One or more anchors may be coupled to the plurality of prosthetic valve leaflets 44 and each configured to anchor to a portion of the heart. Other forms of anchors may be utilized, as well as other forms of implants may be utilized in other examples.

Features of an implant that may be utilized are disclosed in U.S. patent application Ser. No. 16/028,172, filed on Jul. 5, 2018, and published as U.S. Patent Publication No. 2019/0008640, the entire contents of which are incorporated by reference herein. Additional details and example designs for an implant and prosthesis that may be utilized in examples herein are described in U.S. Pat. Nos. 8,403,983, 8,414,644, 8,652,203 and U.S. Patent Publication Nos. 2011/0313515, 2012/0215303, 2014/0277390, 2014/0277422, 2014/0277427, 2018/0021129, and 2018/0055629, the entirety of these patents and publications are hereby incorporated by reference and made a part of this specification. Further details and examples of a replacement heart valve or prosthesis and its method of implantation are described in U.S. Publication Nos. 2015/0328000 and 2016/0317301 the entirety of each of which is hereby incorporated by reference and made a part of this specification.

Figure 14A:
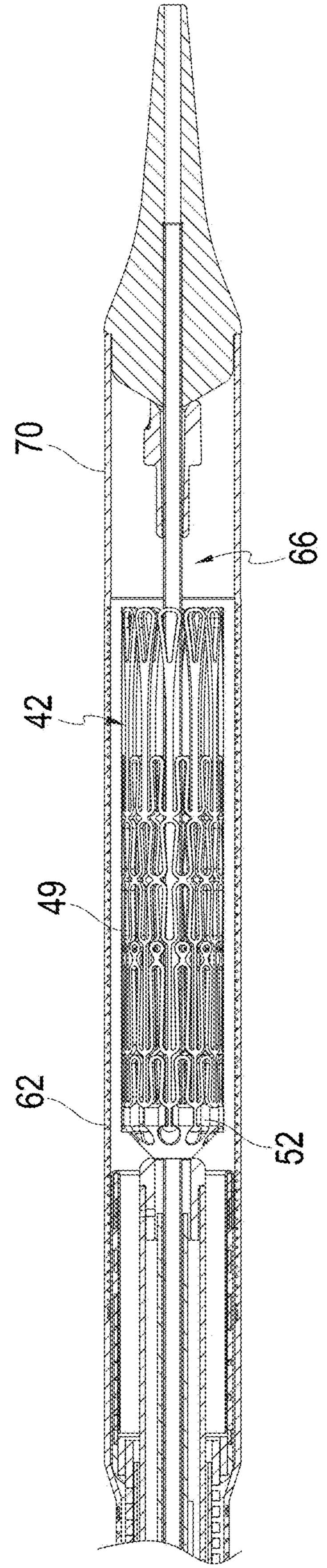
FIG. 14A illustrates a cross sectional view of an implant retention area of a delivery apparatus according to an example of the present disclosure.

The prosthetic valve 40 is compressible, such that the prosthetic valve 40 may be compressed in a direction radially towards a longitudinal axis or central axis that the prosthetic valve 40 surrounds. For example, the frame of the prosthetic valve 40 may be flexible, to allow for compression of the prosthetic valve 40. Upon compression in the direction radially towards the longitudinal axis, the prosthetic valve 40 may increase in length longitudinally along the longitudinal axis (with the end tab portions 50 and the distal anchors 42 extending in opposite directions along the longitudinal axis, for example as shown in FIG. 14A). In certain examples, the prosthetic valve 40 may be configured to compress in the direction radially towards the longitudinal axis without the prosthetic valve 40 increasing in length.

The anchors 42 as shown in FIGS. 10A and 10B may be covered with material that may cushion the anchors 42 against the native structure of the patient's heart. The anchors 42, for example, may comprise a rigid structure. The anchors 42 may be coupled to the frame 49 and integral with the struts 48 of the frame 49 in examples. The anchors 42 may include arms in the form of hooks that are rigid and may damage native structure of the patient's heart if they directly contact the native structure. The material may cover the arms of the anchors 42 to protect the native structure from such contact. The pad 25 shown in FIG. 8 for example, may be coupled to a respective anchor 42 to cover the arm.

Figure 11:
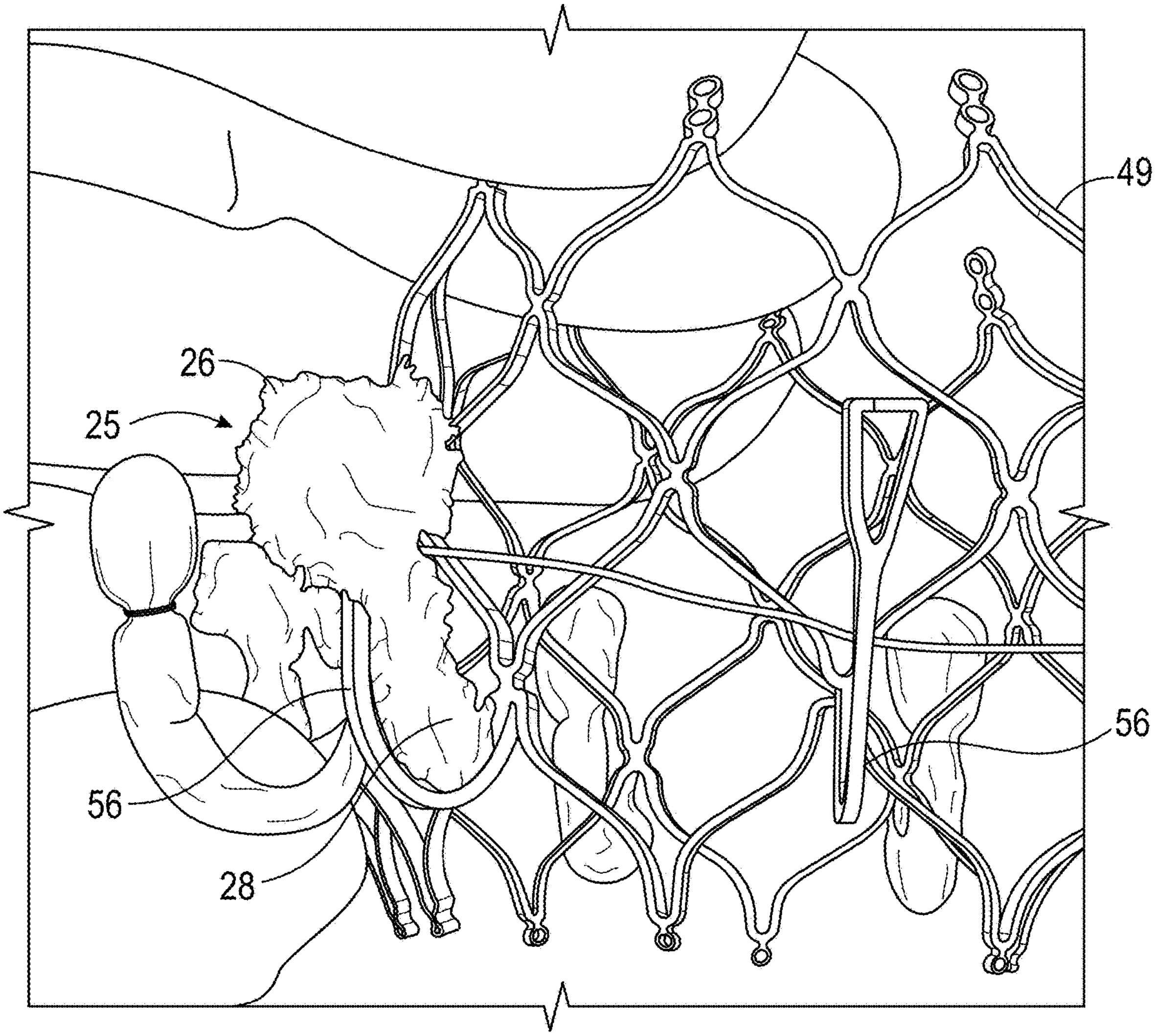
FIG. 11 illustrates a pad being coupled to an anchor of a prosthetic valve according to an example of the present disclosure.

FIG. 11 illustrates a step in a process of coupling the pad 25 to an arm 56 of an anchor 42. The outer frame 47 is excluded from view in FIG. 11. The pad 25 may be coupled to a tip of the anchor arm 56 via sutures or another form of coupling. The pad 25 may be applied with the head portion 26 of the pad 25 at the tip of the anchor arm 56. The anchor arm 56 may comprise an elongate arm and may include a surface 59 facing radially inward and a surface 61 facing radially outward as marked in FIG. 9. The pad 25 may cover the surface 59 facing radially inward so that when the anchor 42 hooks around a native structure such as a native leaflet, the pad 25 cushions the anchor 42 from contact with the native structure. The surface 59 facing radially inward may face towards the native valve leaflet upon deployment. The neck portion 28 of the pad 25 may extend along a length of the anchor arm 56, and may cover the surface 59 of the anchor arm 56 facing radially inward as shown in FIG. 11.

Figure 12:
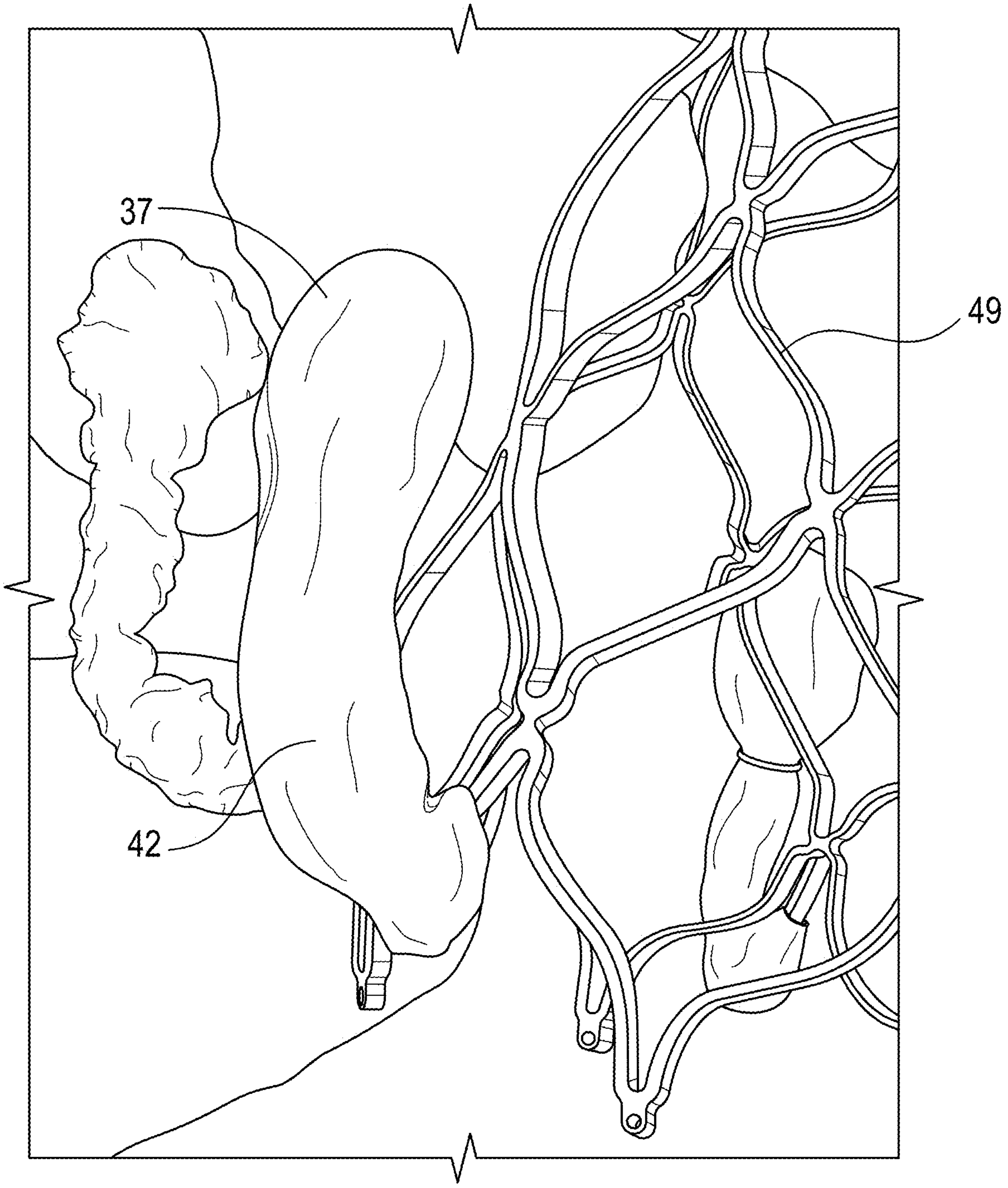
FIG. 12 illustrates a sleeve extending over a pad according to an example of the present disclosure.

With the pad 25 coupled to the anchor arm 56, a sleeve 37 as shown in FIG. 12 may extend over the anchor arm 56, and the pad 25 to cover the anchor arm 56 and pad 25. The sleeve 37 may cover the anchor arm 56 and pad 25 to provide a smooth outer surface for the anchor 42. The assembly upon the anchor arm 56 may have a configuration as shown in FIG. 9 for example. In examples, the pad 25 may extend over the tip of the anchor arm 56 and in examples may cover the opposite surface 61 of the anchor arm 56. The pad 25 for example, may suture to itself with the anchor arm 56 sandwiched between the pad 25 on the surface 59 facing radially inward and on the surface 61 facing radially outward. Other configurations of the pad 25 may be utilized in examples as desired.

The remaining portions of the prosthetic valve 40 may be assembled to produce a valve having an appearance as shown in FIGS. 10A and 10B.

The pad 25 cushions the anchor 42 during implantation to a native heart valve. The pad 25 may provide improved compressibility to cushion the anchor 42. Such improved compressibility may be desired over prior forms of cushions that may include foam or another closed cell material. The improved compressibility may further provide benefits during deployment of the prosthetic valve 40.

Figure 13:
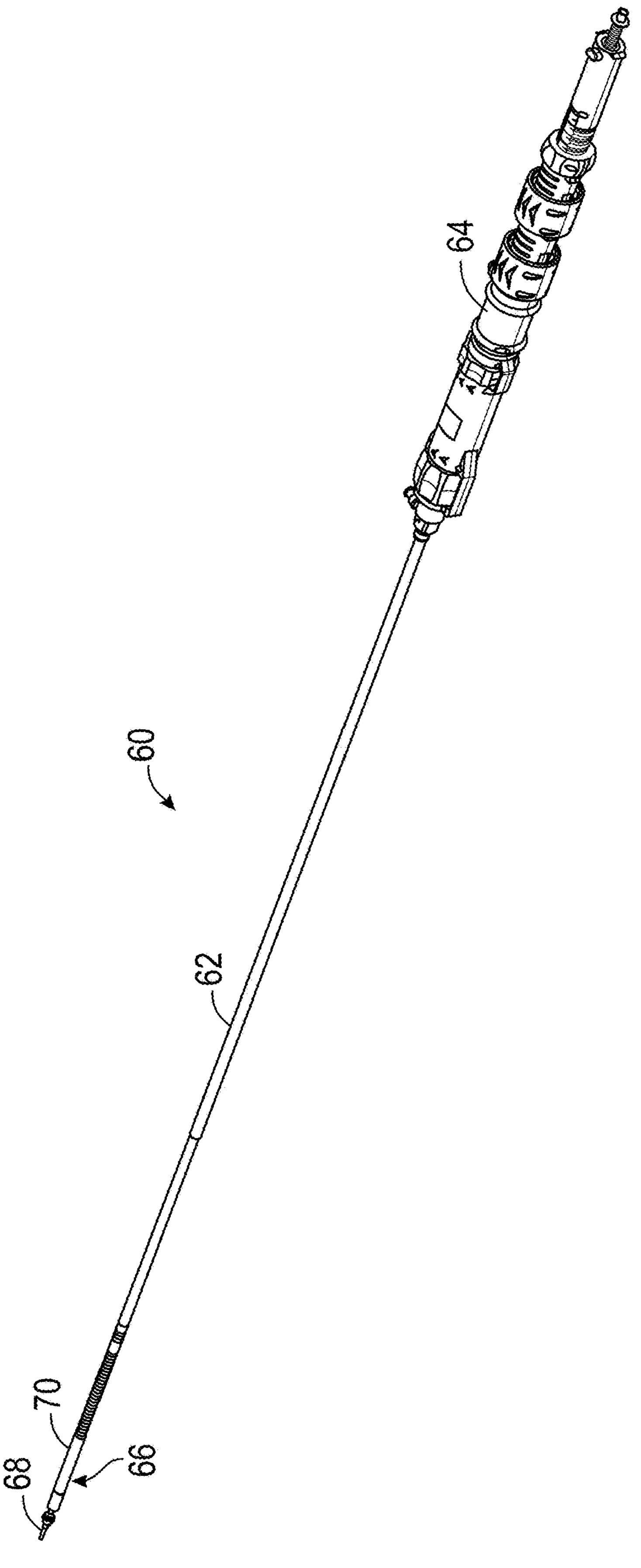
FIG. 13 illustrates a perspective view of a delivery apparatus according to an example of the present disclosure.

FIG. 13, for example, illustrates an example of a delivery apparatus 60 that may be utilized according to examples herein and may be utilized to deploy an implant such as the prosthetic valve 40. The delivery apparatus 60 may include an elongate shaft 62 having a proximal end coupled to a handle 64 and a distal end including an implant retention area 66 for the prosthetic valve 40, a nose cone 68, and a capsule 70 extending over the implant retention area 66. The elongate shaft 62 may be deflectable to position the prosthetic valve 40 in a desired position relative to an implantation site. Features of a delivery apparatus that may be utilized, as well as methods of deployment using a delivery apparatus are disclosed in U.S. patent application Ser. No. 16/028,172, filed on Jul. 5, 2018, and published as U.S. Patent Publication No. 2019/0008640, the entire contents of which are incorporated by reference herein.

The prosthetic valve 40 may be crimped in an elongated configuration within the capsule 70 prior to deployment, as shown in FIG. 14A for example. Only the frame 49 of the prosthetic valve 40 is shown in FIG. 14A for clarity. The distal anchors 42 are compressed and extend longitudinally along the longitudinal axis or central axis of the elongate shaft 62. The force of compression of the capsule 70 upon the distal anchors 42 is preferably low, to reduce the deployment force needed to deploy the prosthetic valve 40 from the capsule 70. With compressible pads 25 upon the distal anchors 42 the deployment force may be reduced in comparison with other pad materials such as foam or another closed cell material. As such, improved deployment of the prosthetic valve 40 may result from use of the pads 25.

Figure 14B:
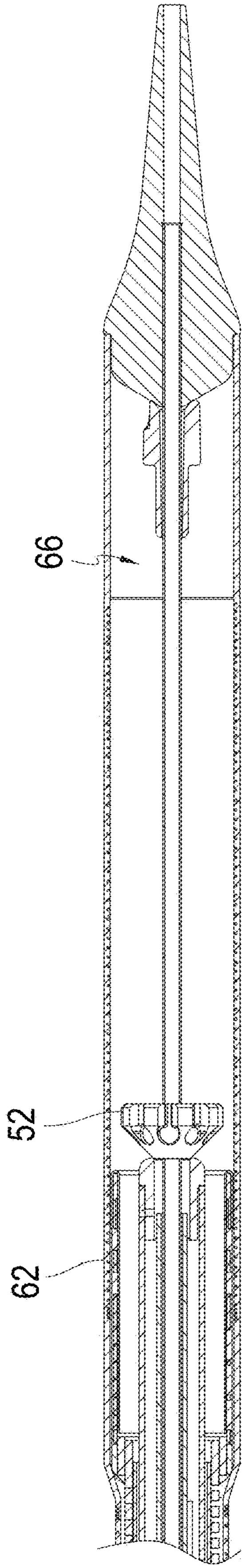
FIG. 14B illustrates a cross sectional view of the implant retention area shown in FIG. 14A according to an example of the present disclosure.

FIG. 14B illustrates the prosthetic valve 40 absent from the elongate shaft 62.

Figure 15:
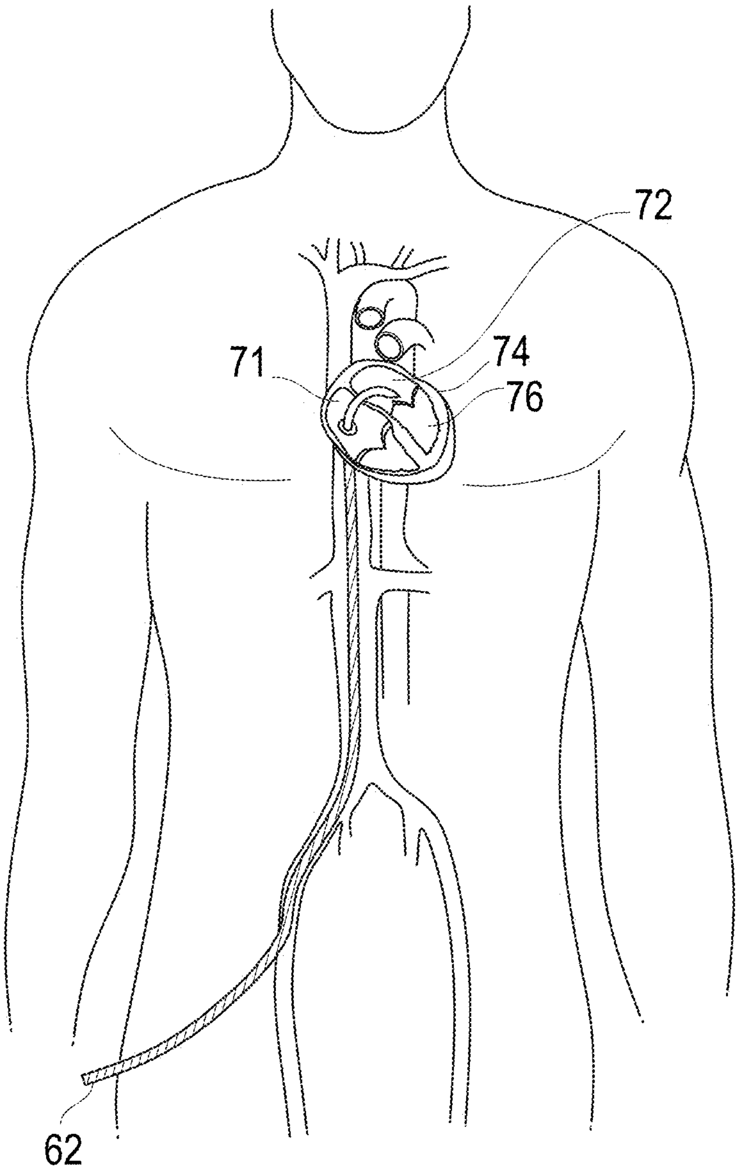
FIG. 15 illustrates a delivery apparatus approaching a mitral valve according to an example of the present disclosure.

Deployment of the prosthetic valve 40 may occur according in a variety of forms, including transfemoral entry, or surgical methods of entry into the patient's heart. FIG. 15 illustrates an exemplary procedure in which femoral entry is utilized. The elongate shaft 62 of the delivery apparatus 60 may pass through the femoral vein, among other entry points. FIG. 15 illustrates the elongate shaft 62 of the delivery apparatus 60 passing transfemoral to a right atrium 71 and then transseptal to the left atrium 72 of the patient's heart 74. The elongate shaft 62 may deflect to position the prosthetic valve 40 for deployment to the mitral valve. The elongate shaft 62 may deflect towards the left ventricle 76.

Figure 16A:
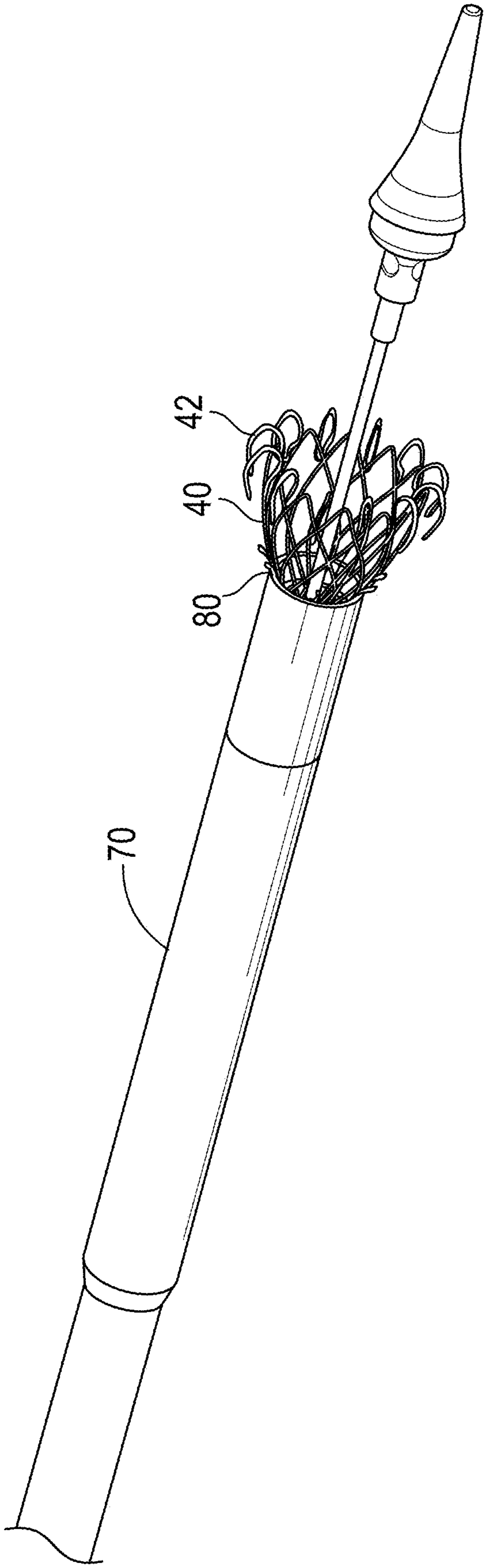
FIG. 16A illustrates a side perspective view of a valve being deployed from a delivery apparatus according to an example of the present disclosure.
Figure 16B:
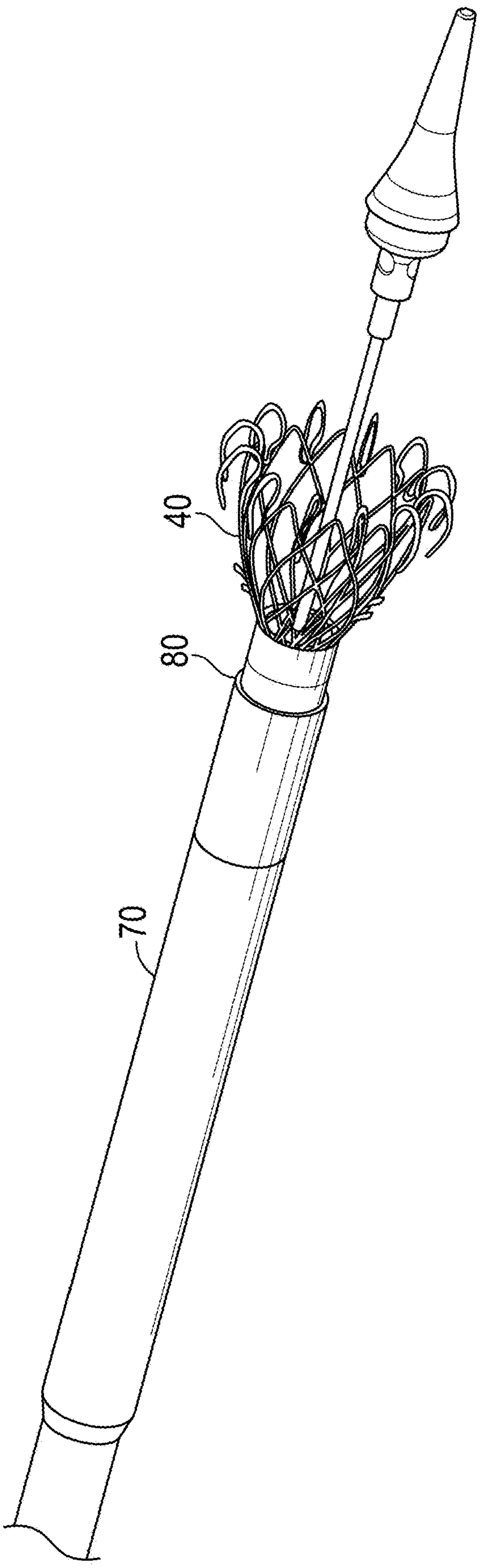
FIG. 16B illustrates a side perspective view of a valve being deployed from a delivery apparatus according to an example of the present disclosure.
Figure 16C:
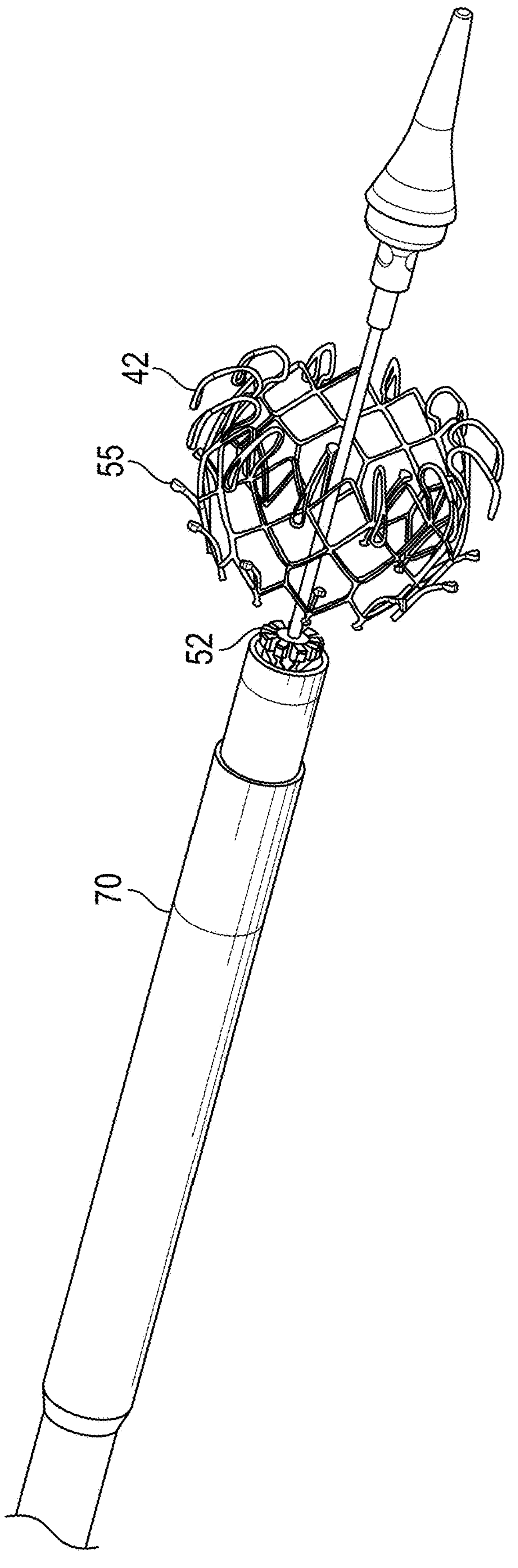
FIG. 16C illustrates a side perspective view of a valve being deployed from a delivery apparatus according to an example of the present disclosure.

FIGS. 16A-16C illustrate steps in the deployment of the prosthetic valve 40, in which the capsule 70 retracts relative to the prosthetic valve 40. The prosthetic valve 40 is deployed to a native valve of a patient's heart. The prosthetic valve 40 extends out of an opening 80 in the capsule 70. The distal anchors 42 may extend distally and may then deflect proximally to hook around native valve leaflets upon deployment. Each of the distal anchors 42 may be hooked around a native valve leaflet. The pads 25 (not shown in FIGS. 16A-16C) may cushion the anchors 42 upon deployment and the compressibility of the pads may reduce the deployment force of the prosthetic valve 40. The pads 25, for example, may be positioned on the surface 59 facing radially inward, to cushion the anchor 42 against a native valve leaflet upon deployment.

FIGS. 16B and 16C illustrate the capsule 70 further retracting to deploy the prosthetic valve 40.

Figure 17:
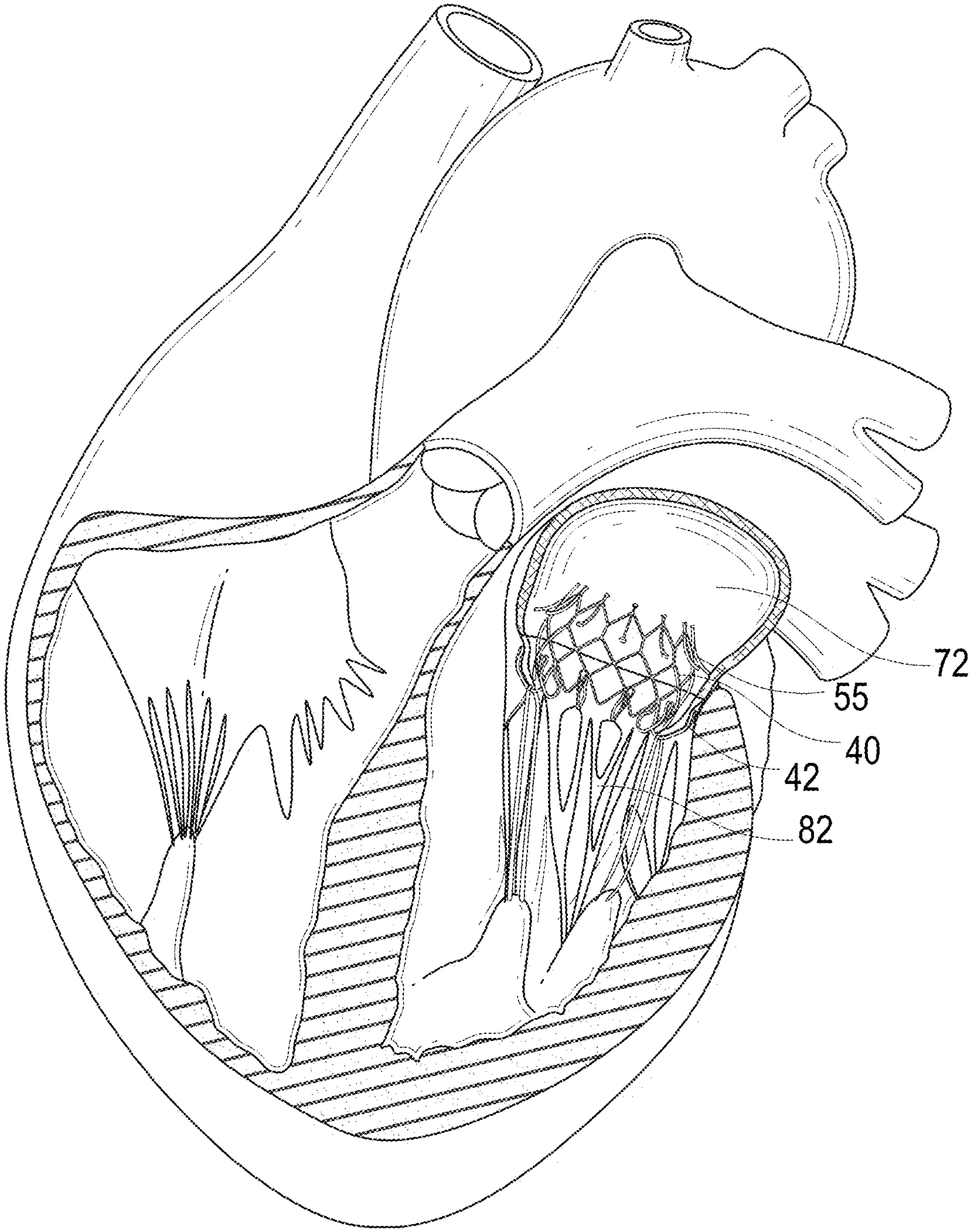
FIG. 17 illustrates a schematic view of a valve deployed to a mitral valve according to an example of the present disclosure.

FIG. 17 illustrates the prosthetic valve 40 deployed to a native mitral valve, with the distal anchors 42 hooked around the native valve leaflets. The pads 25 (not shown in FIG. 17) may cushion the distal anchors 42 upon deployment. The distal anchors 42 may hook around the native valve leaflets and may hook around chordae 82 in examples if desired.

Other deployment methods may be utilized in examples. For example, balloon expandable prosthetic valves may be utilized. Such valves may be positioned upon an inflatable balloon upon entry into a patient's body or may be slid onto an inflatable balloon following entry into the patient's body. The inflatable balloon may be inflated with fluid to expand and deploy the prosthetic valve. Mechanically expandable prosthetic valves may further be utilized, along with self-expanding valves, and other forms of deployment.

In examples, the prosthetic valve 40 may be deployed to other valves, such as the tricuspid valve in examples. Other forms of prosthetic valves may be utilized in examples herein to deploy to other valves such as the aortic or pulmonary valves, or to other portions of the patient's body.

The use of the fabric 10 is not limited to use in pads for anchors, and may be utilized in other positions upon a prosthetic valve as desired. For example, the fabric 10 may comprise at least a portion of the skirt of the prosthetic valve, or another portion as desired. Further, the fabric 10 may be utilized on other implants, such as stents, or other anchoring devices within the patient's body, among other structures.

Figure 18:
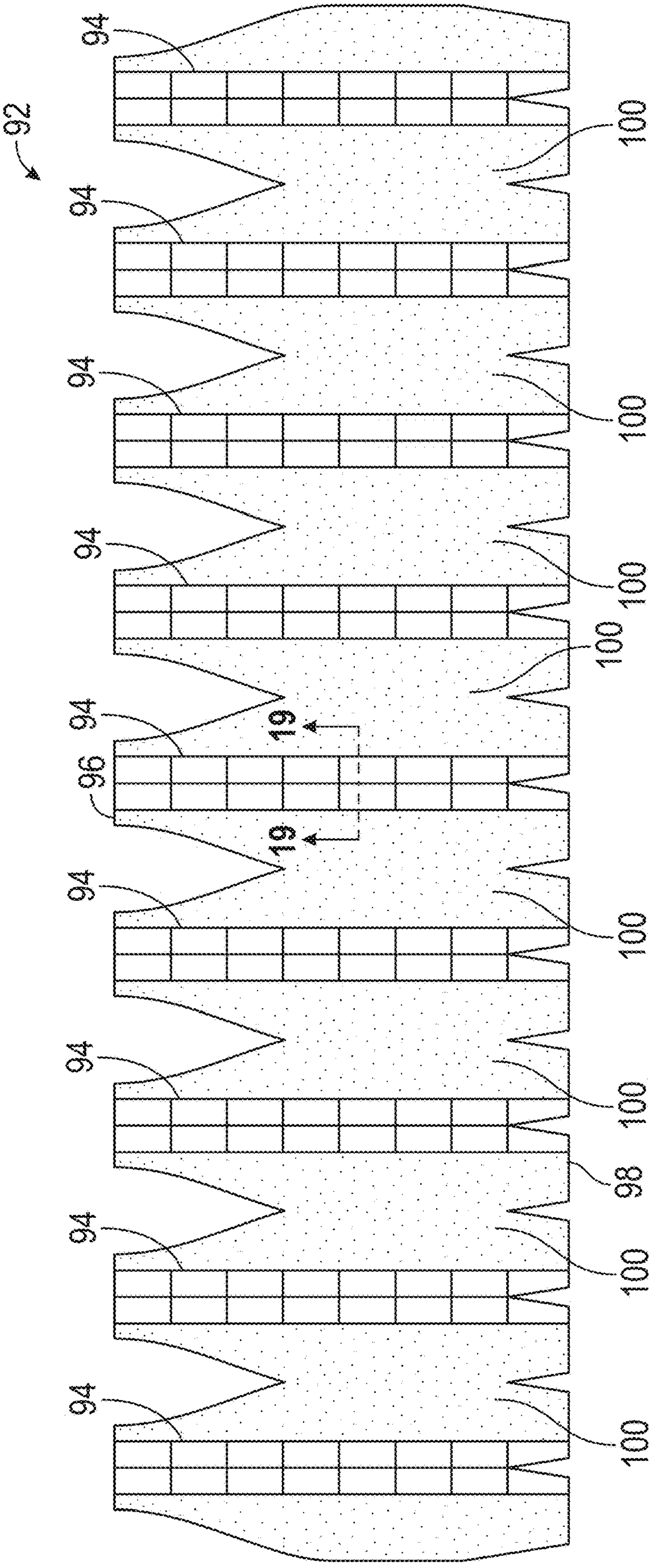
FIG. 18 illustrates a plan view of a skirt according to an example of the present disclosure.

FIG. 18 illustrates a plan view of an example of a skirt 92 that may be utilized in examples herein. At least a portion of the skirt 92 may include one or more friction bodies 94 for providing friction with a portion of the heart. In FIG. 18, the friction bodies 94 may comprise a fabric having a honeycomb weave pattern as disclosed herein (e.g., the fabric 10 discussed in regard to FIG. 1).

Each of the friction bodies 94 may comprise a strip in examples. The friction bodies 94 may comprise strips of material that may extend axially with respect to the central axis of a prosthetic valve. The central axis may comprise an axis that the flow channel 45 (marked in FIG. 20) extends along. The strips of material may extend axially from a proximal portion 96 of the skirt 92 to a distal portion 98 of the skirt 92, or may extend only partially along an axial length of the skirt 92.

In examples, the friction bodies 94 may be circumferentially spaced from each other. The circumferential spacing may be equal or may be varied in examples. The friction bodies 94 may be spaced from each other with segments 100 of the skirt positioned between the friction bodies 94. The segments 100 may be interleaved between segments of the friction bodies 94 and may be circumferentially adjacent to each of the segments of the friction bodies 94.

The segments 100 may comprise relatively smooth portions of the skirt 92, which may be smoother than the friction bodies 94. The segments 100, for example, may comprise a plain weave or other form of fabric producing a lesser surface friction than the friction bodies 94.

Figure 20:
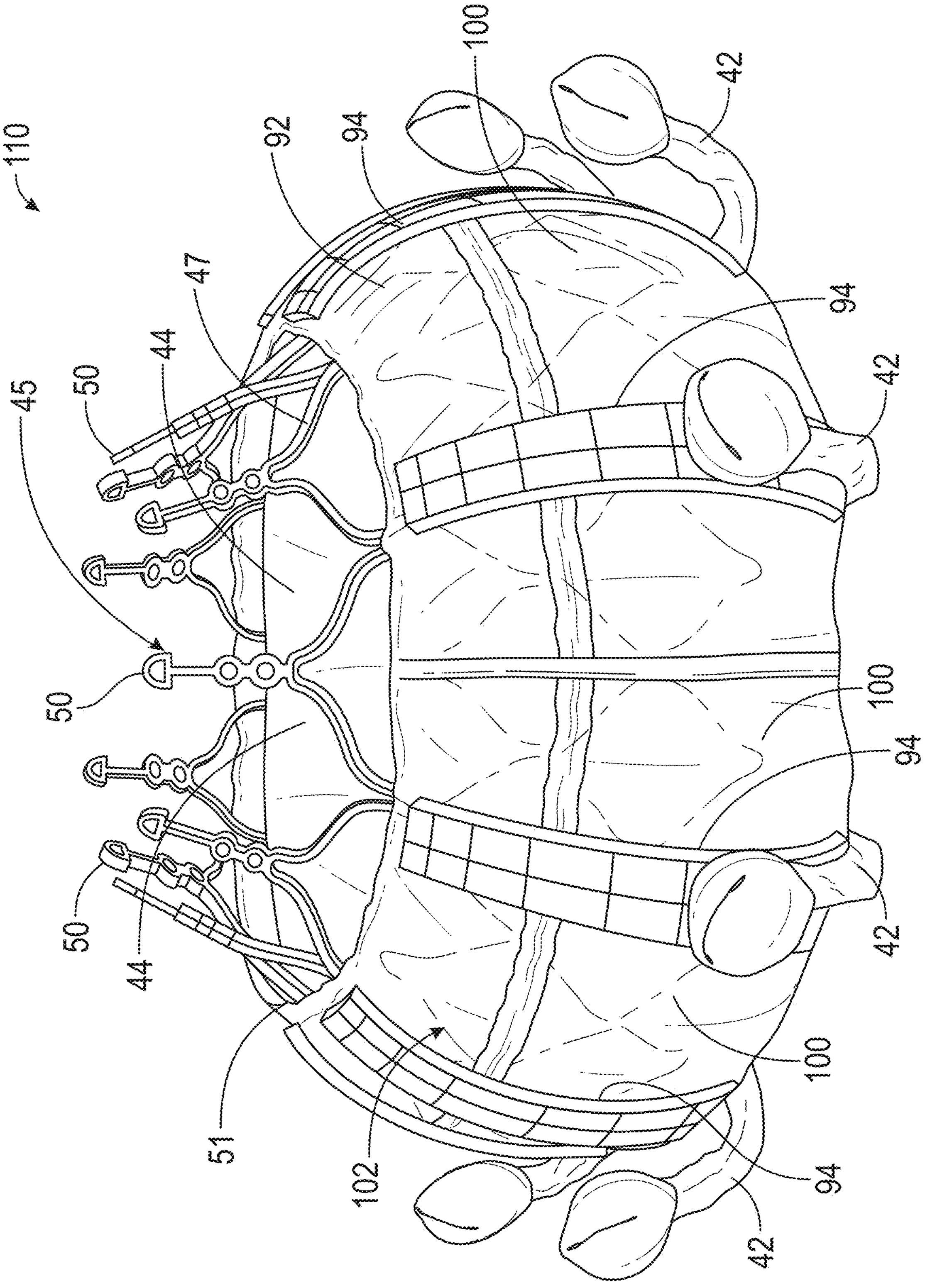
FIG. 20 illustrates a perspective view of a prosthetic valve utilizing a skirt as shown in FIG. 18.

The friction bodies 94 may be positioned at locations of anchors 42 (as marked in FIG. 20). The friction bodies 94 may be circumferentially aligned with the positions of the anchors 42 such that each friction body 94 is positioned interior or radially inward of a native valve leaflet and an anchor 42 is positioned exterior or radially outward of a native valve leaflet. The friction bodies 94 may be positioned on an opposite side of a leaflet of a native valve than a respective one of the plurality of anchors 42. The friction bodies 94 may be positioned opposed to the anchors 42. Enhanced friction may result at the anchoring points provided by the anchors 42.

Each friction body 94 may extend along a length of each anchor 42, yet positioned on the skirt 92 radially inward of the anchor 42. The friction bodies 94 in the form of strips may be aligned with the length of a respective one of the elongate arms of the anchors 42 (as shown in FIG. 20 for example). Various other positions of friction bodies 94 may be provided. For example, each friction body 94 may be positioned circumferentially offset from a position of an anchor 42 or may be positioned to extend horizontally or in a circumferential direction in examples as desired. Various combinations of orientations of friction bodies 94 may be provided as desired.

The friction bodies 94 may increase friction with the portion of the heart due to the surface roughness provided by the honeycomb weave pattern as shown in FIGS. 1 and 3. The configuration of the pit surrounded by walls shown in FIG. 3 may increase a friction force provided by the friction bodies 94, as compared to a relatively smoother segment 100 positioned adjacent to the friction bodies 94.

Figure 19:
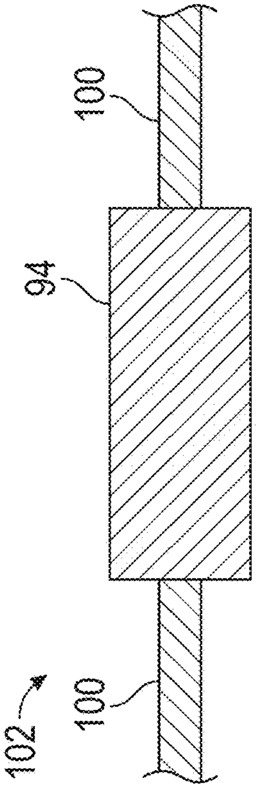
FIG. 19 illustrates a cross sectional view of the skirt along line 19-19 shown in FIG. 18.

In examples, the friction bodies 94 may be thicker than the segment 100. FIG. 19, for example, illustrates a cross sectional view along line 19-19 in FIG. 18 of a friction body 94 having a greater thickness than the adjacent segments 100. The increased thickness may allow the friction body 94 to protrude from the outer surface 102 of the skirt 92 to increase the contact and friction between the friction body 94 and the portion of the heart. In examples, the friction body 94 may be coplanar or flush with the segment 100 at the outer surface 102 to provide a uniform height of the outer surface 102. In such a configuration the pits and walls shown in FIG. 3 may provide a friction force against the portion of the heart. In examples, the friction body 94 may be heat set to be coplanar or flush with the segment 100 at the outer surface 102.

In examples, the honeycomb weave pattern may provide a cushion for the skirt 92. For example, the honeycomb weave pattern may be compressible, as disclosed herein, to provide a cushion. The cushion may reduce the possibility of damage to the native valve and may reduce the possibility of electrical conduction disturbance with the native valve.

FIG. 20 illustrates a perspective view of a prosthetic valve 110 including the skirt 92 shown in FIG. 18. The skirt 92 is shown flattened in FIG. 18 and may be wrapped around a frame of the prosthetic valve 110 as shown in FIG. 20. The skirt 92 may be wrapped around an outer frame 47 or another frame of the prosthetic valve as desired. The friction bodies 94 and accordingly the honeycomb weave pattern may be positioned on the outer surface 102 of the skirt 92.

The friction bodies 94 are positioned at the locations of the anchors 42. As such, during deployment, a portion of the native valve such as a native valve leaflet may be positioned between a respective pair of an anchor 42 and a friction body 94. The friction bodies 94 may be configured to provide friction with a leaflet of the native valve. The friction bodies 94 may enhance the friction provided to improve securement of the prosthetic valve 110 in position. The securement may be in a distal direction, which may reduce the possibility of ventricular movement of the prosthetic valve 110 in a mitral or tricuspid deployment, or the securement may be in a proximal direction, which may reduce the possibility of atrial movement of the prosthetic valve 110 in a mitral or tricuspid deployment. In examples, combinations of distal and proximal securement may be utilized.

Various modifications of the skirt 92 may be provided in examples.

Figure 21:
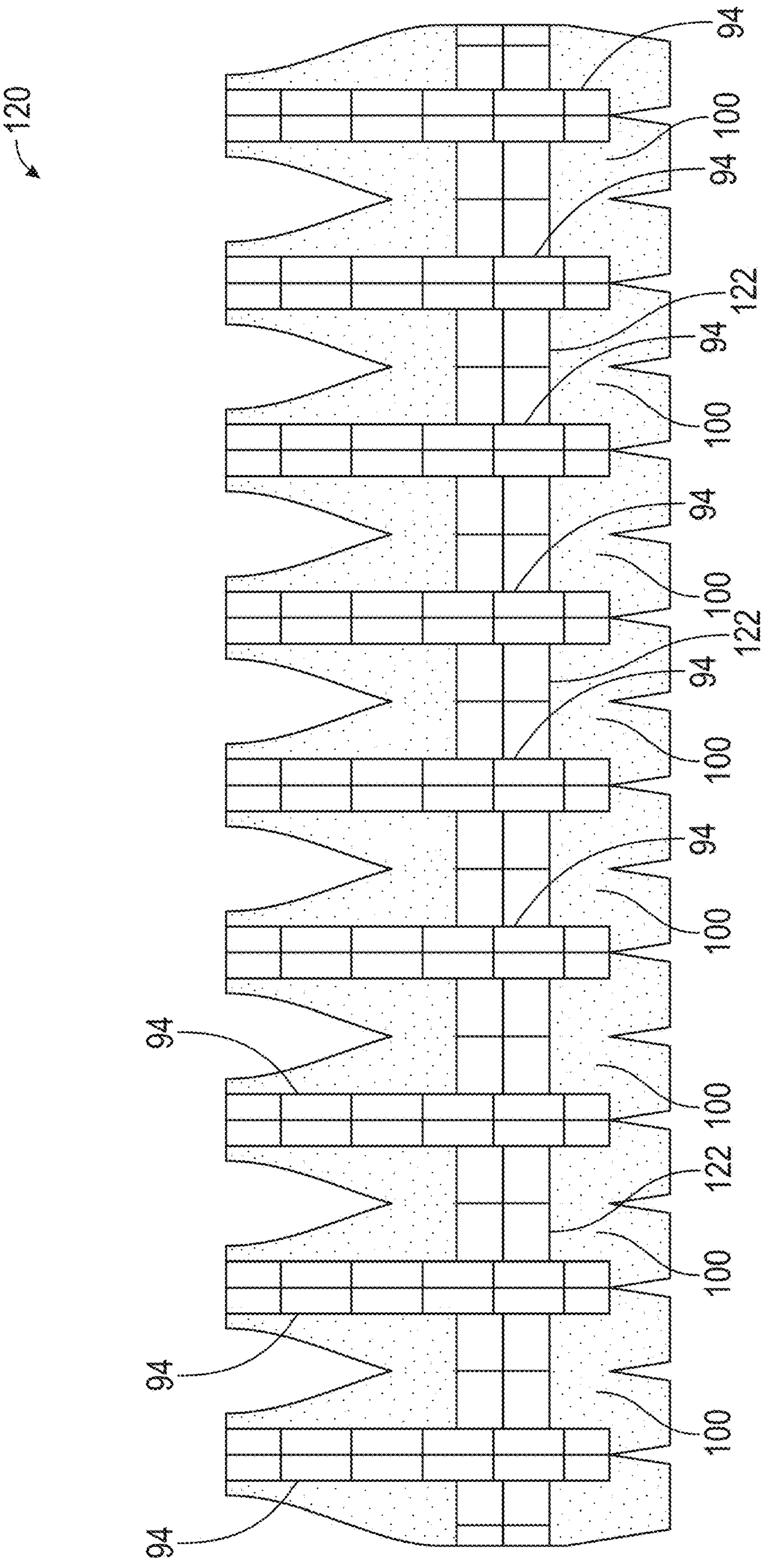
FIG. 21 illustrates a plan view of a skirt according to an example of the present disclosure.

FIG. 21, for example, illustrates an example of a skirt 120 including one or more friction bodies 122 extending circumferentially. The friction bodies 122 may comprise one or more strips extending circumferentially. The friction bodies 122 may extend circumferentially along the segments 100 and between the axially extending friction bodies 94.

Figure 22:
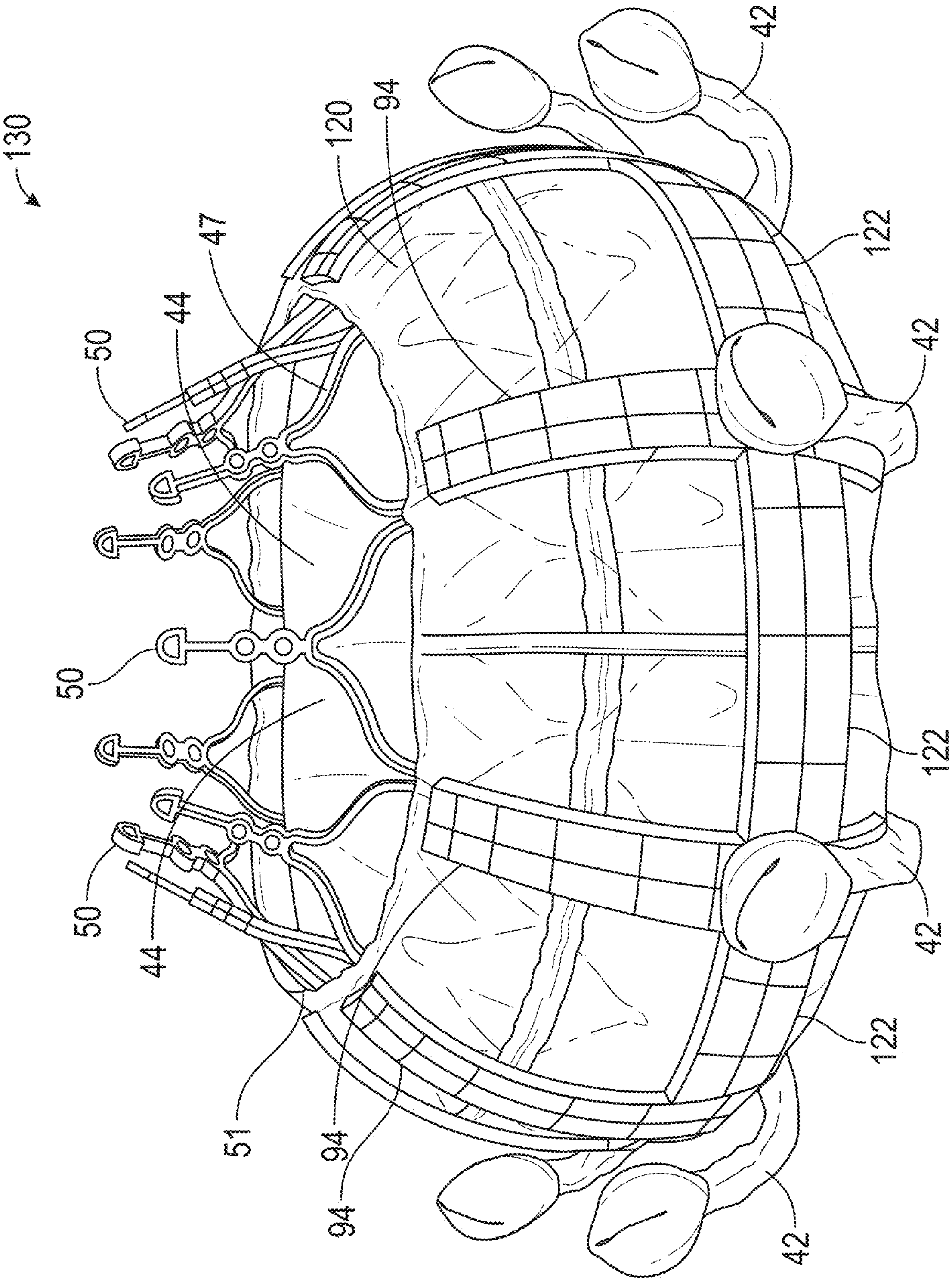
FIG. 22 illustrates a perspective view of a prosthetic valve utilizing a skirt as shown in FIG. 21.

The friction bodies 122 may be positioned to extend between the position of circumferentially adjacent anchors 42 (as shown in FIG. 22). The friction bodies 122 accordingly may form a circumferentially extending band about the prosthetic valve. The band may be a raised band or may be flush or coplanar with adjacent portions of the skirt 120 (e.g., the segments 100).

The friction bodies 122 may comprise the honeycomb weave pattern as disclosed herein. The friction bodies 122 may comprise a pad and may provide a cushion for the prosthetic valve with the native valve. The honeycomb weave pattern may be compressible to provide a cushion, as disclosed herein. The cushion may provide a variety of benefits. For example, the cushion may reduce the possibility of damage to the native valve and may reduce the possibility of electrical conduction disturbance with the native valve. In examples, reduced pressure against the AV node may be provided.

In examples, the circumferentially extending friction body 122 may provide an enhanced seal with a portion of a heart valve. For example, a reduced possibility of paravalvular leakage may result.

FIG. 22, for example, illustrates a prosthetic valve 130 utilizing the skirt 120. The portion of the skirt 120 having the friction bodies 122 and accordingly the honeycomb weave pattern may extend circumferentially between adjacent anchors of the plurality of anchors 42. The friction bodies 122 may be positioned in other locations, such as towards a proximal portion of the prosthetic valve or another portion as desired.

In examples, the entirety of the skirt or the entirety of the outer surface of the valve body may comprise a honeycomb weave pattern or another form of friction body.

In examples of a prosthetic valve, the axially extending friction bodies 94 may be excluded and only a circumferentially extending friction body 122 may be provided. In such an example, the circumferentially extending friction body 122 may extend around the entirety of the prosthetic valve or around only a portion of the prosthetic valve. For example, segments of the circumferentially extending friction body 122 may be provided as desired, or a continuous circumferentially extending friction body 122 may be provided as a band around the prosthetic valve.

Figure 23:
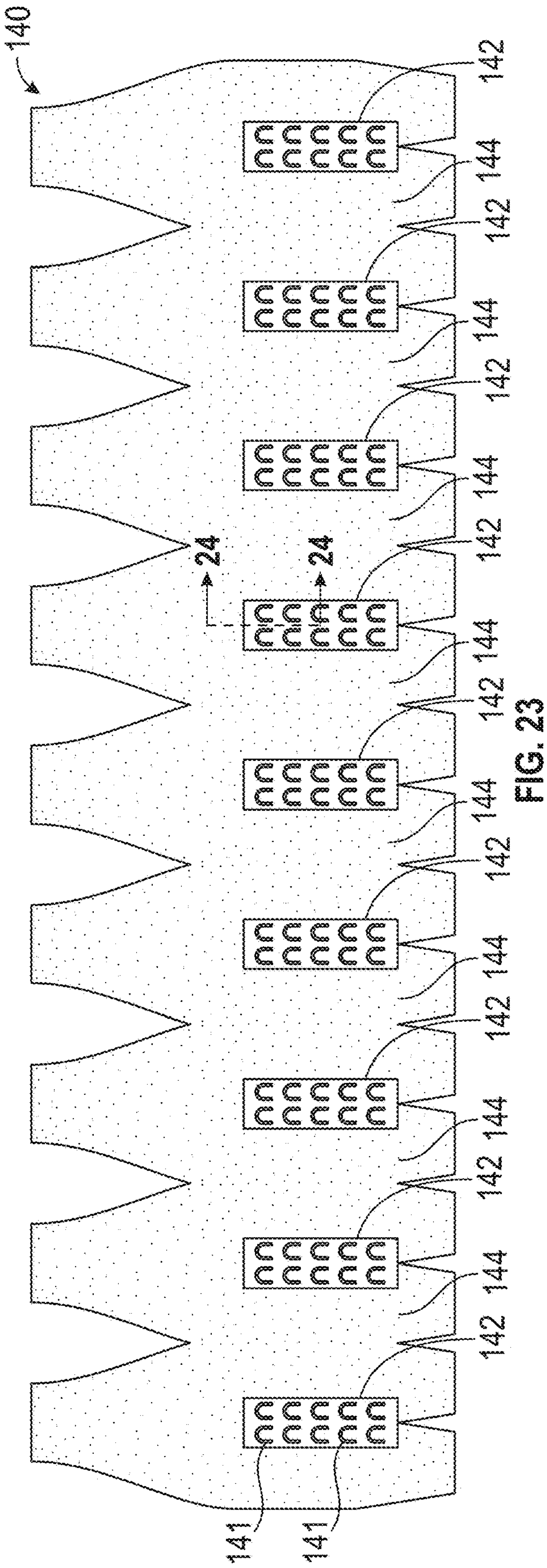
FIG. 23 illustrates a plan view of a skirt according to an example of the present disclosure.

FIG. 23 illustrates an example of a skirt 140 in which the friction bodies 142 comprise strips of protrusions in the form of loops 141. At least a portion of the skirt 140 may include the friction bodies 142 for providing friction with a portion of the heart. The friction bodies 142 may each comprise a patch having the loops 141.

In examples, the loops 141 may comprise a material that may be used in a hook and loop fastener arrangement. The loops 141, however, may be utilized solely without the corresponding mating hooks. In examples, a combination of loops 141 and hooks may be utilized with the friction body 142.

The friction bodies 142 may be positioned in a similar manner as discussed regarding the friction bodies 94 shown in FIG. 18. For example, the friction bodies 142 may comprise strips. The strips may be positioned at the positions of the anchors, with segments 144 positioned between the friction bodies 142. The strips may extend axially with respect to a central axis of a prosthetic valve. The central axis may comprise an axis that the flow channel 45 (marked in FIG. 25) extends along. The friction bodies 142 may extend for the entirety of the axial length of the skirt 140, or for only a portion of the axial length as shown in FIG. 23. For example, the friction bodies 142 may be positioned at a distal portion of the skirt 140 at a position opposed to the anchors 42.

Figure 24:
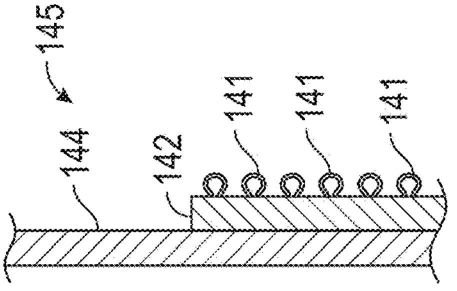
FIG. 24 illustrates a cross sectional view of the skirt along line 24-24 shown in FIG. 23.

FIG. 24 illustrates a cross sectional view of the friction bodies 142 upon the skirt 140. The loops 141 are shown to protrude from the outer surface 145 of the skirt 140.

Figure 25:
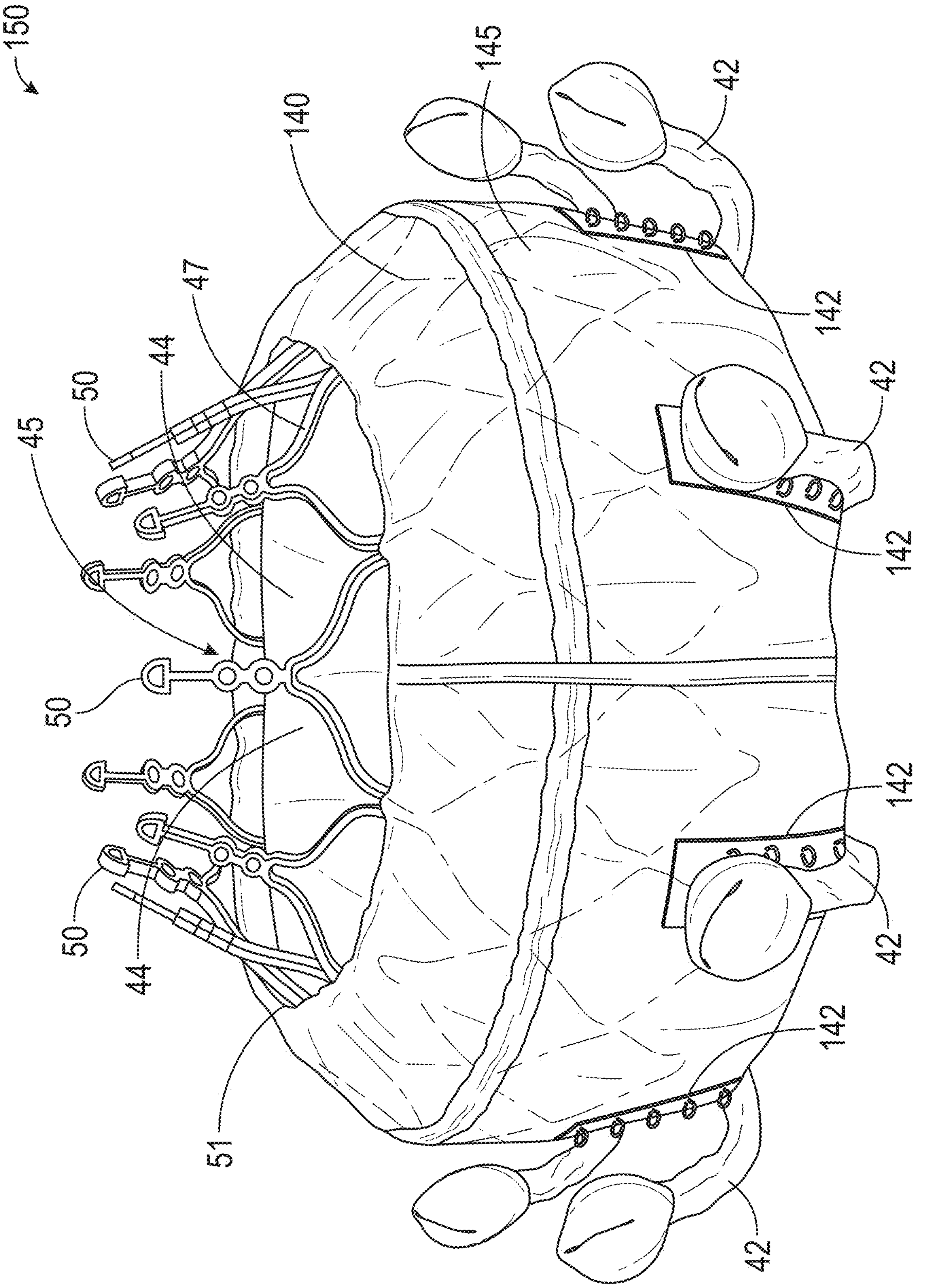
FIG. 25 illustrates a perspective view of a prosthetic valve utilizing a skirt as shown in FIG. 24.

FIG. 25 illustrates a prosthetic valve 150 including the friction bodies 142. The outer surface 145 of the skirt 140 may include the friction bodies 142. The friction bodies 142 may be aligned with a length of a respective one of the elongate arms of the anchors 42. The friction bodies 142 may be positioned opposed to each of the plurality of anchors 42.

The friction bodies 142 may enhance anchoring to the heart by providing friction. The friction bodies 142 may be configured to provide friction with a leaflet of a native valve. The friction bodies 142 may be positioned on an opposite side of a leaflet of a native valve than a respective one of the anchors 42. Various other locations of the friction bodies 142 may be provided in examples. Other forms of friction bodies may be utilized in examples.

Figure 26:
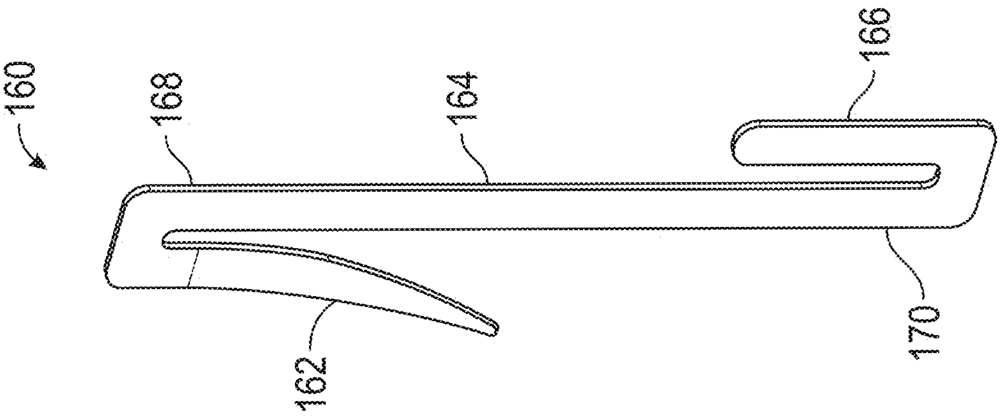
FIG. 26 illustrates a perspective view of a friction body according to an example of the present disclosure.

FIG. 26 illustrates an example of a friction body 160 that may be utilized in examples. The friction body 160 may provide friction with a portion of a heart. The friction body 160 may comprise a protrusion 162. The protrusion 162 may be coupled to a shaft 164. The friction body 160 may include a coupler 166 in examples.

The friction body 160 may comprise a wire that may be made out of a rigid material such as a metal, alloy, or polymer, among other forms of rigid materials. The material may comprise a biocompatible material such as Nitinol (NiTi), which may have a shape memory. Other forms of materials may be utilized as desired, including other forms of shape memory materials or other materials.

Figure 28:
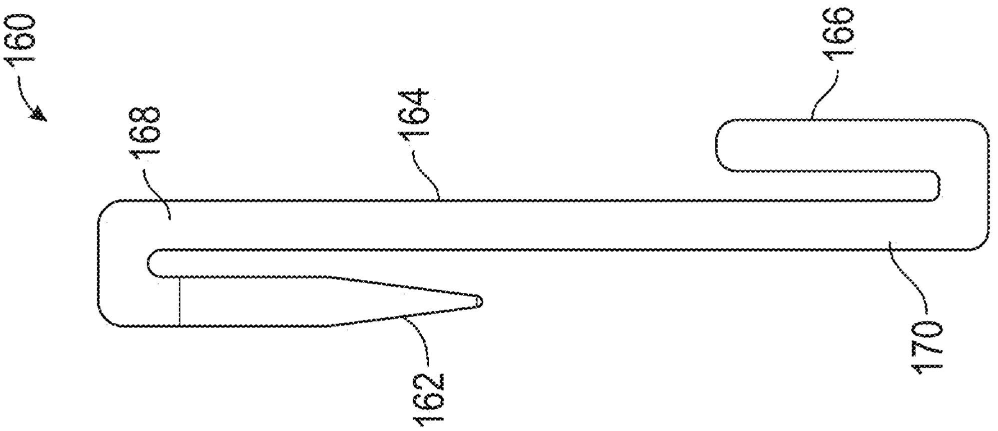
FIG. 28 illustrates a front view of the friction body shown in FIG. 26.
Figure 27:
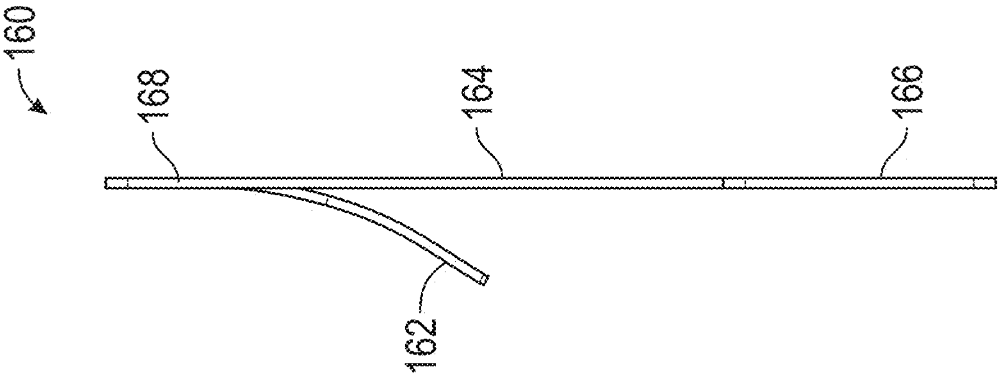
FIG. 27 illustrates a side view of the friction body shown in FIG. 26.

The friction body 160 may be stamped or otherwise cut (e.g., laser cut) out of a sheet of material and thus may have a flat shape. The protrusion 162 may be deflected outward from the sheet of material and may be shape set. As such, the protrusion 162 may be configured to be flattened when the prosthetic valve is in a compressed or undeployed configuration and may be deflected outward when the prosthetic valve is expanded or deployed. FIG. 27, for example, illustrates a side view of the friction body 160 showing the angle of the protrusion 162. FIG. 28 illustrates a front view of the friction body 160. The protrusion 162 may have a length between 2 to 3 millimeters in examples, although a greater or lesser length may be provided as desired.

The protrusion 162 may comprise a pointed tip that may be angled in a direction. The prosthetic valve, for example, may have a proximal portion that may comprise an inflow and a distal portion that may comprise an outflow. The pointed tip may be angled in a direction that may be a distal direction, or another direction may be provided in examples (e.g., a proximal direction). The pointed tip may be thus angled to resist movement in the distal direction, or in examples may resist movement in the proximal direction. In examples, the protrusion may be configured to extend perpendicular with respect to an outer surface of a skirt.

The protrusion 162 may be positioned at a proximal end portion 168 of the shaft 164. The shaft 164 may extend from the proximal end portion 168 to a distal end portion 170 of the shaft 164.

The friction body 160 may be configured to be embedded within a fabric of a skirt. For example, the shaft 164 may be woven into the skirt, with the shaft 164 held in position with the warp of the skirt. Such a configuration may secure a horizontal or circumferential position of the shaft 164. The coupler 166 may comprise a bend at the distal end portion 170 of the shaft 164. The coupler 166 may be woven into the skirt to secure a vertical or axial position of the friction body 160.

The friction body 160 may be positioned in a variety of locations on a skirt as desired. The friction body 160, in examples, may be positioned to align along the axial length of the prosthetic valve. The shaft 164 may extend along the axial length of the prosthetic valve. Each of the friction bodies 160 may comprise a strip that may extend axially with respect to the central axis of a prosthetic valve. The central axis may comprise an axis that the flow channel 45 (marked in FIG. 30) extends along. Other directions of orientation may be provided in examples.

In examples, the friction body 160 may be positioned to circumferentially align with the position of the anchors, similar to the positions of the friction bodies shown in FIGS. 20 and 25. The friction bodies 160 may be positioned opposed to the anchors 42. The friction bodies 160 may be aligned with a length of a respective one of the elongate arms of the anchors 42.

The friction bodies 160 may be configured to provide friction with a leaflet of a native valve. The friction bodies 160 may be positioned on an opposite side of a leaflet of a native valve than a respective one of the anchors 42. The friction bodies 160 accordingly may increase the friction provided at the position of the anchors. Other positions may be utilized in examples.

Figure 29:
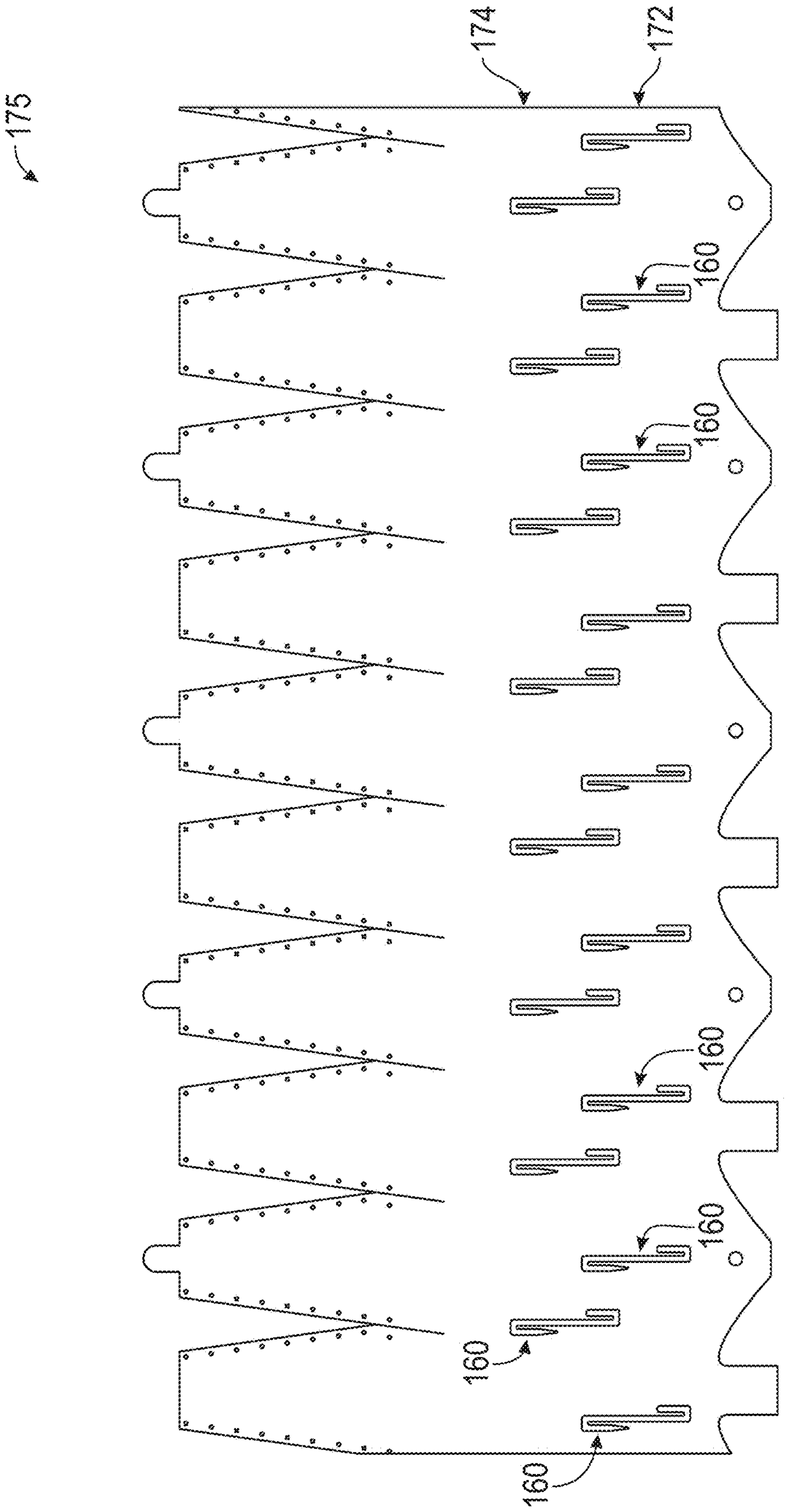
FIG. 29 illustrates a plan view of a skirt utilizing a friction body as shown in FIG. 26.

FIG. 29, for example, illustrates the friction bodies 160 coupled to a skirt 175 in a configuration in which multiple rows 172, 174 of the friction bodies 160 may be provided. A distal row 172 of circumferentially spaced friction bodies 160 may be provided and a proximal row 174 may be provided. The distal row 172 may be axially spaced from the proximal row 174. The friction bodies 160 of the distal row 172 may be circumferentially spaced from each other, which may include equal spacing or another form of spacing. The friction bodies 160 of the proximal row 174 may be circumferentially spaced from each other, which similarly may include equal spacing or another form of spacing. The friction bodies 160 of the proximal row 174 may be circumferentially offset from the friction bodies 160 of the distal row 172. As such, the distal row 172, for example, may be positioned opposed to the anchors 42 and the proximal row 174 may be positioned circumferentially between adjacent anchors 42. In examples, a greater or lesser number of rows may be utilized. The orientation of the friction bodies 160 within the rows may be varied as desired. Various other configurations may be utilized in examples.

A greater or lesser number of friction bodies 160 within the rows may be provided in examples. For example, a number of friction bodies 160 corresponding to the number of anchors may be provided. A greater number (e.g., 10-15 friction bodies per row) may be provided if nine anchors were utilized for example. Other configurations may be utilized.

Combinations of protrusions that are oriented in the distal direction and protrusions that are oriented in the proximal direction may be provided, along with solely protrusions oriented in a distal direction or in a proximal direction.

Figure 30:
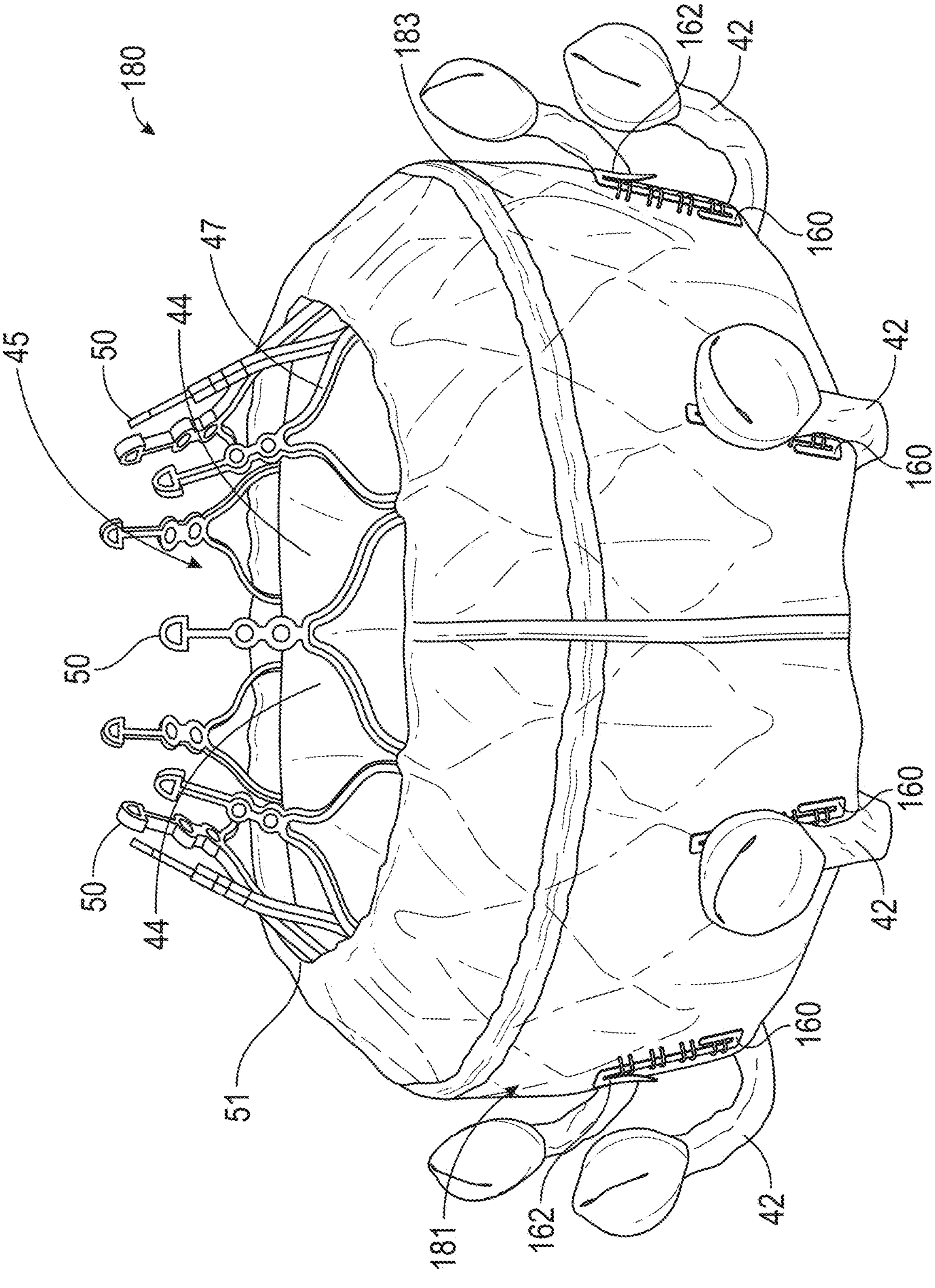
FIG. 30 illustrates a perspective view of a prosthetic valve utilizing a skirt as shown in FIG. 29.

FIG. 30 illustrates an example of a prosthetic valve 180 that may utilize the friction bodies 160. The outer surface 181 of the skirt 183 may include the friction bodies 160. The friction bodies 160 are shown at the positions of the anchors 42. A single row of the friction bodies 160 may be provided, although in embodiments additional rows may be utilized. The protrusions 162 extend distally to resist distal movement of the prosthetic valve 180, although proximally extending protrusions 162 or a combination of distal and proximally extending protrusions may be utilized. Other configurations of friction bodies 160 may be utilized in examples.

Figure 31:
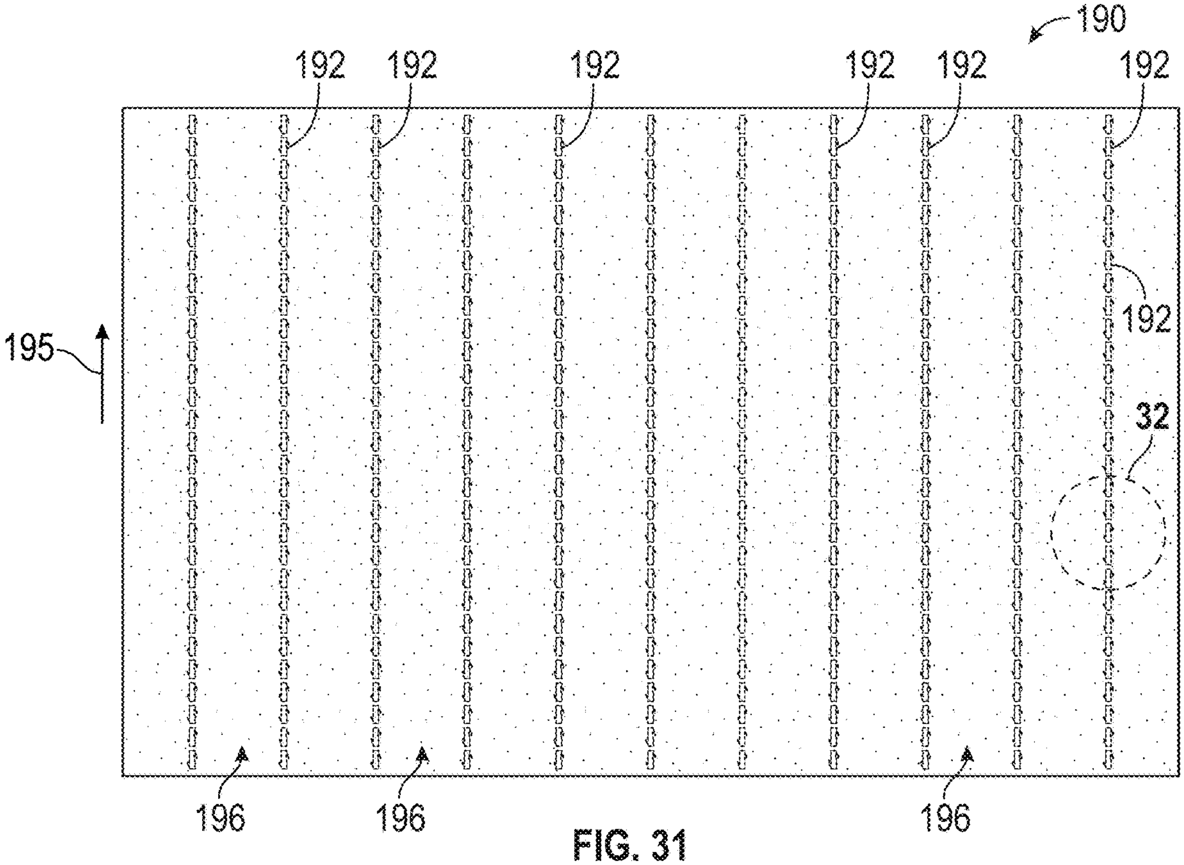
FIG. 31 illustrates a plan view of a fabric including a plurality of friction bodies.

FIG. 31 illustrates an example of a fabric 190 that may utilize one or more friction bodies 192. The friction bodies 192 may be for providing friction with a portion of a heart. The friction bodies 192 may comprise strips in the form of fibers or strands. The fibers may extend along a length of the fabric 190 and may be woven into the fabric 190. For example, during a manufacturing process of the fabric 190, the friction bodies 192 may be woven into the fabric 190 along with the other fibers (such as cross fibers 194 marked in FIG. 32) of the fabric 190. The friction bodies 192 accordingly may be embedded into the fabric 190 and may comprise an integral part of the fabric 190.

In examples, a fiber of each friction body 192 may extend for the entirety of the length 195 of the fabric 190, with the cross fibers 194 being woven over the fiber of the friction body 192. In examples, other lengths of fibers for the friction bodies 192 may be utilized.

Figure 33:
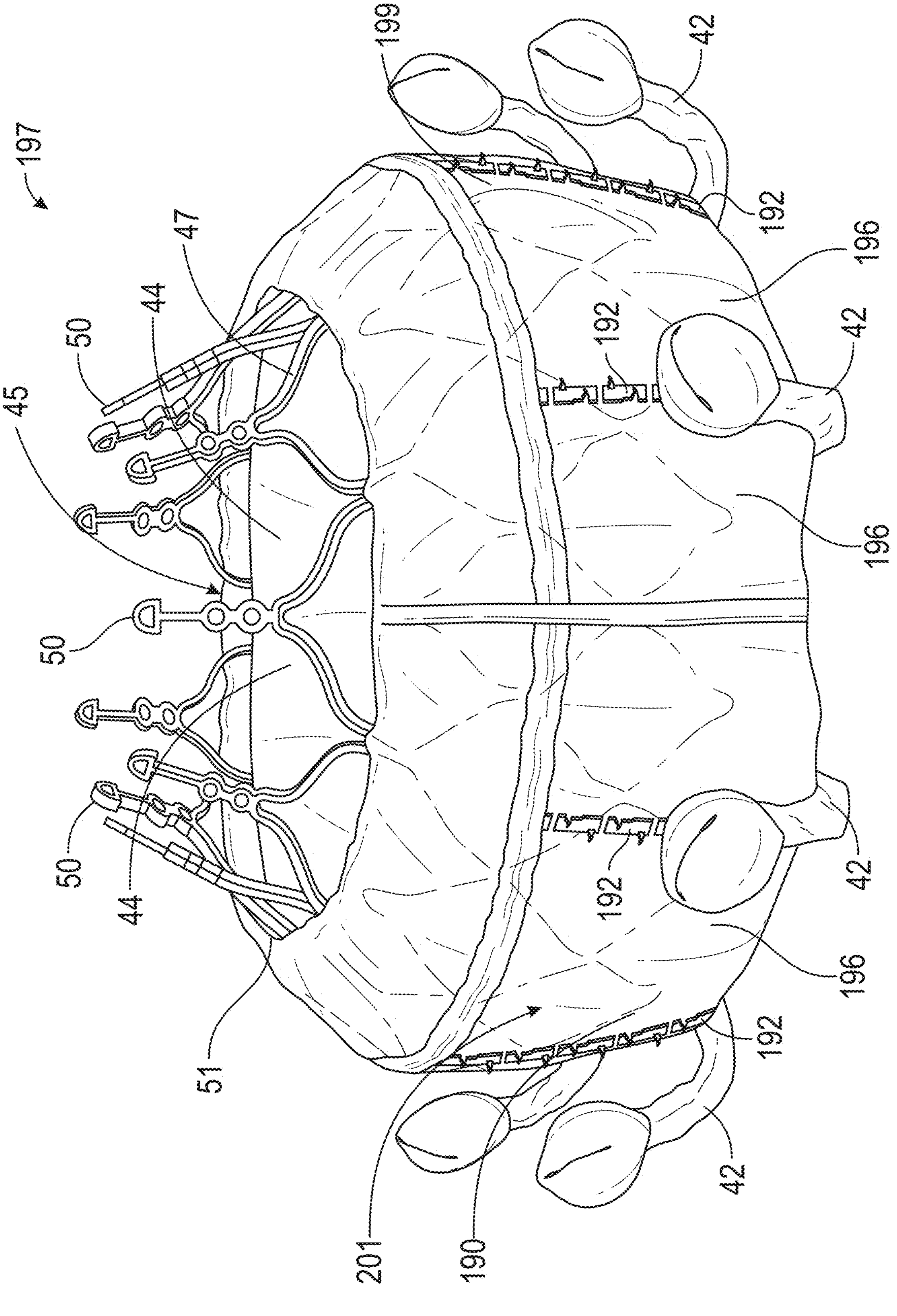
FIG. 33 illustrates a perspective view of a skirt utilizing a fabric shown in FIG. 31.

The friction bodies 192 may extend parallel with each other and may be spaced from each other. The friction bodies 192 may extend axially and thus the spacing may be circumferential when the fabric 190 is applied to a prosthetic valve 197 (as shown in FIG. 33). The circumferential spacing may be equal or varied in examples. Thus, during a weaving process of the fabric 190, the friction bodies 192 may be inserted at equal spacing or equal timing into the other fibers of the fabric 190.

In examples, other angles of the friction bodies 192 may be utilized. For example, a braiding process may be utilized to form the friction bodies 192 into a fabric at a diagonal angle with respect to each other. The braiding process may result in a tube or another shape of resulting fabric.

The fabric 190 may include segments 196 that may be positioned between the friction bodies 192. The segments 196 may be formed of other fibers (including the cross fibers 194 marked in FIG. 32) of the fabric 190. The segments 196 may provide relatively less friction than the friction bodies 192. The segments 196 may be smooth and may comprise a plain weave in examples.

Figure 32:
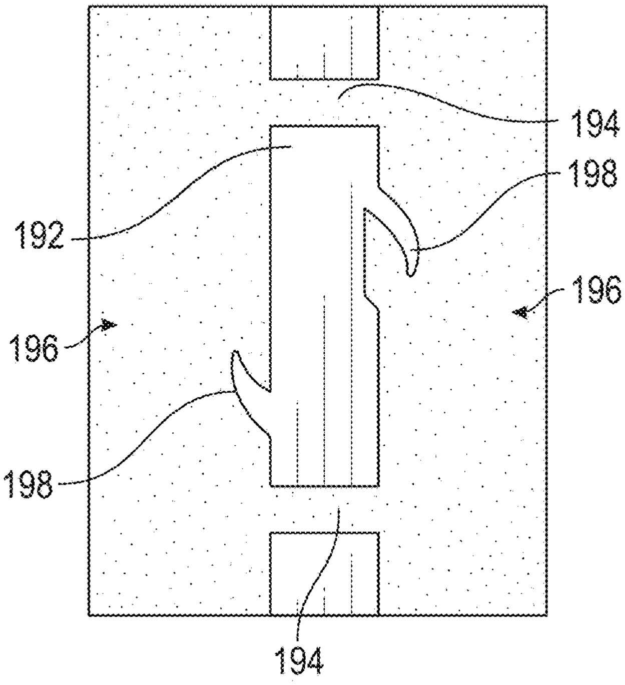
FIG. 32 illustrates a close up view of a portion of the fabric shown in FIG. 31.

FIG. 32 illustrates a close up view of a portion of the fabric 190 within the circle marked 32 in FIG. 31. Referring to FIG. 32, the friction bodies 192 may include one or more protrusions 198 that may be utilized to provide friction with the native valve. The protrusion 198 may extend outward from the fabric 190 and may extend radially outward when applied to a prosthetic valve (as shown in FIG. 33). The protrusions 198 may each extend distally, or may each extend proximally, or a combination of distally and proximally extending protrusions 198 (e.g., bi-directional) may be utilized (as shown in FIG. 32 for example).

The prosthetic valve, for example, may have a proximal portion that may comprise an inflow and a distal portion that may comprise an outflow. The protrusions 198 may be angled in a direction that may be a distal direction, or another direction may be provided in examples (e.g., a proximal direction). The protrusions 198 may be thus angled to resist movement in the distal direction, or in examples may resist movement in the proximal direction.

In examples, the friction bodies 192 may comprise sutures that may be woven into the fabric 190. The sutures may comprise barbed sutures or other forms of sutures that may include protrusions thereon for providing friction with a portion of a heart. The sutures may be woven into the fabric 190 as elongate strips as shown in FIG. 31. Cross fibers 194 marked in FIG. 32 may secure the sutures to the remainder of the fabric 190.

The friction bodies 192 may be made of a material such as a polymer, or a metal, or alloy such as Nitinol (NiTi) or another form of material. The friction bodies 192 may be resorbable in examples.

The fabric 190 may be utilized as a skirt 199 of a prosthetic valve. For example, the fabric 190 may be cut into a desired shape and positioned upon a frame of a prosthetic valve. The friction bodies 192 may be positioned as desired. An outer surface 201 of the skirt 199 may include the friction bodies 192. As shown in FIG. 33, the friction bodies 192 may be in circumferential alignment with the anchors 42. The friction bodies 192 may extend parallel with the anchors 42. The friction bodies 192 may be aligned with a length of a respective one of the elongate arms of the anchors 42.

Each of the friction bodies 192 may comprise a strip that may extend axially with respect to the central axis of the prosthetic valve 197. The central axis may comprise an axis that the flow channel 45 extends along. Other configurations may be utilized as desired.

Figure 34:
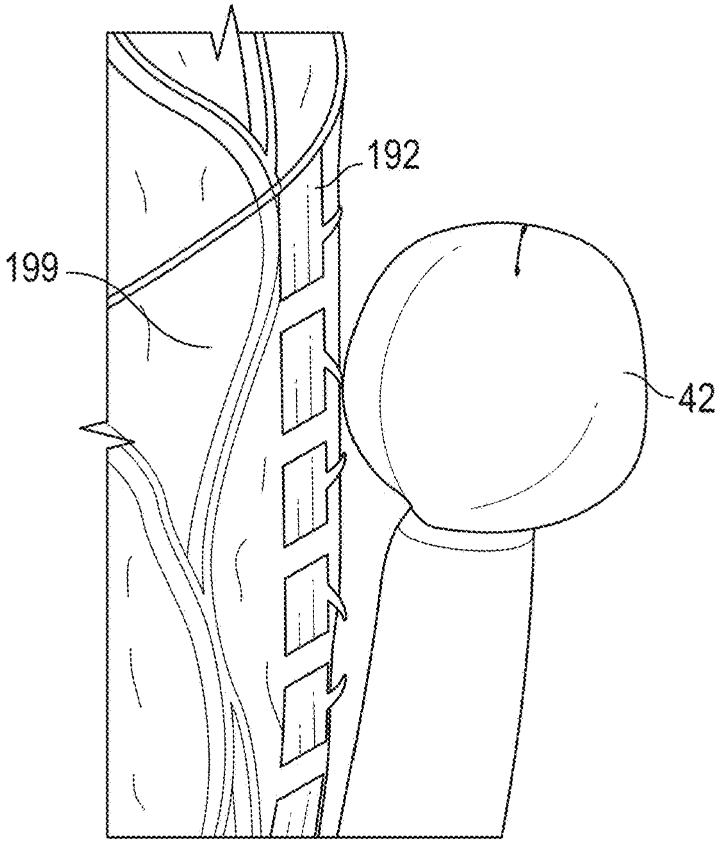
FIG. 34 illustrates a close up view of the skirt shown in FIG. 33.

The position of the friction bodies 192 at the anchors 42 may allow for greater securement of a leaflet at the position of the anchors 42. For example, as shown in FIG. 34, the friction bodies 192 may be positioned radially inward of the anchors 42 and configured to be positioned on an inner side of the native valve leaflet. The friction bodies 192 may be positioned opposed to the anchors 42. The friction body 192 may be configured to provide friction with a leaflet of a native valve. The friction bodies 192 may be positioned on an opposite side of a leaflet of a native valve than a respective one of the anchors 42. The friction bodies 192 accordingly may increase the friction provided at the position of the anchors 42. In examples, other positions of friction bodies 192 may be utilized, such as circumferentially between anchors 42 or in other positions. Other angles of friction bodies 192 may be utilized (e.g., diagonal or circumferential directions) in examples. Combinations of angles of direction may be utilized.

Figure 35:
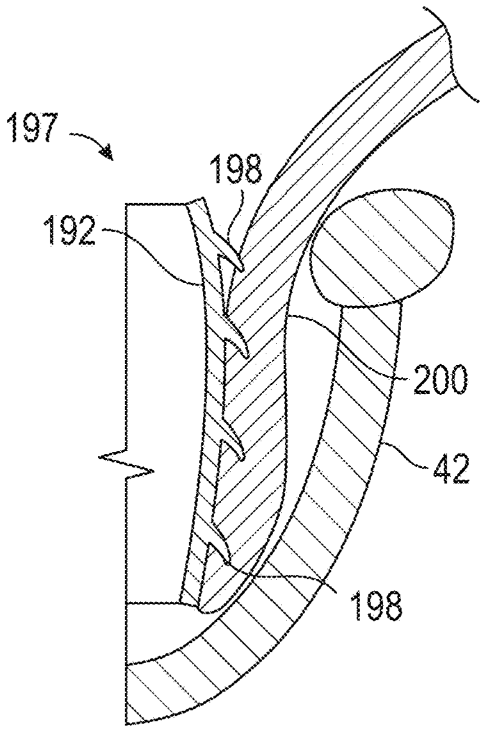
FIG. 35 illustrates a cross sectional schematic view of the skirt shown in FIG. 33 with a native valve leaflet.

The friction bodies 192 may be configured to provide friction with a leaflet of a native valve. FIG. 35 illustrates a cross sectional schematic view of a leaflet 200 positioned between the friction body 192 and the anchor 42. The friction body 192 may increase the friction against the leaflet 200 to secure the prosthetic valve in position. As shown in FIG. 35, the protrusions 198 may each extend distally to resist movement in the distal direction. Such a feature may allow the prosthetic valve 197 to be moved proximally to release the protrusions 198 and be repositioned if desired.

In examples, the protrusions 198 may extend proximally or combinations of distal and proximal protrusions may be utilized. In examples herein, including the examples of FIGS. 23-35, protrusions extending perpendicular to the outer surface of the skirt may be utilized.

Other positions or orientations of the friction bodies 192 may be utilized in examples.

The examples of friction bodies disclosed herein may reduce the possibility of embolization of a prosthetic valve. In examples, the friction bodies may provide a cushion that may reduce the possibility of damage and electrical conduction disturbance to a native valve, among other benefits.

The features of examples disclosed herein may be utilized solely or in combination.

Various modifications of the examples disclosed herein may be provided. Combinations of features across examples may be provided as desired.

The implants disclosed herein may comprise a mitral replacement valve or a tricuspid replacement valve, among other forms of valves (e.g., aortic replacement valves, pulmonary replacement valves, or other valves). The implants disclosed herein may include prosthetic heart valves or other forms of implants, such as stents or filters, or diagnostic devices, among others. The implants may be expandable implants configured to move from a compressed or undeployed state to an expanded or deployed state. The implants may be compressible implants configured to be compressed inward to have a reduced outer profile and to move the implant to the compressed or undeployed state.

Various forms of delivery apparatuses may be utilized with the examples disclosed herein. The delivery apparatuses as disclosed herein may be utilized for aortic, mitral, tricuspid, and pulmonary replacement and repair as well. The delivery apparatuses may comprise delivery apparatuses for delivery of other forms of implants, such as stents or filters, or diagnostic devices, among others.

The implants and the systems disclosed herein may be used in transcatheter aortic valve implantation (TAVI) or replacement of other native heart valves (e.g., mitral, tricuspid, or pulmonary). The delivery apparatuses and the systems disclosed herein may be utilized for transarterial access, including transfemoral access, to a patient's heart. The delivery apparatuses and systems may be utilized in transcatheter percutaneous procedures, including transarterial procedures, which may be transfemoral or transjugular. Transapical procedures, among others, may also be utilized. Other procedures may be utilized as desired.

Features of examples may be modified, substituted, excluded, or combined across examples as desired.

In addition, the methods herein are not limited to the methods specifically described, and may include methods of utilizing the systems and apparatuses disclosed herein. The steps of the methods may be modified, excluded, or added to, with systems, apparatuses, and methods disclosed herein.

For purposes of this description, certain aspects, advantages, and novel features of the examples of this disclosure are described herein. The disclosed methods, apparatuses, and systems should not be construed as limiting in any way. Instead, the present disclosure is directed toward all novel and nonobvious features and aspects of the various disclosed examples, alone and in various combinations and subcombinations with one another. The methods, apparatuses, and systems are not limited to any specific aspect or feature or combination thereof, nor do the disclosed examples require that any one or more specific advantages be present or problems be solved. Features, elements, or components of one example can be combined into other examples herein.

Example 1: A textile for implantation within a portion of a patient's body, the textile comprising: a fabric having a honeycomb weave pattern formed by biocompatible fibers, and heat treated to increase a thickness of the fabric.

Example 2: The textile of any example herein, in particular Example 1, wherein the honeycomb weave pattern includes a repeating pattern of cells, each of the cells including a pit surrounded by walls.

Example 3: The textile of any example herein, in particular Example 1 or Example 2, wherein the honeycomb weave pattern includes between a four end honeycomb repeat and a thirty-two end honeycomb repeat.

Example 4: The textile of any example herein, in particular Examples 1-3, wherein the biocompatible fibers comprise one or more of a biocompatible textured multifilament yarn, a biocompatible textured high shrinkage multifilament yarn, a biocompatible flat multifilament yarn, or a twisted multifilament yarn.

Example 5: The textile of any example herein, in particular Examples 1-4, wherein the biocompatible fibers comprise a biocompatible polymer.

Example 6: The textile of any example herein, in particular Example 5, wherein the biocompatible polymer comprises a bio-resorbable polymer.

Example 7: The textile of any example herein, in particular Example 6, wherein the bio-resorbable polymer comprises one or more of polyglycolic acid (PGA), polylactic acid (PLA), polycaprolactone (PCL), or polylactide glycolide copolymers (PLGA).

Example 8: The textile of any example herein, in particular Example 5, wherein the biocompatible polymer comprises one or more of polyester, polypropylene, nylon, ultra high molecular weight polyethylene, polytetrafluoroethylene, expanded polytetrafluoroethylene, or polyetheretherketone.

Example 9: The textile of any example herein, in particular Examples 1-8, wherein each of the biocompatible fibers extend continuously from a first end of the fabric to a second opposite end of the fabric.

Example 10: The textile of any example herein, in particular Examples 1-9, wherein the fabric has a compressibility between 10 percent to 100 percent.

Example 11: The textile of any example herein, in particular Examples 1-10, wherein the fabric has a compressibility greater than 80 percent.

Example 12: The textile of any example herein, in particular Examples 1-11, wherein the fabric has a fiber density of between 100 to 400 ends per inch, and 100 to 300 picks per inch.

Example 13: The textile of any example herein, in particular Examples 1-12, wherein the thickness of the fabric increases by more than 100 percent due to the heat treatment.

Example 14: The textile of any example herein, in particular Examples 1-13, wherein the thickness of the fabric increases by more than 1,800 percent due to the heat treatment.

Example 15: The textile of any example herein, in particular Examples 1-14, wherein the thickness of the fabric is at least 0.5 millimeters.

Example 16: The textile of any example herein, in particular Examples 1-15, wherein a length of the fabric decreases by at least 20 percent due to the heat treatment and a width of the fabric decreases by at least 40 percent due to the heat treatment.

Example 17: The textile of any example herein, in particular Examples 1-16, wherein the heat treatment shrinks the biocompatible fibers.

Example 18: The textile of any example herein, in particular Examples 1-17, wherein the biocompatible fibers are wavy fibers.

Example 19: The textile of any example herein, in particular Examples 1-18, wherein the heat treatment increases a crimp of the biocompatible fibers.

Example 20: The textile of any example herein, in particular Examples 1-19, wherein the fabric comprises a single layer.

Example 21: A prosthetic valve configured to be deployed to a native valve of a heart, the prosthetic valve comprising: a plurality of prosthetic valve leaflets; one or more anchors coupled to the plurality of prosthetic valve leaflets and each configured to anchor to a portion of the heart; and one or more pads coupled to the one or more anchors, each of the one or more pads including a fabric having a honeycomb weave pattern.

Example 22: The prosthetic valve of any example herein, in particular Example 21, wherein the prosthetic valve includes an inflow end and an outflow end, and the one or more anchors are positioned at the outflow end of the prosthetic valve.

Example 23: The prosthetic valve of any example herein, in particular Example 21 or Example 22, wherein the one or more anchors comprise ventricular anchors.

Example 24: The prosthetic valve of any example herein, in particular Examples 21-23, wherein the one or more pads are coupled to a tip of the one or more anchors.

Example 25: The prosthetic valve of any example herein, in particular Examples 21-24, wherein each of the one or more anchors has a hook shape.

Example 26: The prosthetic valve of any example herein, in particular Examples 21-25, wherein each of the one or more anchors includes a surface facing radially inward and a surface facing radially outward, and the one or more pads cover the surface facing radially inward.

Example 27: The prosthetic valve of any example herein, in particular Example 26, wherein each of the one or more anchors is configured to hook around a native valve leaflet, with the surface facing radially inward facing towards the native valve leaflet.

Example 28: The prosthetic valve of any example herein, in particular Examples 21-27, further comprising a frame supporting the plurality of prosthetic valve leaflets, and wherein the one or more anchors are coupled to the frame.

Example 29: The prosthetic valve of any example herein, in particular Examples 21-28, wherein each of the one or more pads includes a plurality of layers of the fabric.

Example 30: The prosthetic valve of any example herein, in particular Examples 21-29, wherein the honeycomb weave pattern includes a repeating pattern of cells, each of the cells including a pit surrounded by walls.

Example 31: The prosthetic valve of any example herein, in particular Examples 21-30, wherein the fabric is formed by biocompatible fibers that are wavy.

Example 32: The prosthetic valve of any example herein, in particular Example 31, wherein the fabric is heat treated to increase a thickness of the fabric.

Example 33: The prosthetic valve of any example herein, in particular Example 32, wherein the heat treatment increases a crimp of the biocompatible fibers.

Example 34: The prosthetic valve of any example herein, in particular Examples 21-33, wherein the fabric has a compressibility greater than 80 percent.

Example 35: The prosthetic valve of any example herein, in particular Examples 21-34, wherein the fabric has a fiber density of between 100 to 400 ends per inch, and 100 to 300 picks per inch.

Example 36: A method of fabricating a textile for implantation within a portion of a patient's body, the method comprising: providing a fabric having a honeycomb weave pattern formed by biocompatible fibers; and heat treating the fabric to increase a thickness of the fabric.

Example 37: The method of any example herein, in particular Example 36, further comprising forming the honeycomb weave pattern with the biocompatible fibers.

Example 38: The method of any example herein, in particular Example 36 or Example 37, wherein the honeycomb weave pattern includes a repeating pattern of cells, each of the cells including a pit surrounded by walls.

Example 39: The method of any example herein, in particular Examples 36-38, wherein the honeycomb weave pattern includes between a four end honeycomb repeat and a thirty-two end honeycomb repeat.

Example 40: The method of any example herein, in particular Examples 36-39, wherein the biocompatible fibers comprise one or more of a biocompatible textured multifilament yarn, a biocompatible textured high shrinkage multifilament yarn, a biocompatible flat multifilament yarn, or a twisted multifilament yarn.

Example 41: The method of any example herein, in particular Examples 36-40, wherein the biocompatible fibers comprise a biocompatible polymer.

Example 42: The method of any example herein, in particular Example 41, wherein the biocompatible polymer comprises a bio-resorbable polymer.

Example 43: The method of any example herein, in particular Examples 36-42, wherein the thickness of the fabric increases by more than 100 percent due to the heat treatment.

Example 44: The method of any example herein, in particular Examples 36-43, wherein the thickness of the fabric increases by more than 1,800 percent due to the heat treatment.

Example 45: The method of any example herein, in particular Examples 36-44, wherein a length of the fabric decreases by at least 20 percent due to the heat treatment and a width of the fabric decreases by at least 40 percent due to the heat treatment.

Example 46: The method of any example herein, in particular Examples 36-45, wherein the heat treatment increases a crimp of the biocompatible fibers.

Example 47: The method of any example herein, in particular Examples 36-46, wherein the fabric following the heat treatment has a compressibility greater than 80 percent.

Example 48: The method of any example herein, in particular Examples 36-47, wherein the fabric following the heat treatment has a fiber density of between 100 to 400 ends per inch, and 100 to 300 picks per inch.

Example 49: The method of any example herein, in particular Examples 36-48, wherein each of the biocompatible fibers extend continuously from a first end of the fabric to a second opposite end of the fabric.

Example 50: The method of any example herein, in particular Examples 36-49, wherein the fabric comprises a single layer.

Example 51: A method comprising: deploying a prosthetic valve to a native valve of a patient's heart, the prosthetic valve including: a plurality of prosthetic valve leaflets, one or more anchors coupled to the plurality of prosthetic valve leaflets and each configured to anchor to a portion of the patient's heart, and one or more pads coupled to the one or more anchors, each of the one or more pads including a fabric having a honeycomb weave pattern.

Example 52: The method of any example herein, in particular Example 51, wherein the one or more anchors comprise ventricular anchors.

Example 53: The method of any example herein, in particular Example 51 or Example 52, wherein the one or more pads are coupled to a tip of the one or more anchors.

Example 54: The method of any example herein, in particular Examples 51-53, further comprising hooking each of the one or more anchors around a native valve leaflet.

Example 55: The method of any example herein, in particular Examples 51-54, wherein each of the one or more anchors includes a surface facing radially inward and a surface facing radially outward, and the one or more pads cover the surface facing radially inward.

Example 56: The method of any example herein, in particular Example 55, further comprising hooking each of the one or more anchors around a native valve leaflet, with the surface facing radially inward facing towards the native valve leaflet.

Example 57: The method of any example herein, in particular Examples 51-56, further comprising a frame supporting the plurality of prosthetic valve leaflets, and wherein the one or more anchors are coupled to the frame.

Example 58: The method of any example herein, in particular Examples 51-57, wherein the native valve is a native mitral valve or a native tricuspid valve.

Example 59: The method of any example herein, in particular Examples 51-58, wherein each of the one or more pads includes a plurality of layers of the fabric.

Example 60: The method of any example herein, in particular Examples 51-59, wherein the honeycomb weave pattern includes a repeating pattern of cells, each of the cells including a pit surrounded by walls.

Example 61: The method of any example herein, in particular Examples 51-60, wherein the fabric is formed by biocompatible fibers that are wavy.

Example 62: The method of any example herein, in particular Example 61, wherein the fabric is heat treated to increase a thickness of the fabric.

Example 63: The method of any example herein, in particular Example 62, wherein the heat treatment increases a crimp of the biocompatible fibers.

Example 64: The method of any example herein, in particular Examples 51-63, wherein the fabric has a compressibility greater than 80 percent.

Example 65: The method of any example herein, in particular Examples 51-64, wherein the fabric has a fiber density of between 100 to 400 ends per inch, and 100 to 300 picks per inch.

Example 66: A prosthetic valve configured to be deployed to a native valve of a heart, the prosthetic valve comprising: a plurality of prosthetic valve leaflets; and a valve body supporting the plurality of prosthetic valve leaflets and including a skirt, at least a portion of the skirt having a honeycomb weave pattern.

Example 67: The prosthetic valve of any example herein, in particular Example 66, wherein the skirt comprises a sealing skirt for sealing with a portion of the heart.

Example 68: The prosthetic valve of any example herein, in particular Example 66 or Example 67, wherein the valve body includes a frame, and the skirt is positioned radially outward of the frame.

Example 69: The prosthetic valve of any example herein, in particular Example 68, wherein the frame comprises an outer frame, and the prosthetic valve further comprises an inner frame positioned radially inward of the outer frame.

Example 70: The prosthetic valve of any example herein, in particular Examples 66-69, wherein the valve body surrounds a flow channel, and the plurality of prosthetic valve leaflets extend radially inward from the valve body towards the flow channel.

Example 71: The prosthetic valve of any example herein, in particular Examples 66-70, wherein an outer surface of the skirt includes the honeycomb weave pattern.

Example 72: The prosthetic valve of any example herein, in particular Examples 66-71, further comprising a plurality of anchors coupled to the plurality of prosthetic valve leaflets and each configured to anchor to a portion of the heart.

Example 73: The prosthetic valve of any example herein, in particular Example 72, wherein the portion of the skirt having the honeycomb weave pattern extends circumferentially between adjacent anchors of the plurality of anchors.

Example 74: The prosthetic valve of any example herein, in particular Example 72 or Example 73, wherein the portion of the skirt having the honeycomb weave pattern is positioned opposed to each of the plurality of anchors.

Example 75: The prosthetic valve of any example herein, in particular Examples 72-74, wherein each of the plurality of anchors has a hook shape.

Example 76: The prosthetic valve of any example herein, in particular Examples 66-75, wherein the portion of the skirt having the honeycomb weave pattern is configured to provide friction with a leaflet of the native valve.

Example 77: The prosthetic valve of any example herein, in particular Examples 66-76, wherein the portion of the skirt having the honeycomb weave pattern comprises a pad.

Example 78: The prosthetic valve of any example herein, in particular Examples 66-77, wherein the portion of the skirt having the honeycomb weave pattern is configured to provide a cushion with the native valve.

Example 79: The prosthetic valve of any example herein, in particular Examples 66-78, wherein the portion of the skirt having the honeycomb weave pattern is configured to be compressible.

Example 80: The prosthetic valve of any example herein, in particular Examples 66-79, wherein the honeycomb weave pattern includes a repeating pattern of cells, each of the cells including a pit surrounded by walls.

Example 81: The prosthetic valve of any example herein, in particular Examples 66-80, wherein the honeycomb weave pattern is formed by biocompatible fibers that are wavy.

Example 82: The prosthetic valve of any example herein, in particular Example 81, wherein the honeycomb weave pattern comprises a fabric that is heat treated to increase a thickness of the fabric.

Example 83: The prosthetic valve of any example herein, in particular Example 82, wherein the heat treatment increases a crimp of the biocompatible fibers.

Example 84: The prosthetic valve of any example herein, in particular Examples 66-83, wherein the honeycomb weave pattern comprises a fabric has a compressibility greater than 80 percent.

Example 85: The prosthetic valve of any example herein, in particular Examples 66-84, wherein the honeycomb weave pattern comprises a fabric having a fiber density of between 100 to 400 ends per inch, and 100 to 300 picks per inch.

Example 86: A prosthetic valve configured to be deployed to a native valve of a heart, the prosthetic valve comprising: a plurality of prosthetic valve leaflets; and a valve body supporting the plurality of prosthetic valve leaflets and including a skirt, at least a portion of the skirt including one or more friction bodies for providing friction with a portion of the heart.

Example 87: The prosthetic valve of any example herein, in particular Example 86, wherein the skirt comprises a sealing skirt for sealing with a portion of the heart.

Example 88: The prosthetic valve of any example herein, in particular Example 86 or Example 87, wherein the valve body includes a frame, and the skirt is positioned radially outward of the frame.

Example 89: The prosthetic valve of any example herein, in particular Example 88, wherein the frame comprises an outer frame, and the prosthetic valve further comprises an inner frame positioned radially inward of the outer frame.

Example 90: The prosthetic valve of any example herein, in particular Examples 86-89, wherein the valve body surrounds a flow channel, and the plurality of prosthetic valve leaflets extend radially inward from the valve body towards the flow channel.

Example 91: The prosthetic valve of any example herein, in particular Examples 86-90, wherein an outer surface of the skirt includes the one or more friction bodies.

Example 92: The prosthetic valve of any example herein, in particular Examples 86-91, wherein the one or more friction bodies are configured to provide friction with a leaflet of the native valve.

Example 93: The prosthetic valve of any example herein, in particular Examples 86-92, wherein the one or more friction bodies each comprise a strip.

Example 94: The prosthetic valve of any example herein, in particular Examples 86-93, wherein the valve body surrounds a flow channel extending along an axis, and each of the one or more friction bodies comprises a strip extending axially with respect to the axis.

Example 95: The prosthetic valve of any example herein, in particular Examples 86-94, further comprising a plurality of anchors coupled to the plurality of prosthetic valve leaflets and each configured to anchor to a portion of the heart.

Example 96: The prosthetic valve of any example herein, in particular Example 95, wherein the one or more friction bodies are positioned opposed to each of the plurality of anchors.

Example 97: The prosthetic valve of any example herein, in particular Example 95 or Example 96, wherein each of the plurality of anchors has a hook shape.

Example 98: The prosthetic valve of any example herein, in particular Examples wherein each of the plurality of anchors comprises an elongate arm having a length, and the one or more friction bodies each comprise a strip aligned with the length of a respective one of the elongate arms.

Example 99: The prosthetic valve of any example herein, in particular Examples wherein each of the one or more friction bodies are configured to be positioned on an opposite side of a leaflet of the native valve than a respective one of the plurality of anchors.

Example 100: The prosthetic valve of any example herein, in particular Examples 86-99, wherein the one or more friction bodies include one or more protrusions.

Example 101: The prosthetic valve of any example herein, in particular Example 100, wherein a proximal portion of the valve body comprises an inflow of the prosthetic valve and a distal portion of the valve body comprises an outflow of the prosthetic valve, and the one or more protrusions are angled to resist movement in a distal direction or in a proximal direction.

Example 102: The prosthetic valve of any example herein, in particular Examples 86-101, wherein the one or more friction bodies include a patch having a plurality of loops.

Example 103: The prosthetic valve of any example herein, in particular Examples 86-102, wherein the skirt comprises a fabric and the one or more friction bodies are embedded in the fabric.

Example 104: The prosthetic valve of any example herein, in particular Examples 86-103, wherein the one or more friction bodies include one or more wires having a protrusion for providing friction with the portion of the heart.

Example 105: The prosthetic valve of any example herein, in particular Examples 86-104, wherein the skirt comprises a fabric and the one or more friction bodies are woven into the fabric.

Example 106: The prosthetic valve of any example herein, in particular Examples 86-105, wherein the one or more friction bodies include one or more sutures having a protrusion for providing friction with the portion of the heart.

Example 107: The prosthetic valve of any example herein, in particular Examples 86-106, wherein the one or more friction bodies include a honeycomb weave pattern.

Example 108: The prosthetic valve of any example herein, in particular Example 107, wherein the honeycomb weave pattern includes a repeating pattern of cells, each of the cells including a pit surrounded by walls.

Example 109: The prosthetic valve of any example herein, in particular Example 107 or Example 108, wherein the honeycomb weave pattern is formed by biocompatible fibers that are wavy.

Example 110: The prosthetic valve of any example herein, in particular Examples 86-109, wherein the prosthetic valve comprises a mitral replacement valve or a tricuspid replacement valve.

Example 111: A method comprising: deploying a prosthetic valve to a native valve of a patient's heart, the prosthetic valve including: a plurality of prosthetic valve leaflets, and a valve body supporting the plurality of prosthetic valve leaflets and including a skirt, at least a portion of the skirt having a honeycomb weave pattern.

Example 112: The method of any example herein, in particular Example 111, wherein the skirt comprises a sealing skirt for sealing with a portion of the heart.

Example 113: The method of any example herein, in particular Example 111 or Example 112, wherein the valve body includes a frame, and the skirt is positioned radially outward of the frame.

Example 114: The method of any example herein, in particular Example 113, wherein the frame comprises an outer frame, and the prosthetic valve further comprises an inner frame positioned radially inward of the outer frame.

Example 115: The method of any example herein, in particular Examples 111-114, wherein the valve body surrounds a flow channel, and the plurality of prosthetic valve leaflets extend radially inward from the valve body towards the flow channel.

Example 116: The method of any example herein, in particular Examples 111-115, wherein an outer surface of the skirt includes the honeycomb weave pattern.

Example 117: The method of any example herein, in particular Examples 111-116, wherein a plurality of anchors are coupled to the plurality of prosthetic valve leaflets and each configured to anchor to a portion of the heart.

Example 118: The method of any example herein, in particular Example 117, wherein the portion of the skirt having the honeycomb weave pattern extends circumferentially between adjacent anchors of the plurality of anchors.

Example 119: The method of any example herein, in particular Example 117 or Example 118, wherein the portion of the skirt having the honeycomb weave pattern is positioned opposed to each of the plurality of anchors.

Example 120: The method of any example herein, in particular Examples 117-119, wherein each of the plurality of anchors has a hook shape.

Example 121: The method of any example herein, in particular Examples 111-120, wherein the portion of the skirt having the honeycomb weave pattern is configured to provide friction with a leaflet of the native valve.

Example 122: The method of any example herein, in particular Examples 111-121, wherein the portion of the skirt having the honeycomb weave pattern comprises a pad.

Example 123: The method of any example herein, in particular Examples 111-122, wherein the portion of the skirt having the honeycomb weave pattern is configured to provide a cushion with the native valve.

Example 124: The method of any example herein, in particular Examples 111-123, wherein the portion of the skirt having the honeycomb weave pattern is configured to be compressible.

Example 125: The method of any example herein, in particular Examples 111-124, wherein the honeycomb weave pattern includes a repeating pattern of cells, each of the cells including a pit surrounded by walls.

Example 126: The method of any example herein, in particular Examples 111-125, wherein the honeycomb weave pattern is formed by biocompatible fibers that are wavy.

Example 127: The method of any example herein, in particular Example 126, wherein the honeycomb weave pattern comprises a fabric that is heat treated to increase a thickness of the fabric.

Example 128: The method of any example herein, in particular Example 127, wherein the heat treatment increases a crimp of the biocompatible fibers.

Example 129: The method of any example herein, in particular Examples 111-128, wherein the honeycomb weave pattern comprises a fabric has a compressibility greater than 80 percent.

Example 130: The method of any example herein, in particular Examples 111-129, wherein the honeycomb weave pattern comprises a fabric having a fiber density of between 100 to 400 ends per inch, and 100 to 300 picks per inch.

Example 131: A method comprising: deploying a prosthetic valve to a native valve of a patient's heart, the prosthetic valve including: a plurality of prosthetic valve leaflets, and a valve body supporting the plurality of prosthetic valve leaflets and including a skirt, at least a portion of the skirt including one or more friction bodies for providing friction with a portion of the heart.

Example 132: The method of any example herein, in particular Example 131, wherein the skirt comprises a sealing skirt for sealing with a portion of the heart.

Example 133: The method of any example herein, in particular Example 131 or Example 132, wherein the valve body includes a frame, and the skirt is positioned radially outward of the frame.

Example 134: The method of any example herein, in particular Example 133, wherein the frame comprises an outer frame, and the prosthetic valve further comprises an inner frame positioned radially inward of the outer frame.

Example 135: The method of any example herein, in particular Examples 131-134, wherein the valve body surrounds a flow channel, and the plurality of prosthetic valve leaflets extend radially inward from the valve body towards the flow channel.

Example 136: The method of any example herein, in particular Examples 131-135, wherein an outer surface of the skirt includes the one or more friction bodies.

Example 137: The method of any example herein, in particular Examples 131-136, wherein the one or more friction bodies are configured to provide friction with a leaflet of the native valve.

Example 138: The method of any example herein, in particular Examples 131-137, wherein the one or more friction bodies each comprise a strip.

Example 139: The method of any example herein, in particular Examples 131-138, wherein the valve body surrounds a flow channel extending along an axis, and each of the one or more friction bodies comprises a strip extending axially with respect to the axis.

Example 140: The method of any example herein, in particular Examples 131-139, wherein a plurality of anchors are coupled to the plurality of prosthetic valve leaflets and each configured to anchor to a portion of the heart.

Example 141: The method of any example herein, in particular Example 140, wherein the one or more friction bodies are positioned opposed to each of the plurality of anchors.

Example 142: The method of any example herein, in particular Example 140 or Example 141, wherein each of the plurality of anchors has a hook shape.

Example 143: The method of any example herein, in particular Examples 140-142, wherein each of the plurality of anchors comprises an elongate arm having a length, and the one or more friction bodies each comprise a strip aligned with the length of a respective one of the elongate arms.

Example 144: The method of any example herein, in particular Examples 140-143, wherein each of the one or more friction bodies are configured to be positioned on an opposite side of a leaflet of the native valve than a respective one of the plurality of anchors.

Example 145: The method of any example herein, in particular Examples 131-144, wherein the one or more friction bodies include one or more protrusions.

Example 146: The method of any example herein, in particular Example 145, wherein a proximal portion of the valve body comprises an inflow of the prosthetic valve and a distal portion of the valve body comprises an outflow of the prosthetic valve, and the one or more protrusions are angled to resist movement in a distal direction or in a proximal direction.

Example 147: The method of any example herein, in particular Examples 131-146, wherein the one or more friction bodies include a patch having a plurality of loops.

Example 148: The method of any example herein, in particular Examples 131-147, wherein the skirt comprises a fabric and the one or more friction bodies are embedded in the fabric.

Example 149: The method of any example herein, in particular Examples 131-148, wherein the one or more friction bodies include one or more wires having a protrusion for providing friction with the portion of the heart.

Example 150: The method of any example herein, in particular Examples 131-149, wherein the skirt comprises a fabric and the one or more friction bodies are woven into the fabric.

Example 151: The method of any example herein, in particular Examples 131-150, wherein the one or more friction bodies include one or more sutures having a protrusion for providing friction with the portion of the heart.

Example 152: The method of any example herein, in particular Examples 131-151, wherein the one or more friction bodies include a honeycomb weave pattern.

Example 153: The method of any example herein, in particular Example 152, wherein the honeycomb weave pattern includes a repeating pattern of cells, each of the cells including a pit surrounded by walls.

Example 154: The method of any example herein, in particular Example 152 or Example 153, wherein the honeycomb weave pattern is formed by biocompatible fibers that are wavy.

Example 155: The method of any example herein, in particular Examples 131-154, wherein the prosthetic valve comprises a mitral replacement valve or a tricuspid replacement valve.

Any of the features of any of the examples, including but not limited to any of the first through 155 examples referred to above, is applicable to all other aspects and examples identified herein, including but not limited to any examples of any of the first through 155 examples referred to above. Moreover, any of the features of an example of the various examples, including but not limited to any examples of any of the first through 155 examples referred to above, is independently combinable, partly or wholly with other examples described herein in any way, e.g., one, two, or three or more examples may be combinable in whole or in part. Further, any of the features of the various examples, including but not limited to any examples of any of the first through 155 examples referred to above, may be made optional to other examples. Any example of a method can be performed by a system or apparatus of another example, and any aspect or example of a system or apparatus can be configured to perform a method of another aspect or example, including but not limited to any examples of any of the first through 155 examples referred to above.

In closing, it is to be understood that although aspects of the present specification are highlighted by referring to specific examples, one skilled in the art will readily appreciate that these disclosed examples are only illustrative of the principles of the subject matter disclosed herein. Therefore, it should be understood that the disclosed subject matter is in no way limited to a particular methodology, protocol, and/or reagent, etc., described herein. As such, various modifications or changes to or alternative configurations of the disclosed subject matter can be made in accordance with the teachings herein without departing from the spirit of the present specification. Lastly, the terminology used herein is for the purpose of describing particular examples only, and is not intended to limit the scope of systems, apparatuses, and methods as disclosed herein, which is defined solely by the claims. Accordingly, the systems, apparatuses, and methods are not limited to that precisely as shown and described.

Certain examples of systems, apparatuses, and methods are described herein, including the best mode known to the inventors for carrying out the same. Of course, variations on these described examples will become apparent to those of ordinary skill in the art upon reading the foregoing description. The inventor expects skilled artisans to employ such variations as appropriate, and the inventors intend for the systems, apparatuses, and methods to be practiced otherwise than specifically described herein. Accordingly, the systems, apparatuses, and methods include all modifications and equivalents of the subject matter recited in the claims appended hereto as permitted by applicable law. Moreover, any combination of the above-described examples in all possible variations thereof is encompassed by the systems, apparatuses, and methods unless otherwise indicated herein or otherwise clearly contradicted by context.

Groupings of alternative examples, elements, or steps of the systems, apparatuses, and methods are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses an approximation that may vary, yet is capable of performing the desired operation or process discussed herein.

The terms "a," "an," "the" and similar referents used in the context of describing the systems, apparatuses, and methods (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the systems, apparatuses, and methods and does not pose a limitation on the scope of the systems, apparatuses, and methods otherwise claimed. No language in the present specification should be construed as indicating any non-claimed element essential to the practice of the systems, apparatuses, and methods.

All patents, patent publications, and other publications referenced and identified in the present specification are individually and expressly incorporated herein by reference in their entirety for the purpose of describing and disclosing, for example, the compositions and methodologies described in such publications that might be used in connection with the systems, apparatuses, and methods. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

What is claimed is:

1. A prosthetic heart valve for implantation in a native valve of a heart, the prosthetic heart valve comprising:

a plurality of prosthetic valve leaflets positioned within a flow channel of the prosthetic heart valve;

an expandable and compressible inner frame supporting the plurality of prosthetic valve leaflets;

an expandable and compressible sealing body for sealing with a portion of the heart, the sealing body positioned radially outward of the inner frame, wherein at least a portion of the sealing body includes a plurality of friction bodies along an outer surface thereof; and a plurality of ventricular anchors extending from an outflow end of the prosthetic heart valve for capturing leaflets of the native valve between the ventricular anchors and the outer surface of the sealing body;

wherein:

the friction bodies contact the captured leaflets of the native valve for enhancing securement of the prosthetic heart valve in the native valve; and each of the friction bodies includes a fabric having a honeycomb weave pattern and wherein the honeycomb weave pattern is formed by fibers that have been heat treated to increase a thickness of the honeycomb weave pattern.

2. The prosthetic heart valve of claim 1, wherein the friction bodies include a protrusion coupled to a wire.

3. The prosthetic heart valve of claim 1, wherein the fabric is a first fabric and the prosthetic heart valve further comprises a second fabric coupled to the plurality of ventricular anchors, wherein the second fabric has a second honeycomb weave pattern formed by wavy fibers that have been heat treated to increase a thickness of the second honeycomb weave pattern.

4. The prosthetic heart valve of claim 1, wherein the sealing body comprises a skirt and wherein the outer surface of the sealing body is the outer surface of the skirt.

5. The prosthetic heart valve of claim 4, wherein the friction bodies are embedded in the skirt.

6. The prosthetic heart valve of claim 4, wherein the friction bodies include protrusions extending from the outer surface of the skirt.

7. The prosthetic heart valve of claim 4, wherein the sealing body is a metallic outer frame coupled to the inner frame and wherein the skirt is wrapped around the outer frame.

8. The prosthetic heart valve of claim 7, wherein the outer frame is coupled to the inner frame at an inflow end of the prosthetic heart valve.

9. The prosthetic heart valve of claim 1, wherein each of the plurality of ventricular anchors has a hook shape for hooking around a leaflet of the native valve.

10. The prosthetic heart valve of claim 1, wherein each of the friction bodies is positioned on the outer surface of the sealing body at a location opposed to one of the ventricular anchors.

11. The prosthetic heart valve of claim 1, wherein the prosthetic heart valve is sized for replacing a native mitral valve or a native tricuspid valve.

12. A prosthetic heart valve for implantation in a native valve of a heart, the prosthetic heart valve comprising:

a plurality of prosthetic valve leaflets positioned within a flow channel of the prosthetic heart valve;

a frame supporting the plurality of prosthetic valve leaflets;

an anchor coupled to the frame and adapted to anchor the frame to the native valve; and a pad coupled to the anchor, the pad adapted to cushion the anchor against a portion of the native valve and including a fabric having a honeycomb weave pattern, wherein the honeycomb weave pattern is formed by fibers that are wavy and have been heat treated to increase a thickness of the honeycomb weave pattern.

13. The prosthetic heart valve of claim 12, wherein the anchor has a hook shape for hooking around a leaflet of the native valve.

14. The prosthetic heart valve of claim 12, wherein the anchor includes an elongate arm having a length and extending to a tip, and the pad covers the tip of the arm or extends along the length of the elongate arm.

15. A prosthetic heart valve for implantation in a native valve of a heart, the prosthetic heart valve comprising:

a plurality of prosthetic valve leaflets positioned within a flow channel of the prosthetic heart valve;

an expandable and compressible inner frame supporting the plurality of prosthetic valve leaflets;

an expandable and compressible sealing body for sealing with a portion of the heart, the sealing body positioned radially outward of the inner frame, wherein at least a portion of the sealing body includes a plurality of friction bodies along an outer surface thereof;

a plurality of ventricular anchors extending from an outflow end of the prosthetic heart valve for capturing leaflets of the native valve between the ventricular anchors and the outer surface of the sealing body; and for each of the ventricular anchors, a fabric coupled to the anchor, wherein the fabric has a honeycomb weave pattern formed by wavy fibers that have been heat treated to increase a thickness of the honeycomb weave pattern;

wherein the friction bodies contact the captured leaflets of the native valve for enhancing securement of the prosthetic heart valve in the native valve.

16. A prosthetic heart valve for implantation in a native valve of a heart, the prosthetic heart valve comprising:

a plurality of prosthetic valve leaflets positioned within a flow channel of the prosthetic heart valve;

an expandable and compressible inner frame supporting the plurality of prosthetic valve leaflets;

an expandable and compressible sealing body for sealing with a portion of the heart, the sealing body positioned radially outward of the inner frame, wherein at least a portion of the sealing body includes a plurality of friction bodies along an outer surface thereof; and a plurality of ventricular anchors extending from an outflow end of the prosthetic heart valve for capturing leaflets of the native valve between the ventricular anchors and the outer surface of the sealing body;

wherein:

the friction bodies contact the captured leaflets of the native valve for enhancing securement of the prosthetic heart valve in the native valve; and each of the friction bodies includes a patch having a plurality of loops.

17. A prosthetic heart valve for implantation in a native valve of a heart, the prosthetic heart valve comprising:

a plurality of prosthetic valve leaflets positioned within a flow channel of the prosthetic heart valve;

an expandable and compressible inner frame supporting the plurality of prosthetic valve leaflets;

an expandable and compressible sealing body for sealing with a portion of the heart, the sealing body positioned radially outward of the inner frame, wherein at least a portion of the sealing body includes a plurality of friction bodies along an outer surface thereof; and a plurality of ventricular anchors extending from an outflow end of the prosthetic heart valve for capturing leaflets of the native valve between the ventricular anchors and the outer surface of the sealing body;

wherein:

the friction bodies contact the captured leaflets of the native valve for enhancing securement of the prosthetic heart valve in the native valve; and each of the friction bodies includes barbed sutures.

* * * * *